(12) United States Patent
Jeong et al.

(10) Patent No.: US 11,464,770 B2
(45) Date of Patent: *Oct. 11, 2022

(54) ANTICANCER PHARMACEUTICAL COMPOSITION

(71) Applicants: NATIONAL CANCER CENTER, Goyang-si (KR); KOREA RESEARCH INSTITUTE OF CHEMICAL TECHNOLOGY, Daejeon (KR)

(72) Inventors: Kyung Chae Jeong, Goyang-si (KR); Hwan Jung Lim, Daejeon (KR); Seong Jun Park, Daejeon (KR); Ho Kyung Seo, Paju-si (KR); Kyung Ohk Ahn, Gunpo-si (KR); Sang Jin Lee, Paju-si (KR); Eun Sook Lee, Gwacheon-si (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 722 days.

This patent is subject to a terminal disclaimer.

(21) Appl. No.: 16/321,631

(22) PCT Filed: Jul. 27, 2017

(86) PCT No.: PCT/KR2017/008106
§ 371 (c)(1),
(2) Date: Jan. 29, 2019

(87) PCT Pub. No.: WO2018/021849
PCT Pub. Date: Feb. 1, 2018

(65) Prior Publication Data
US 2021/0315879 A1    Oct. 14, 2021

(30) Foreign Application Priority Data

| Jul. 29, 2016 | (KR) | 10-2016-0097435 |
| Nov. 29, 2016 | (KR) | 10-2016-0159885 |
| Nov. 29, 2016 | (KR) | 10-2016-0159887 |
| Nov. 29, 2016 | (KR) | 10-2016-0159889 |
| Nov. 29, 2016 | (KR) | 10-2016-0159898 |
| Nov. 29, 2016 | (KR) | 10-2016-0159900 |
| Nov. 29, 2016 | (KR) | 10-2016-0159904 |
| Jul. 26, 2017 | (KR) | 10-2017-0094694 |

(51) Int. Cl.
*A61K 31/47* (2006.01)
*A61P 35/00* (2006.01)
*A61K 31/4709* (2006.01)

(52) U.S. Cl.
CPC .......... *A61K 31/47* (2013.01); *A61K 31/4709* (2013.01); *A61P 35/00* (2018.01)

(58) Field of Classification Search
CPC ...... A61K 31/47; A61K 31/4709; A61P 35/00
See application file for complete search history.

(56) References Cited

U.S. PATENT DOCUMENTS 8,106,071 B2    1/2012   Chung et al.

FOREIGN PATENT DOCUMENTS

| EP | 2 878 677 A1 | 6/2015 |
| JP | 3-223289 A | 10/1991 |
| KR | 10-2005-0110237 A | 11/2005 |
| KR | 10-2008-0077889 A | 8/2008 |
| KR | 10-2010-0123937 A | 11/2010 |
| WO | 2012/093741 A1 | 7/2012 |

OTHER PUBLICATIONS

Choi et al., "Isothiazole Ring Formation with Substituted 2-Alkylthio-3-acyl-4-quinolinone Using O-(Mesitylenesulfonyl)hydroxylamine (MSH)", Synlett 2003, No. 2, pp. 166-172, (2003).
Ebraheem et al., "Synthesis of new polysubstituted (pyrazoles, pyrimidines and quinolines) five and six-membered heterocycles: reaction of alpha,alpha-dioxoketene dithioacetals with nucleophiles", Tetrahedron Letters, vol. 51, pp. 3486-3492, (2010).
Jung et al., "Identification of 3-acyl-2-phenylamino-1,4-dihydroquinolin-4-one derivatives as inhibitors of the phosphatase SerB653 in Porphyromonas gingivalis, implicated in periodontitis", Bioorganic & Medicinal Chemistry Letters, vol. 22, pp. 2084-2088, (2012).
Jeong et al., "Intravesical Instillation of c-MYC Inhibitor KSI-3716 Suppresses Orthotopic Bladder Tumor Growth", The Journal of Urology, 2014, vol. 191, Issue 2, pp. 510-518.

*Primary Examiner* — Alicia L Otton
(74) *Attorney, Agent, or Firm* — Vorys, Sater, Seymour and Pease LLP; Mih Suhn Koh

(57) ABSTRACT

Provided is a method for treating or preventing cancer, containing, as an active ingredient, a compound having a specific chemical structure and an activity of inhibiting the formation of a c-Myc/Max/DNA complex, or a pharmaceutically acceptable salt thereof.

8 Claims, 3 Drawing Sheets

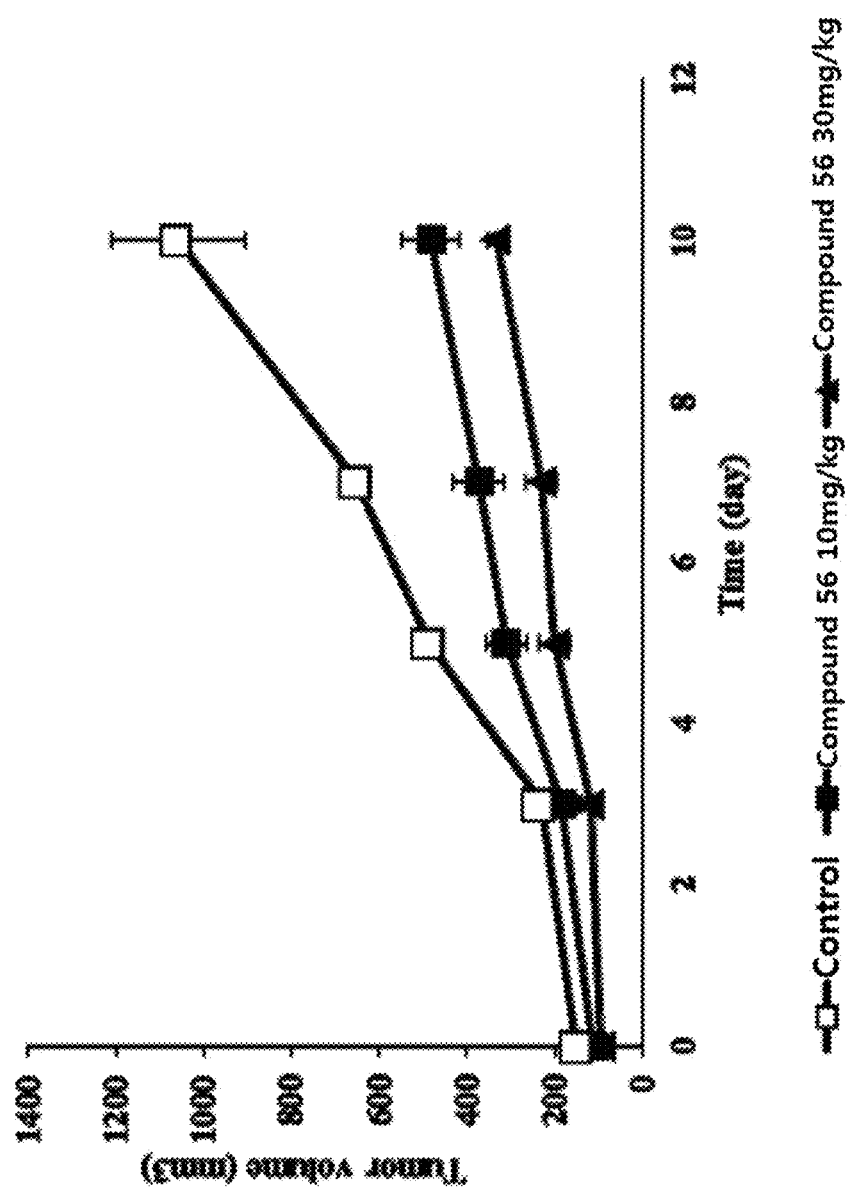
[Fig. 1]

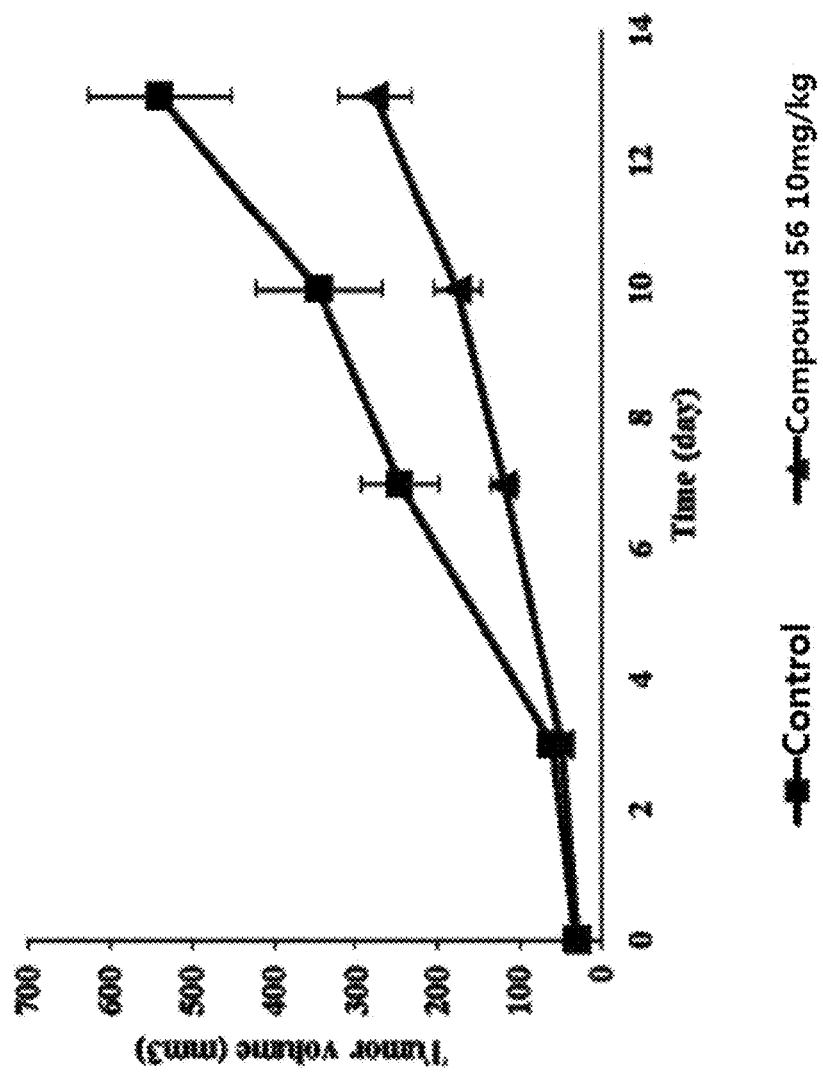
[Fig. 2]

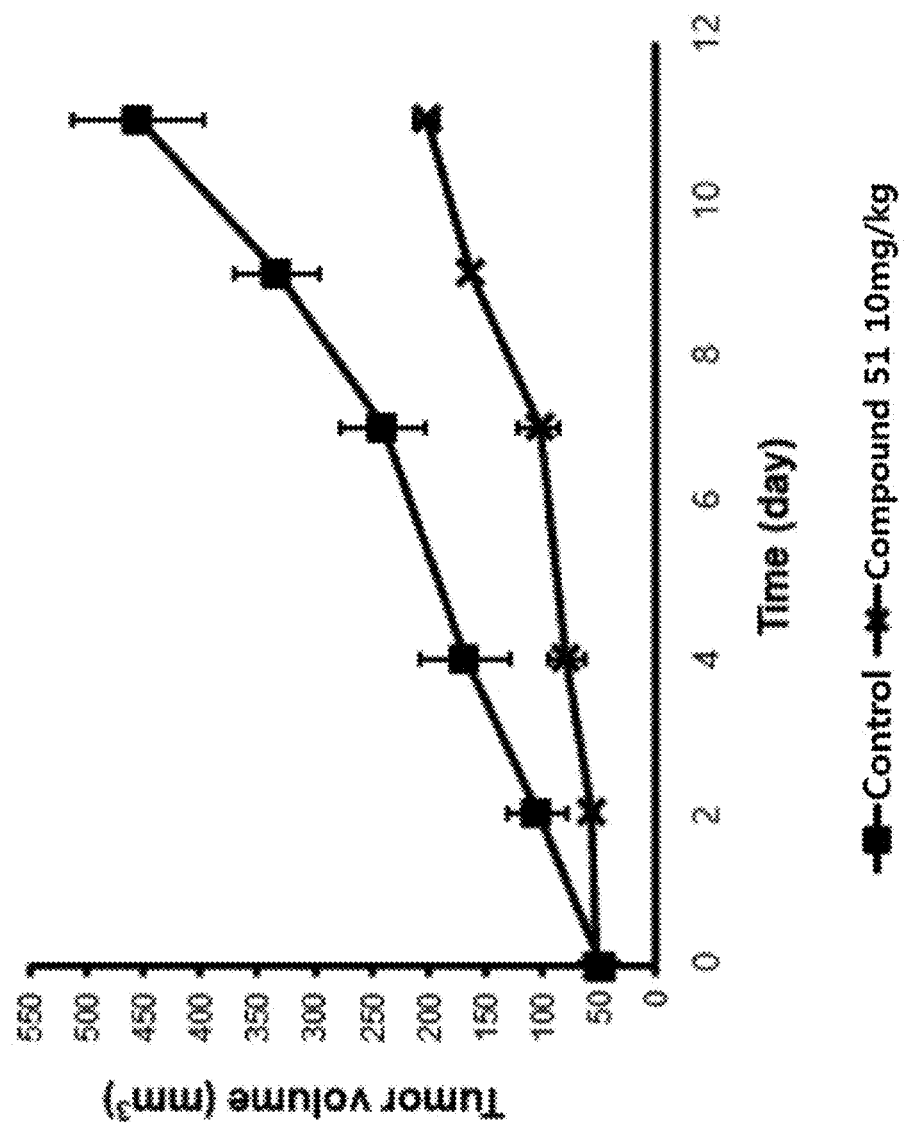
[Fig. 3]

ANTICANCER PHARMACEUTICAL COMPOSITION

CROSS-REFERENCE TO RELATED APPLICATION

This application is a 371 of PCT/KR2017/008106, filed Jul. 27, 2017, which claims the benefit of priority from Korean Patent Application No. 10-2016-0097435, filed Jul. 29, 2016, Korean Patent Application No. 10-2016-0159885, filed Nov. 29, 2016, Korean Patent Application No. 10-2016-0159887, filed Nov. 29, 2016, Korean Patent Application No. 10-2016-0159889, filed Nov. 29, 2016, Korean Patent Application No. 10-2016-0159898, filed Nov. 29, 2016, Korean Patent Application No. 10-2016-0159900, filed Nov. 29, 2016, Korean Patent Application No. 10-2016-0159904, filed Nov. 29, 2016 and Korean Patent Application No. 10-2017-0094694, filed Jul. 26, 2017, the contents of each of which are incorporated herein by reference in its entirety.

TECHNICAL FIELD

The present invention relates to a pharmaceutical composition for treating or preventing cancer, containing, as an active ingredient, a group of compounds having an activity of inhibiting the formation of a c-Myc/Max/DNA complex. The present invention relates to a method for treating or preventing a specific disease including cancer or a tumor by using the compound. That is, the present invention relates to a medical use of specific compounds for treating or preventing cancer or a tumor.

BACKGROUND ART c-myc is a proto-oncogene encoding the c-Myc oncoprotein regulating cell transformation, growth, differentiation, apoptosis, cell cycle progression, and the like.

Myc family proteins form a heterodimer with the basic/helix-loop-helix/leucine zipper (bHLHZip) domain of the Max protein, and the Myc/Max heterodimer binds to a specific DNA sequence (CACGTG) (E-box motif). Heterodimer formation with the Max protein and subsequent DNA binding of the heterodimer are steps required for transcriptional activation of target genes by c-Myc, and play important roles in promoting cell proliferation, malignant transformation, apoptosis and the like (see International Patent Publication No. WO2015/089180).

Abnormal expression of c-myc has been reported to be associated with various cancers including lung cancer, colorectal cancer, colon cancer, rectal cancer, breast cancer, bladder cancer, leukemia, myelogenous leukemia, lymphoma, small cell lung cancer, cervical carcinoma, osteosarcoma, glioblastoma, melanoma and the like (see Nature 1983 Nov. 10-16; 306(5939): 194-196; Cancer Res 1985 April; 45(4): 1823-1827; and Mol. BioSyst., 2010, 6: 1503-1509), and it has been reported that the expression of c-myc is elevated or deregulated in various human cancers and is associated with tumors (Oncogene, 1999, 18(19), 3004-16). Therefore, there has been much effort in developing anticancer agents or anti-tumor agents by regulating the expression of c-myc.

However, in development of related medicines, development of substances that directly inhibit the function of c-Myc has not been technically feasible, so that most attempts have been made to indirectly regulate the function of c-Myc. However, such indirect c-Myc inhibitors may cause many unexpected side effects. In particular, since c-Myc plays an important role in regulating cellular activity in the body, serious side effects may occur when c-Myc is not highly selective. In fact, development of many substances was discontinued due to toxicity problems. For example, a substance called JQ1 has recently been reported to be useful for myeloma treatment by indirectly regulating the expression of c-Myc (see Cell. 2011, 146(6): 904-917 and Blood. 2012, 120(14): 2843-2852), but it is known that development of JQ1 was discontinued due to serious side effects thereof.

Specifically, a motif responsible for binding of Myc and Max is the Leu-ZIP motif commonly found in general protein structures, and certain proteins that bind to the Leu-ZIP motif inhibit Myc/Max dimer formation, but have relatively low selectivity. That is, there is a high possibility that a side effect becomes a problem unless the selectivity is confirmed by selecting a motif having a structure unique to Myc/Max in the search process of the candidate substance. As an actual example, some c-Myc inhibitors exhibited low selectivity, inhibiting the activity of c-Jun/Fos transcription factors with similar structures. Accordingly, it is important to develop an inhibitor capable of selectively acting only on Myc/Max, and accordingly, rather than targeting inhibition of dimer formation, targeting inhibition of DNA complex formation of a c-Myc/Max dimer will give higher selectivity.

In addition, it is reported that c-Myc inhibitors can enhance the anticancer effect by combinatory administration with an anticancer agent having a different action mechanism (for example, "as an experimental result of Modeling Myc inhibition as a cancer therapy." Nature 2008, 455 (7213): 679-83, lung cancer still progresses when K-Ras alone inhibits lung cancer, but when K-Ras and Mcy simultaneously inhibit lung cancer, the lung cancer disappears.). Furthermore, the Myc inhibitor has been identified as an anticancer sensitizing agent which not only has a good anticancer effect, but also is effective for cancer resistant to cancer drugs.

Specifically, according to recent studies, when highly resistant hepatocellular carcinoma cells are treated with an anticancer agent (doxorubicin, 5-FU, and cisplatin) alone, the cancer cells are not killed, but when the carcinoma cells are treated with the anticancer agent and the Myc inhibitor, it was confirmed that the anticancer effect was explosively increased (see Anticancer Drugs, 2007. 18(2): p. 161-70). These study results suggest that it is possible to exhibit a high anticancer effect by administering the Myc inhibitor in combination with other anticancer agents.

A document Mol Pharm 2009, 6 (2): 627-33 discloses a combinatory administration of the c-Myc inhibitor with different anticancer agents. The document evaluated an increase in expression of an ABC transporter according to the overexpression of c-Myc in cancer cells. A mechanism in which resistance to most cytotoxic drugs conventionally used appears is known to be mainly caused by an ABC transporter which releases the anticancer agent to the outside of cancer cells.

In order to overcome this disadvantage, numerous companies have tried to develop an inhibitor of the ABC transporter, but many problems have been found in the clinical setting. According to recent study results, it has been confirmed that when c-Myc is overexpressed in cancer cells, the expression of the ABC transporter is increased, and accordingly, effects of the anticancer agent are weakened. Based on the study background, when the c-Myc inhibitor is administered in combination with an existing anticancer agent, it is expected to be able to overcome the resistance of the existing anticancer agent and maximize a synergistic effect.

Therefore, there is a need for the development of an inhibitor capable of directly inhibiting a feasible c-Myc action, and specifically, there is a need for the development of an inhibitor with high selectivity for c-Myc inhibitory activity and a low possibility of side effects.

DISCLOSURE

Technical Problem

As the present invention has been made to solve the aforementioned problems, the present inventors have synthesized compounds which have a high activity of inhibiting the formation of, particularly, a c-Myc/Max/DNA complex and a high selectivity for this inhibitory activity, and as a result, have a good effect of inhibiting cancer cells and reduced side effects other than the effect of inhibiting cancer cells and various compounds to secure the use thereof, and then carried out various evaluation experiments, thereby completing the present invention by finally confirming that the compounds of the present invention are suitable for the object of the present invention.

Accordingly, a problem to be solved by the present invention is to provide a pharmaceutical composition containing, as an active ingredient, a compound having an activity of inhibiting the formation of a c-Myc/Max/DNA complex, and a medical use thereof for treating or preventing cancer.

Another problem to be solved by the present invention is to provide a method for treating or alleviating cancer, comprising administering, to a patient in need of treatment, alleviation, or prevention of cancer, the compound according to the present invention, which inhibits the formation of a c-Myc/Max/DNA complex.

Still another problem to be solved is to provide a pharmaceutical composition containing, as an active ingredient, a compound capable of exhibiting a synergistic effect by being administered in combination with other anticancer agents, and a medical use thereof for treating or preventing cancer.

Yet another problem to be solved by the present invention is to provide a method for treating or alleviating cancer, comprising simultaneously or sequentially administering, to a patient in need of treatment, alleviation, or prevention of cancer, a compound inhibiting the formation of a c-Myc/Max/DNA complex, and an anticancer agent having a mechanism different from that of the compound.

Technical Solution

In order to solve the problems, in an aspect, the present invention provides a pharmaceutical composition for treating or preventing cancer, containing, as an active ingredient, a compound of the following Formula 1a or 1b, or a pharmaceutically acceptable salt thereof.

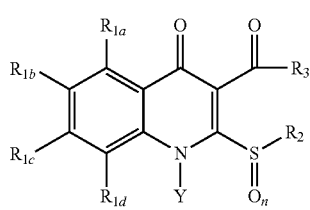

[Formula 1a]

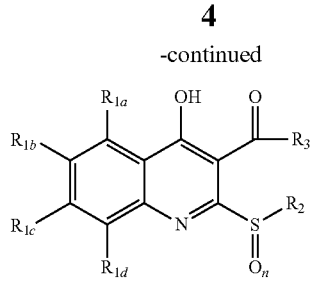

[Formula 1b]

In Formula 1, $R_{1a}$ to $R_{1d}$ are each independently hydrogen, a halogen, a $C_{1-6}$ alkyl, a $C_{1-6}$ haloalkyl, a $C_{1-6}$ hydroxyalkyl, a $C_{1-6}$ alkoxy, a $C_{1-6}$ haloalkoxy, a $C_{2-10}$ alkenyl, a $C_{2-10}$ haloalkenyl, a $C_{2-10}$ alkynyl, a $C_{2-10}$ haloalkynyl, a hydroxyl group, nitro, cyano, a $C_{1-6}$ alkoxycarbonyl, amino, a $C_{1-6}$ alkylamino, a di($C_{1-6}$ alkyl)amino, an amino($C_{1-6}$)alkyl, a ($C_{1-6}$)alkylamino($C_{1-6}$)alkyl, a $C_{1-6}$ alkanoyl, a $C_{3-7}$ cycloalkyl, an aryl, a heterocycle, or a heteroaryl, in which $R_{1a}$ to $R_{1d}$ may be each independently unsubstituted or one or more hydrogens may be optionally substituted, $R_2$ is hydrogen, a $C_{1-6}$ alkyl, a ($C_{1-6}$)alkoxy($C_{1-6}$)alkyl, a $C_{1-6}$ haloalkyl, a $C_{1-6}$ hydroxyalkyl, a $C_{1-6}$ alkoxy, a $C_{1-6}$ haloalkoxy, a $C_{2-10}$ alkenyl, a $C_{2-10}$ alkenyl carboxy, a $C_{2-10}$ haloalkenyl, a $C_{2-10}$ alkynyl, a $C_{2-10}$ haloalkynyl, a hydroxyl group, nitro, cyano, a $C_{1-6}$ alkoxycarbonyl, amino, a $C_{1-6}$ alkylamino, a $C_{1-6}$ cyanoalkyl, a di($C_{1-6}$ alkyl)amino, an amino($C_{1-6}$)alkyl, a ($C_{1-6}$)alkylamino($C_{1-6}$)alkyl, a $C_{1-6}$ alkanoyl, a $C_{3-7}$ cycloalkyl, a ($C_{1-6}$)alkyl($C_{3-7}$)cycloalkyl, an aryl, a ($C_{1-6}$)alkylaryl, a ($C_{1-6}$)haloalkylaryl, a ($C_{2-6}$)alkenylamide($C_{1-6}$)alkylalkoxy, a heterocycle, a ($C_{1-6}$)alkylheterocycle, a heteroaryl, or a ($C_{1-6}$)alkylheteroaryl, in which $R_2$ may be unsubstituted or optionally substituted, $R_3$ is a $C_{1-4}$ alkyl, an isoalkyl, a cycloalkyl, phenyl, or a $C_{1-4}$ haloalkyl, n is an integer from 0 to 2, and Y is hydrogen, an alkyl, a haloalkyl, —C(O)alkyl, —C(O)aryl, a sulfonylalkyl, a sulfonylaryl, an aryl, or an alkylaryl, in which the alkyl has 1 to 10 carbon atoms, preferably 1 to 4 carbon atoms, and the aryl may be unsubstituted or one or more hydrogens may be optionally substituted.

In an aspect, the present invention provides a pharmaceutical composition for treating or preventing cancer, containing, as an active ingredient, a compound of the following Formula 2a or 2b, or a pharmaceutically acceptable salt thereof.

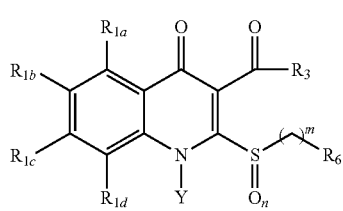

[Formula 2a]

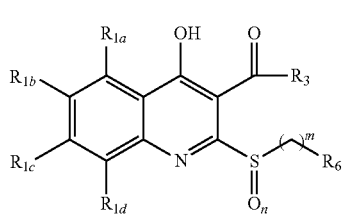

[Formula 2b]

In Formula 2, $R_{1a}$ to $R_{1d}$, $R_3$, n, and Y are as defined in Formula 1, m is an integer from 0 to 4, and $R_6$ is phenyl, oxazole, pyrazole, pyrrole, imidazole, thiazole, thiophene, pyridine, pyrimidine, furan, indole, benzopyrazole, benzothiazole, benzooxazole, isoxazole, benzoimidazole, 1,2,5-oxadiazole, pyrrolo[2,3-b]pyridine, or benzothiophene, which may be unsubstituted or may be optionally substituted with one or more of hydrogen, a $C_{1-6}$ alkyl, a $C_{1-6}$ haloalkyl, a $C_{1-6}$ alkoxy, a halogen or one or more of hydrogen, phenyl, oxazole, pyrazole, pyrrole, imidazole, thiazole, thiophene, pyridine, pyrimidine, furan, indole, benzopyrazole, benzothiazole, benzooxazole, isoxazole, benzoimidazole, or benzothiophene or may be substituted with unsubstituted phenyl.

In an aspect, the present invention provides a pharmaceutical composition for treating or preventing cancer, containing, as an active ingredient, a compound of the following Formula 3a or 3b, or a pharmaceutically acceptable salt thereof.

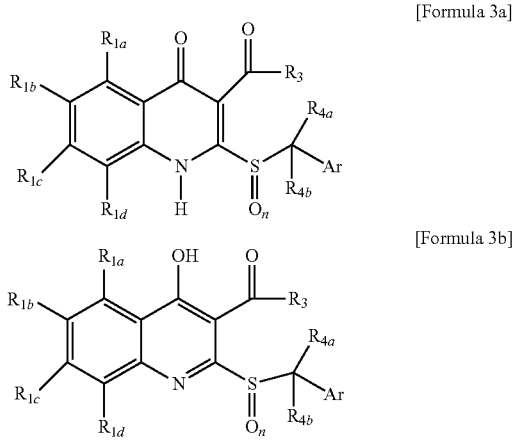

[Formula 3a]

[Formula 3b]

In Formula 3, $R_{1a}$ to $R_{1d}$, $R_3$, and n are as defined in Formula 1, $R_{4a}$ and $R_{4b}$ are each independently hydrogen, a halogen, a $C_{1-4}$ alkyl, a $C_{1-4}$ haloalkyl, or a $C_{1-4}$ alkyl in which one or more hydrogens are substituted with substituents other than a halogen, Ar is phenyl, a 5 to 6-membered heteroaryl, or an 8 to 12-membered biheteroaryl, and the heteroaryl includes at least one or more of N, S, and O in the ring, Ar may be unsubstituted or may be optionally substituted with one or more of a halogen, a $C_{1-6}$ alkyl, a $C_{1-6}$ alkylthio, a $C_{1-6}$ haloalkyl, a $C_{1-6}$ haloalkylthio, a $C_{1-6}$ alkoxy, a $C_{1-6}$ haloalkoxy, a $C_{2-10}$ alkenyl, a $C_{2-10}$ haloalkenyl, a $C_{2-10}$ alkynyl, a $C_{2-10}$ haloalkynyl, a hydroxyl group, COOH, nitro, cyano, a $C_{1-6}$ alkoxycarbonyl, amino, a $C_{1-6}$ alkylamino, a di($C_{1-6}$ alkyl)amino, an amino($C_{1-6}$)alkyl, a ($C_{1-6}$) alkylamino($C_{1-6}$) alkyl, a ($C_{1-6}$)alkoxy($C_{1-6}$)alkylamino, a ($C_{1-6}$)alkylamino($C_{1-6}$) alkylamino, a $C_{1-6}$ alkanoyl, $SF_5$, $S(O)CF_3$, $SCF_3$, $NHC(=O)CH_3$, $C(=O)NHCH_3$, $NHSO_2CH_3$, a $C_{3-7}$ cycloalkyl, an aryl, benzoyl, a heterocycle, a heteroaryl, phenyl, oxazole, pyrazole, pyrrole, imidazole, thiazole, thiophene, pyridine, pyrimidine, furan, indole, benzopyrazole, benzothiazole, benzooxazole, isoxazole, benzoimidazole, or benzothiophene, and the substituents of Ar may be unsubstituted or may be substituted with one or more selected from the group consisting of $CF_3$, a halogen, a $C_{1-3}$ alkyl, a $C_{1-3}$ haloalkyl, a hydroxyl group, COOH, nitro, cyano, amino, a di($C_{1-3}$ alkyl)amino, $NHC(=O)CH_3$ and $C(=O)NHCH_3$.

In another aspect, the present invention provides a pharmaceutical composition for treating or preventing cancer, containing a compound of Formula 1, 2, or 3 or a pharmaceutically acceptable salt thereof, and a pharmaceutically acceptable carrier or additive.

In various aspects, the pharmaceutical composition may further contain one or more additional pharmaceutically active ingredients.

In still another aspect, the present invention provides a method for treating a disease, including a step of administering, to a subject, a therapeutically effective amount of a compound of Formula 1, 2, or 3 or a pharmaceutically acceptable salt thereof, in which the disease to be treated is, but not limited to, cancer, neoplasia, or tumor including lung cancer (including small cell lung cancer and non-small cell lung cancer), colorectal cancer, colon cancer, rectal cancer, breast cancer, prostate cancer, bladder cancer, blood cancer, leukemia, myelogenous leukemia, lymphoma, cervical carcinoma, osteosarcoma, glioblastoma, melanoma, pancreatic cancer, gastric cancer, liver cancer, renal cancer, gallbladder cancer, bile duct cancer, esophageal cancer, and the like. That is, the present invention provides a medical use of a compound of Formula 1, 2, or 3, or a pharmaceutically acceptable salt thereof for treating or preventing the disease.

In various aspects, the method includes a step of administering a complex (combination) of the compound of the present invention or a salt thereof with at least one of other pharmaceutically active compounds. That is, the present invention provides a medical use of a complex consisting of (a) the compound according to the present invention or a pharmaceutically acceptable salt thereof and (b) another active agent for treating or preventing the disease or disorder.

Advantageous Effects

The present invention provides a pharmaceutical composition containing, as an active ingredient, a compound capable of exhibiting various pharmacological activities by inhibiting the formation of a c-Myc/Max/DNA complex, a medical use (particularly, an anticancer use) thereof, and a treatment method including administering the same to a subject in need of treatment or prevention. The compound according to the present invention or a pharmaceutically acceptable salt thereof can exhibit an excellent medical effect due to excellent safety and high selectivity in terms of inhibiting the formation of the c-Myc/Max/DNA complex.

DESCRIPTION OF DRAWINGS

FIG. 1 is a graph showing the results of confirming the effect of inhibiting tumor growth after Compound 56 is intraperitoneally administered three times a week in an animal model using a human lung cancer cell line (NCI-H1299).

FIG. 2 is a graph showing the results of confirming the effect of inhibiting tumor growth after Compound 56 is intraperitoneally administered twice a week in an animal model using a human prostate cancer cell line (DU145).

FIG. 3 is a graph showing the results of confirming the effect of inhibiting tumor growth after Compound 51 is orally administered three times a week in an animal model using a human lung cancer cell line (NCI-H1299).

MODES OF THE INVENTION

The present invention provides a pharmaceutical composition for treating or preventing cancer, containing, as an active ingredient, a compound having a structure of the following Formula 1 (1a or 1b), or a pharmaceutically acceptable salt thereof.

[Formula 1a]

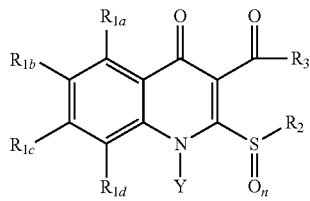

[Formula 1b]

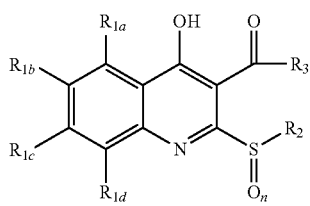

In Formula 1, $R_{1a}$ to $R_{1d}$ are each independently hydrogen, a halogen, a $C_{1-6}$ alkyl, a $C_{1-6}$ haloalkyl, a $C_{1-6}$ hydroxyalkyl, a $C_{1-6}$ alkoxy, a $C_{1-6}$ haloalkoxy, a $C_{2-10}$ alkenyl, a $C_{2-10}$ haloalkenyl, a $C_{2-10}$ alkynyl, a $C_{2-10}$ haloalkynyl, a hydroxyl group, nitro, cyano, a $C_{1-6}$ alkoxycarbonyl, amino, a $C_{1-6}$ alkylamino, a di($C_{1-6}$ alkyl)amino, an amino($C_{1-6}$)alkyl, a ($C_{1-6}$)alkylamino($C_{1-6}$)alkyl, a $C_{1-6}$ alkanoyl, a $C_{3-7}$ cycloalkyl, an aryl, a heterocycle, or a heteroaryl, in which $R_{1a}$ to $R_{1d}$ may be each independently unsubstituted or optionally substituted, $R_2$ is hydrogen, a $C_{1-6}$ alkyl, a ($C_{1-6}$)alkoxy($C_{1-6}$)alkyl, a $C_{1-6}$ haloalkyl, a $C_{1-6}$ hydroxyalkyl, a $C_{1-6}$ alkoxy, a $C_{1-6}$ haloalkoxy, a $C_{2-10}$ alkenyl, a $C_{2-10}$ alkenyl carboxy, a $C_{2-10}$ haloalkenyl, a $C_{2-10}$ alkynyl, a $C_{2-10}$ haloalkynyl, a hydroxyl group, nitro, cyano, a $C_{1-6}$ alkoxycarbonyl, amino, a $C_{1-6}$ alkylamino, a $C_{1-6}$ cyanoalkyl, a di($C_{1-6}$ alkyl)amino, an amino($C_{1-6}$)alkyl, a ($C_{1-6}$)alkylamino($C_{1-6}$)alkyl, a $C_{1-6}$ alkanoyl, a $C_{3-7}$ cycloalkyl, a ($C_{1-6}$)alkyl($C_{3-7}$)cycloalkyl, an aryl, a ($C_{1-6}$)alkylaryl, a ($C_{1-6}$)haloalkylaryl, a ($C_{2-6}$)alkenylamide($C_{1-6}$)alkylalkoxy, a heterocycle, a ($C_{1-6}$) alkylheterocycle, a heteroaryl, or a ($C_{1-6}$)alkylheteroaryl, in which $R_2$ may be unsubstituted or optionally substituted, $R_3$ is a $C_{1-4}$ alkyl, an isoalkyl, a cycloalkyl, phenyl, or a $C_{1-4}$ haloalkyl, n is an integer from 0 to 2, and Y is hydrogen, an alkyl, a haloalkyl, —C(O)alkyl, —C(O) aryl, a sulfonylalkyl, a sulfonylaryl, an aryl, or an alkylaryl, in which the alkyl has 1 to 10 carbon atoms, preferably 1 to 4 carbon atoms, and the aryl may be unsubstituted or optionally substituted.

In another aspect, the present invention provides a pharmaceutical composition for treating or preventing cancer, containing, as an active ingredient, a compound having a structure of the following Formula 2 (2a or 2b), or a pharmaceutically acceptable salt thereof.

[Formula 2a]

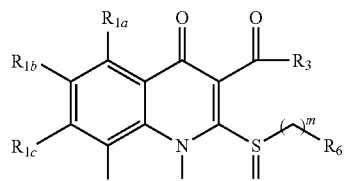

[Formula 2b]

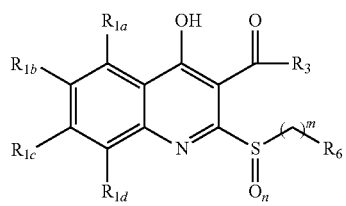

In Formula 2, $R_{1a}$ to $R_{1d}$, $R_3$, n, and Y are as defined in Formula 1, m is an integer from 0 to 4, and $R_6$ is phenyl, oxazole, pyrazole, pyrrole, imidazole, thiazole, thiophene, pyridine, pyrimidine, furan, indole, benzopyrazole, benzothiazole, benzooxazole, isoxazole, benzoimidazole, 1,2,5-oxadiazole, pyrrolo[2,3-b]pyri dine, or benzothiophene, which may be unsubstituted or may be optionally substituted with one or more of hydrogen, a $C_{1-6}$ alkyl, a $C_{1-6}$ haloalkyl, a $C_{1-6}$ alkoxy, a halogen or one or more of hydrogen, phenyl, oxazole, pyrazole, pyrrole, imidazole, thiazole, thiophene, pyridine, pyrimidine, furan, indole, benzopyrazole, benzothiazole, benzooxazole, isoxazole, benzoimidazole, or benzothiophene or may be substituted with unsubstituted phenyl.

In still another aspect, the present invention provides a pharmaceutical composition for treating or preventing cancer, containing, as an active ingredient, a compound having a structure of the following Formula 3 (3a or 3b), or a pharmaceutically acceptable salt thereof.

[Formula 3a]

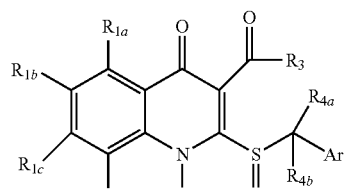

[Formula 3b]

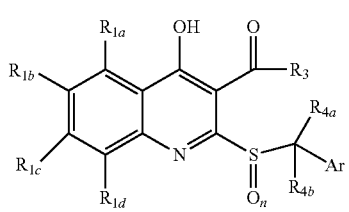

In Formula 3, $R_{1a}$ to $R_{1d}$, $R_3$, and n are as defined in Formula 1, $R_{4a}$ and $R_{4b}$ are each independently hydrogen, a halogen, a $C_{1-4}$ alkyl, a $C_{1-4}$ haloalkyl, or a $C_{1-4}$ alkyl in which one or more hydrogens are substituted with substituents other than a halogen, Ar is phenyl, a 5 to 6-membered heteroaryl, or an 8 to 12-membered biheteroaryl, and the heteroaryl includes at least one or more of N, S, and O in the ring, Ar may be unsubstituted or may be optionally substituted with one or more of a halogen, a $C_{1-6}$ alkyl, a $C_{1-6}$ alkylthio, a $C_{1-6}$ haloalkyl, a $C_{1-6}$ haloalkylthio, a $C_{1-6}$ alkoxy, a $C_{1-6}$ haloalkoxy, a $C_{2-10}$ alkenyl, a $C_{2-10}$ haloalkenyl, a $C_{2-10}$ alkynyl, a $C_{2-10}$ haloalkynyl, a hydroxyl group, COOH, nitro, cyano, a $C_{1-6}$ alkoxycarbonyl, amino, a $C_{1-6}$ alkylamino, a di($C_{1-6}$ alkyl)amino, an amino($C_{1-6}$)alkyl, a ($C_{1-6}$)alkylamino($C_{1-6}$)alkyl, a ($C_{1-6}$)alkoxy($C_{1-6}$)alkylamino, a ($C_{1-6}$)alkylamino($C_{1-6}$) alkylamino, a $C_{1-6}$ alkanoyl, $SF_5$, $S(O)CF_3$, $SCF_3$, $NHC(=O)CH_3$, $C(=O)NHCH_3$, $NHSO_2CH_3$, a $C_{3-7}$ cycloalkyl, an aryl, benzoyl, a heterocycle, a heteroaryl, phenyl, oxazole, pyrazole, pyrrole, imidazole, thiazole, thiophene, pyridine, pyrimidine, furan, indole, benzopyrazole, benzothiazole, benzooxazole, isoxazole, benzoimidazole, or benzothiophene, and the substituents of Ar may be unsubstituted or may be substituted with one or more selected from the group consisting of $CF_3$, a halogen, a $C_{1-3}$ alkyl, a $C_{1-3}$ haloalkyl, a hydroxyl group, COOH, nitro, cyano, amino, a di($C_{1-3}$ alkyl)amino, $NHC(=O)CH_3$ and $C(=O)NHCH_3$.

The following terms used in the present specification are defined as follows.

In the present specification, the terms "substituent", "radical", "group", "moiety", and "fragment" may be used interchangeably.

As used herein, the term "patient" refers to an animal (for example, a cow, a horse, a sheep, a pig, a chicken, a turkey, a quail, a cat, a dog, a mouse, a rat, a rabbit, or a guinea pig), preferably a mammal such as a non-primate and a primate (for example, a monkey and a human), and most preferably a human.

As used herein, the term "alkyl" refers to (when the number of carbon atoms is not particularly limited) a saturated, linear or branched, non-cyclic hydrocarbon having 1 to 10 carbon atoms. "Lower alkyl" refers to a linear or branched alkyl having 1 to 4 carbon atoms. A representative saturated linear alkyl includes -methyl,-ethyl, -n-propyl, -n-butyl, -n-pentyl, -n-hexyl, -n-heptyl, -n-octyl, -n-nonyl, and -n-decyl, whereas the saturated branched alkyl includes -isopropyl, -sec-butyl, -isobutyl, -tert-butyl, isopentyl, 2-methylhexyl, 3-methylbutyl, 2-methylpentyl, 3-methylpentyl, 4-methylpentyl, 3-methylhexyl, 2-methylpentyl, 3-methylpentyl, 4-methylpentyl, 4-methylhexyl, 5-methylhexyl, 2,3-dimethylbutyl, 2,3-dimethylpentyl, 2,4-dimethylpentyl, 2,3-dimethylpentyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, and 3,3-diethylhexyl.

The case where "$C_{1-6}$" is described in the present specification means that the number of carbon atoms is 1 to 6. For example, a $C_{1-6}$ alkyl refers to an alkyl having 1 to 6 carbon atoms.

As used herein, the term "alkenyl" refers to a saturated, linear or branched, non-cyclic hydrocarbon including 2 to 10 carbon atoms and at least one carbon-carbon double bond. Representative linear and branched ($C_2$-$C_{10}$) alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, and -3-decenyl. These alkenyl groups may be optionally substituted. "Cyclic alkylidene" is a ring having 3 to 8 carbon atoms and includes at least one carbon-carbon double bond, and the ring may have 1 to 3 heteroatoms.

As used herein, the term "alkynyl" refers to a saturated, linear or branched, non-cyclic hydrocarbon having 2 to 10 carbon atoms and including at least one carbon-carbon triple bond. A representative linear or branched ($C_2$-$C_{10}$) alkynyl includes -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynl, -1-decynyl, -2-decynyl, and -9-decynyl. These alkynyl groups may be optionally substituted.

As used herein, the terms "halogen" and "halo" refer to fluorine, chlorine, bromine, or iodine.

As used herein, the terms "haloalkyl", "haloalkoxy", "haloalkenyl" or "haloalkynyl" refer to an alkyl group, an alkoxy group, an alkenyl group, or an alkynyl group, in which one or more hydrogen atoms are substituted with a halogen atom, respectively. For example, the haloalkyl includes —$CF_3$, —$CHF_2$, —$CH_2F$, —$CBr_3$, —$CHBr_2$, —$CH_2Br$, —$CCl_3$, —$CHCl_2$, —$CH_2Cl$, —$CI_3$, —$CHI_2$, —$CH_2I$, —$CH_2$—$CF_3$, —$CH_2$—$CHF_2$, —$CH_2$—$CH_2F$, —$CH_2$—$CBr_3$, —$CH_2$—$CHBr_2$, —$CH_2$—$CH_2Br$, —$CH_2$—$CCl_3$, —$CH_2$—$CHCl_2$, —$CH_2$—$CH_2Cl$, —$CH_2$—$CI_3$, —$CH_2$—$CHI_2$, —$CH_2$—$CH_2I$, and those similar to the groups. Here, the alkyl and the halogen are as described above.

As used herein, the term "alkanoyl" or "acyl" refers to a —C(O)alkyl group including —$C(O)CH_3$, —$C(O)CH_2CH_3$, —$C(O)(CH_2)_2CH_3$, —$C(O)(CH_2)_3CH_3$, —$C(O)(CH_2)_4CH_3$, —$C(O)(CH_2)_5CH_3$, and those similar to the groups, and here, the alkyl is as described above.

As used herein, the term "alkanoyloxy" or "acyloxy" refers to a —OC(O)alkyl group including $OC(O)CH_3$, —$OC(O)CH_2CH_3$, —$OC(O)(CH_2)_2CH_3$, —$OC(O)(CH_2)_3CH_3$, —$OC(O)(CH_2)_4CH_3$, —$OC(O)(CH_2)_5CH_3$, and those similar to the groups, and here, the alkyl is as described above.

As used herein, the term "alkoxy" refers to —O-(alkyl) including —$OCH_3$, —$OCH_2CH_3$, —$O(CH_2)_2CH_3$, —$O(CH_2)_3CH_3$, —$O(CH_2)_4CH_3$, —$O(CH_2)_5CH_3$, and those similar to the groups, and here, the alkyl is as described above.

As used herein, the term "lower alkoxy" refers to —O-(lower alkyl), and here, the lower alkyl is as defined above.

As used herein, the term "aryl" refers to a carbocyclic aromatic group containing 5 to 10 cyclic atoms. Representative examples thereof include phenyl, tolyl, xylyl, naphthyl, tetrahydronaphthyl, anthracenyl, fluorenyl, indenyl, azylenyl, and the like, but are not limited thereto. The carbocyclic aromatic group may be optionally substituted.

The term "aryloxy" is RO—, and R is the aryl defined above. "Arylthio" is RS—, and R is the aryl defined above.

As used herein, the term "cycloalkyl" refers to a monocyclic or polycyclic saturated ring which has carbon and hydrogen atoms and does not have a carbon-carbon multiple bond. Examples of the cycloalkyl group include a ($C_3$-$C_7$) cycloalkyl (for example, cyclopropyl, cyclobutyl, cyclopentyl, cyclohexyl, and cycloheptyl), but are not limited thereto. The cycloalkyl group may be optionally substituted. In an example, the cycloalkyl group is a monocyclic or bicyclic ring (cycle).

As used herein, the term "mono-alkylamino" refers to —NH(alkyl) including —$NHCH_3$, —$NHCH_2CH_3$, —NH (CH₂)₂CH₃, —NH(CH₂)₃CH₃, —NH(CH₂)₄CH₃, —NH(CH₂)₅CH₃, and those similar to the groups, and here, the alkyl is as described above.

As used herein, the term "di-alkylamino" refers to —N(alkyl)(alkyl) including —N(CH₃)₂, —N(CH₂CH₃)₂, —N((CH₂)₂CH₃)₂, —N(CH₃)(CH₂CH₃), and those similar to the groups, and here, each alkyl is independently the alkyl defined above.

As used herein, the term "alkylamino" is a concept including the mono-alkylamino and the di-alkylamino defined above.

As used herein, the terms "carboxyl" and "carboxy" refer to —COOH.

As used herein, the term "aminoalkyl" refers to -(alkyl)-NH₂ including —CH₂—NH₂, —(CH₂)₂—NH₂, —(CH₂)₃—NH₂, —(CH₂)₄—NH₂, —(CH₂)₅—NH₂, and those similar to the groups, and here, the alkyl is as described above.

As used herein, the term "mono-alkylaminoalkyl" refers to -(alkyl)-NH(alkyl) including —CH₂—NH—CH₃, —CH₂—NHCH₂CH₃, —CH₂—NH(CH₂)₂CH₃, —CH₂—NH(CH₂)₃CH₃, —CH₂—NH(CH₂)₄CH₃, —CH₂—NH(CH₂)₅CH₃, —(CH₂)₂—NH—CH₃, and those similar to the groups, and here, each alkyl is independently the alkyl defined above.

As used herein, "heteroaryl" refers to a 5- to 10-membered aromatic heterocyclic ring having at least one heteroatom selected from the group consisting of nitrogen, oxygen, and sulfur, and including at least one carbon atom including a mono- and bicyclic ring system. A representative heteroaryl is triazolyl, tetrazoyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, oxetanyl, azepinyl, piperazinyl, morpholinyl, dioxanyl, thiethanyl and oxazolyl.

As used herein, "heterocycle (hetero ring)" refers to a saturated or unsaturated 5- to 7-membered monocyclic or 7- to 10-membered bicyclic or heterocyclic ring containing 1 to 4 heteroatoms independently selected from nitrogen, oxygen, and sulfur, and here, nitrogen and sulfur heteroatoms may be optionally oxidized, the nitrogen heteroatom may be optionally quaternized, and a part of the heterocycle includes a bicyclic ring fused to the benzene ring. The heterocycle may be attached by a heteroatom or carbon atom. The heterocycle includes the heteroaryl defined above. A representative heterocycle includes morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, tetrahydropyrimidinyl, tetrahydrothiophenyl, and tetrahydrothiopyranyl.

"Heterocycle fused to phenyl" refers to a heterocycle attached to two adjacent carbon atoms of a phenyl ring, and here, the heterocycle is as defined above.

As used herein, the term "hydroxyalkyl" refers to an alkyl including —CH₂OH, —CH₂CH₂OH, —(CH₂)₂CH₂OH, —(CH₂)₃CH₂OH, —(CH₂)₄CH₂OH, —(CH₂)₅CH₂OH, —CH(OH)—CH₃, —CH₂CH(OH)CH₃, and those similar to the groups, in which one or more hydrogen atoms are substituted with hydroxy, and here, the alkyl is as defined above.

As used herein, the term "sulfonyl" refers to —SO₃H.

As used herein, the term "sulfonylalkyl" refers to —SO₂-(alkyl) including —SO₂—CH₃, —SO₂—CH₂CH₃, —SO₂—(CH₂)₂CH₃, —SO₂—(CH₂)₃CH₃, —SO₂—(CH₂)₄CH₃, and —SO₂—(CH₂)₅CH₃, and here, the alkyl is as described above.

As used herein, the term "sulfinylalkyl" refers to —SO-(alkyl) including —SO—CH₃, —SO—CH₂CH₃, —SO—(CH₂)₂CH₃, —SO—(CH₂)₃CH₃, —SO—(CH₂)₄CH₃, —SO—(CH₂)₅CH₃, and those similar to the groups, and here, the alkyl is as described above.

"Thioalkyl" includes —S—CH₃, —S—CH₂CH₃, —S—(CH₂)₂CH₃, —S—(CH₂)₃CH₃, —S—(CH₂)₄CH₃, —S—(CH₂)₅CH₃, and those similar to the groups, and here, the alkyl is as described above.

As used herein, the term "substituted" means that the hydrogen atom of the moiety (for example, alkyl, aryl, heteroaryl, heterocycle or cycloalkyl) to be substituted is replaced with a substituent. In one embodiment, each carbon atom of the substituted group is not substituted with two or more substituents. In another embodiment, each carbon atom of the substituted group is not substituted with one or more substituents. In the case of a keto substituent, two hydrogen atoms are substituted with oxygen attached to carbon by a double bond. Unless otherwise specified with respect to a substituent, a halogen, hydroxyl, (lower) alkyl, haloalkyl, mono- or di-alkylamino, aryl, heterocycle, —NO₂, —NR$_a$R$_b$, —NR$_a$C(=O)R$_b$, —NR$_a$C(=O)NR$_a$R$_b$, —NR$_a$C(=O)OR$_b$, —NR$_a$SO₂R$_b$, —OR$_a$, —CN, —C(=O)Ra, —C(=O)OR$_a$, —C(=O)NR$_a$R$_b$, —OC(=O)R$_a$, —OC(=O)OR$_a$, —OC(=O)NR$_a$R$_b$, —NR$_a$SO₂R$_b$, —PO₃R$_a$, —PO(OR$_a$)(OR$_b$), —SO₂R$_a$, —S(O)R$_a$, —SO(NR$_a$)R$_b$ (for example, sulfoximine), —S(NR$_a$)R$_b$ (for example, sulfilimine) and —SR$_a$ may be used as substituents of the present invention, and here, R$_a$ and R$_b$ are the same or different and are each independently hydrogen, a halogen, amino, an alkyl, an alkoxyalkyl, a haloalkyl, an aryl or a heterocycle, or R$_a$ and R$_b$ may be in the form of a heterocycle as in the attached nitrogen atoms. Here, R$_a$ and R$_b$ may be plural depending on the bonded atom.

As used herein, "basic structure of quinoline" refers to the following structure.

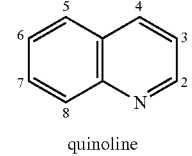

quinoline

In the present invention, "pharmaceutically acceptable salts" include salts of active compounds prepared from relatively non-toxic acids and bases depending on particular substituents found in the compounds mentioned herein. When the compounds of the present invention include relatively acidic functionality, base addition salts may be obtained by bringing the neutral forms of the compounds into contact with a sufficient amount of a desired base in a pure or suitable inert solvent. Examples of the pharmaceutically acceptable base addition salts include sodium, potassium, calcium, ammonium, organic amino or magnesium salts or similar salts. When the compounds of the present invention include relatively basic functionality, acid addition salts may be obtained by bringing the neutral forms of the compounds into contact with a sufficient amount of a desired acid in a pure or suitable inert solvent. Examples of the pharmaceutically acceptable acid addition salts include not only salts derived from relatively non-toxic organic acids including acetic acid, propionic acid, isobutylic acid, oxalic acid, maleic acid, malonic acid, benzoic acid, succinic acid, suberic acid, fumaric acid, mandelic acid, phthalic acid, benzenesulfonic acid, p-tolylsulfonic acid, citric acid, tartaric acid, methanesulfonic acid, and analogs thereof, but also hydrogen chloride, hydrogen bromide, nitric acid, carbonic acid, monohydrogen carbonic acid, phosphoric acid, monohydrogen phosphoric acid, dihydrogen phosphoric acid, sulfuric acid, monohydrogensulfuric acid, hydrogen iodide or phosphorous acid and analogs thereof. In addition, the pharmaceutically acceptable acid addition salts include salts of amino acids such as arginate and analogs thereof and analogs of organic acids such as glucuronic or galacturonic acids and analogs thereof (for example, Berge et al. (1977) J. Pharm. Sci. 66: 1-19). Certain compounds of the present invention have both basic and acidic functionalities to convert the compounds into base or acid addition salts. Other examples of the salts are disclosed in documents, for example, *Remington's Pharmaceutical Sciences*, 18$^{th}$ eds., Mack Publishing, Easton Pa. (1990) or *Remington: The Science and Practice of Pharmacy*, 19$^{th}$ eds., Mack Publishing, Easton Pa. (1995) known in the art to which the present invention pertains.

As used herein, "effective amount" refers to an amount of the compounds of the present invention sufficient to destroy, modify, control or eliminate primary, localized or metastatic cancer cells or cancer tissues; to slow or minimize the spread of cancer; or to provide therapeutic benefits in treatment or management of cancer, neoplastic diseases, or tumors. "Effective amount" also refers to an amount of the compounds of the present invention sufficient to cause the apoptosis of cancer or neoplastic cells. "Effective amount" also refers to an amount of the compounds sufficient to inhibit or reduce the formation of a c-Myc/Max/DNA complex either in vitro or in vivo.

As used herein, "inhibition of the formation of the c-Myc/Max/DNA complex" means that, when compared to cells that are not brought into contact with the compounds of the present invention, the amount of c-Myc/Max/DNA complexes is decreased or the degree of binding of the c-Myc/Max heterodimer to DNA is inhibited or delayed in cells brought into contact with the compounds of the present invention.

As used herein, "preventive effective amount" refers to an amount of the compounds of the present invention sufficient to inhibit cancer development in patients including patients susceptible to the recurrence, or spread of cancer, susceptible to cancer or patients previously exposed to a carcinogen, but are not limited thereto.

As used herein, the term "neoplastic" refers to an abnormal growth of cells or tissues (for example, a boil) that may be benign or cancerous.

As used herein, "prevention" includes preventing the recurrence, spread or onset of cancer in a patient.

As used herein, "treatment" includes eradication, removal, modification, or control of primary, localized or metastatic cancer tissues; and refers to minimizing or delaying the spread of cancer.

As used herein, the term "the compounds of the present invention" refers to compounds corresponding to each of Formula 1 (1a and 1b), Formula 2 (2a and 2b) and Formula 3 (3a and 3b), and also includes clathrates, hydrates, solvates, or polymorphs thereof. In addition, the term "the compounds of the present invention" also includes pharmaceutically acceptable salts of the compounds of the present invention, when pharmaceutically acceptable salts thereof are not mentioned. In one embodiment, the compounds of the present invention may be present as stereomerically pure compounds (for example, compounds that are substantially free of other stereoisomers (for example, 85% ee or more, 90% ee or more, 95% ee or more, 97% ee or more, or 99% ee or more)). That is, when compounds of Formula 1, 2, or 3 according to the present invention or salts thereof are tautomeric isomers and/or stereoisomers (for example, geometrical isomers and conformational isomers), isolated isomers thereof and respective mixtures thereof are also within the scope of the compounds of the present invention. When the compounds of the present invention or salts thereof have asymmetric carbons in the structure thereof, optically active compounds and racemic mixtures thereof are also within the scope of the compounds of the present invention. For example, as shown in the following scheme, when the compounds of the present invention have a sulfoxide(SOR) structure, the compounds may have chirality. The R and S forms of these isomers are included in the compounds of the present invention, and the mixtures of the R and S forms are also included within the scope of the compounds of the present invention.

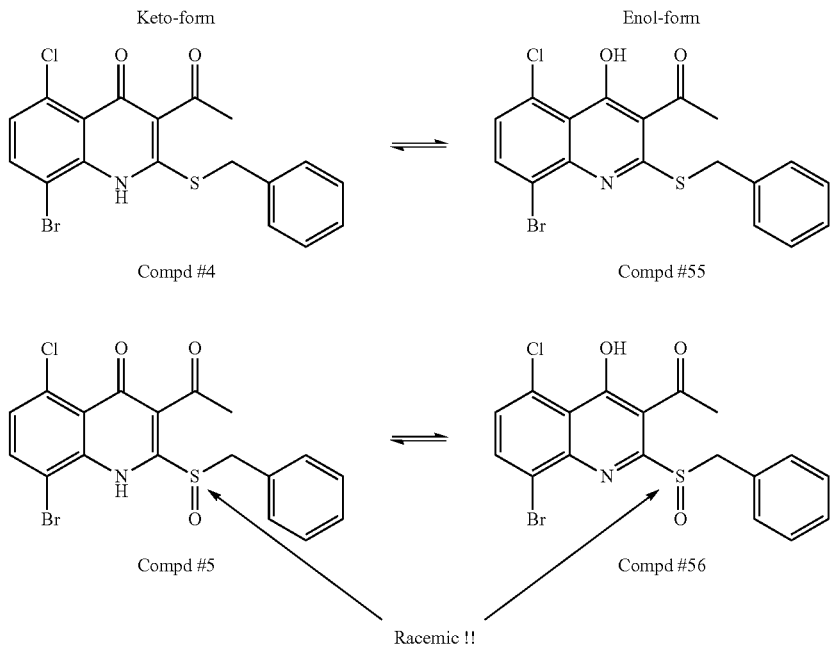

[Scheme 1]

Furthermore, as shown in Scheme 1, the compounds of the present invention may be present either in keto or enol form, both of which are included within the scope of the compounds of the present invention.

When used herein, the term "polymorph" refers to solid crystalline forms of the compounds of the present invention or complexes thereof. Different polymorphs of the same compound exhibit different physical, chemical and/or spectral characteristics. Differences in physical characteristics include stability (for example, heat or light stability), compressibility and density (important for formulation and product production), and dissolution rate (which may affect bioavailability), but are not limited thereto. Differences in stability cause changes in chemical reactivity (for example, differential oxidation, as evidenced by more rapid color change when consisting of one polymorph than when consisting of another polymorph) or mechanical characteristics (for example, as dynamically preferred polymorphs, stored tablet fragments are converted into more thermodynamically stable polymorphs), or both (tablets of one polymorph are more sensitive to degradation at high humidity). Other physical properties of polymorphs may affect processing thereof. For example, one polymorph may be more likely to form solvent compounds than another polymorph, for example, due to a form or particle size distribution thereof, or may be more difficult to filter or wash than another polymorph.

As used herein, the term "solvates" refers to the compounds of the present invention or pharmaceutically acceptable salts thereof, including a stoichiometric or non-stoichiometric amount of a solvent bound by a force between non-covalent molecules. Preferred solvents are volatile and non-toxic, and may be administered to a human in a very small amount.

As used herein, the term "hydrates" refers to the compounds of the present invention or pharmaceutically acceptable salts thereof, including a stoichiometric or non-stoichiometric amount of water bound by a force between non-covalent molecules.

As used herein, the term "clathrates" refers to the compounds of the present invention or salts thereof in the form of a crystal lattice including a space (for example, channel) in which guest molecules (for example, a solvent or water) are confined.

When any compounds (prodrugs) are isolated from the body to produce the compounds of the present invention or salts thereof, such compounds are also within the scope of the present invention. As used herein, and unless otherwise indicated, the term "prodrugs" refer to the compounds of the present invention that are capable of undergoing hydrolysis, oxidation, or other reactions under biological conditions (in vitro or in vivo) in order to provide active compounds, particularly the compounds of the present invention. Examples of the prodrugs include compounds that are biodegraded to produce the compounds of the present invention, including biohydrolyzable portions such as biohydrolyzable amides, biohydrolyzable esters, biohydrolyzable carbamates, biohydrolyzable carbonates, biohydrolyzable ureides, and biohydrolyzable phosphate analogs, but are not limited to these specific embodiments. Preferably, prodrugs of compounds having a carboxyl group functional group are lower alkyl esters of carboxylic acids. Carboxylic esters are typically formed by esterifying a portion of carboxylic acids present in the molecule.

Prodrugs may be readily prepared using well known methods as described in the following documents: Burger's Medicinal Chemistry and Drug Discovery 6$^{th}$ ed. (Donald J. Abrahamed., 2001, Wiley) and Design and Application of Prodrugs (H. Bundgaard ed., 1985, Harwood Academic Publishers Gmfh).

As used herein, the term "purified" means that when a substance is isolated, the purity of the isolated substance is at least 90%, and that in one embodiment, the purity of the isolated substance is at least 95%, in another embodiment, the purity is at least 99%, and in still another embodiment, the purity is at least 99.9%.

The term "hydrido" refers to a single —H atom (H), and may be used interchangeably with the symbol "H" or the term "hydrogen".

When substituents are described as being "optionally substituted", the substituents may be unsubstituted (1) or may be substituted with at least one of the defined substituents (2). When a substitutable position is not substituted, a default substituent is a hydrido radical.

As used herein, the singular forms "a" and "an" may include the plural forms unless the context clearly dictates otherwise.

The term "pharmaceutically acceptable" refers to being suitable for use as a pharmaceutical preparation and is generally considered to be safe for such use, and refers to substances which have been formally approved by a national agency for such use or which are on the list of Korean Pharmacopoeia or US Pharmacopoeia.

In order to achieve the aforementioned objects, the present inventors have synthesized compounds which have a high activity of inhibiting the formation of, particularly, a c-Myc/Max/DNA complex and a high selectivity for this inhibitory activity, and as a result, have a good effect of inhibiting cancer cells and reduced side effects other than the effect of inhibiting cancer cells and various compounds to secure the use thereof, and then carried out various evaluation experiments, thereby completing the present invention by finally confirming that the compounds of the present invention are suitable for the object of the present invention.

As an example, a compound having a substituent linked to —S— at the No. 2 position of the basic structure of quinoline is superior in safety to a compound having a substituent linked to —NH—. Specifically, in the case of a compound having a substituent linked to —NH—, the compound is somewhat superior, but has very severe cardiotoxicity. For example, in a mouse xenograft model experiment using a compound KSI-3716 of the following Formula 4, all of the experimental group (30 mpk, intraperitoneal administration (IP)) died, but when the compounds (for example, Compound 4) of the present invention were subjected to IV and IP single toxicity tests at 40 mpk, there were no dead subjects, and no significant weight changes, and no other abnormal symptoms were observed in terms of general symptoms such as feed intake and drinking water intake.

[Formula 4]

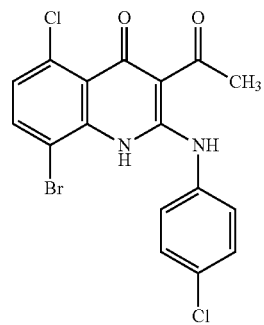

KSI-3716

TABLE 1

| Species | Sex | Dose | Percentage |
|---|---|---|---|
| Mouse | Male | IV 40 mg/kg | 0 (0/2) |
| Mouse | Male | IP 40 mg/kg | 0 (0/2) |
| Mouse | Female | IV 40 mg/kg | 0 (0/2) |
| Mouse | Female | IP 40 mg/kg | 0 (0/2) |

Single toxicity evaluation results of Compound 4 according to the present invention No dead subjects were observed in the 40 mpk single-dose administration experiment.

General symptoms: Feeding and drinking water intakes were good, and no other abnormal symptoms were observed.

Weight changes: In general, a weight gain was observed, but weight gain was slightly reduced in some subjects.

In the case of KSI-3716, all subjects died at 30 mpk (IP).

Further, in cardiotoxicity experiments using zebrafish, all the zebrafish (n=10) died when 5 μM of compounds (for example, KSI-3716 of Formula 4) having a substituent linked to —NH— was used, but when the compounds of the present invention were used, no subjects died and there are no changes in heart rate. The experimental results of representative compounds are shown in the following Table 2.

TABLE 2

| Compound | Changes (%) in heart rate | Lethality | Remarks |
|---|---|---|---|
| 10 uM Astemizole | 46.2 | 0/10 | |
| 5 uM of KSI-3716 | — | 10/10 | Not measurable due to death of all subjects |
| 5 uM of Compound 4 | 88.5 | 1/10 | |
| 5 uM of Compound 33 | 97.3 | 0/10 | No significant heart rate inhibition |

* Changes in heart rate depending on treatment of compounds in zebrafish (mean, n = 10)

As another example, $R_2$ linked to S at the 2-position of the basic structure of quinoline is preferably a phenyl structure in view of the various objects of the present invention, and from the viewpoint of activity, it is preferred that the phenyl group is linked via —CH$_2$—, —CH$_2$CH$_2$—, —CH$_2$CH$_2$CH$_2$—, or —CH$_2$CH$_2$CH$_2$CH$_2$— as a linker (bridge) rather than being directly linked to S, and it is more preferred that the phenyl group is linked via a —CH$_2$— or —CH$_2$CH$_2$— group as a bridge.

As an example, in view of activity, one or more of $R_{1a}$ to $R_{1d}$ are preferably substituted with a substituent, and more preferably with a halogen, and in particular, when Ria and Ria were simultaneously substituted with a halogen, even better activity was observed.

In the case of $R_3$, a $C_{1-4}$ alkyl, an isoalkyl, a cycloalkyl, phenyl, or a $C_{1-4}$ haloalkyl exhibited excellent activity, and in particular, small groups such as methyl or halomethyl exhibited better activity. In addition, when $R_3$ was —CF$_3$, metabolic stability was increased. On the other hand, when $R_3$ was a heteroatom of O or N, the activity desired in the present invention was weak.

In view of the various objects of the present invention, Y is more preferably hydrogen.

$R_4$ ($R_{4a}$ and/or $R_{4b}$) is an important site for metabolic stability, and is more preferably a lower alkyl or halogen for various objects of the present invention.

Non-limiting examples of the compound used as an active ingredient of the pharmaceutical composition according to the present invention include the compounds of the following Table 3 and pharmaceutically acceptable salts thereof.

TABLE 3

| Compound No. | Structure | IUPAC Name |
|---|---|---|
| 1 | 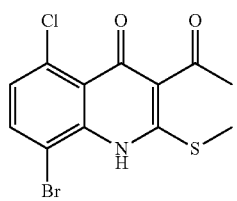 | 3-acetyl-8-bromo-5-chloro-2-(methylsulfinyl)quinolin-4(1H)-one |
| 2 | 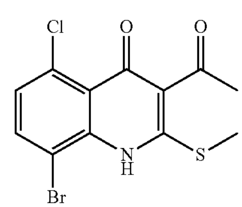 [SMILES: CSc1[nH]c2c(Br)ccc(Cl)c2c(=O)c1C(C)=O] | 3-acetyl-8-bromo-5-chloro-2-(methylthio)quinolin-4(1H)-one |

TABLE 3-continued

| Compound No. | Structure | IUPAC Name |
|---|---|---|
| 3 | 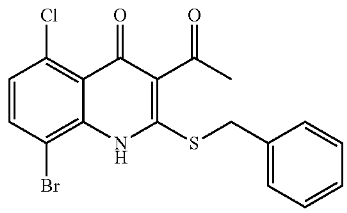 [SMILES: CC(=O)c1c(SCc2ccccc2)[nH]c2c(Br)ccc(Cl)c2c1=O] | 3-acetyl-2-(benzylthio)-8-bromo-5-chloroquinolin-4(1H)-one |
| 4 | 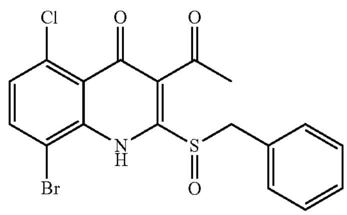 [SMILES: CC(=O)c1c(S(=O)Cc2ccccc2)[nH]c2c(Br)ccc(Cl)c2c1=O] | 3-acetyl-2-benzylsulfinyl-8-bromo-5-chloroquinolin-4(1H)-one |
| 5 | 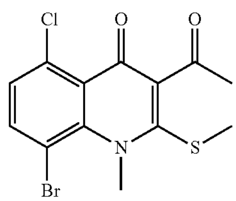 [SMILES: CSc1c(C(C)=O)c(=O)c2c(Cl)ccc(Br)c2n1C] | 3-acetyl-8-bromo-5-chloro-1-methyl-2-(methylthio)quinolin-4(1H)-one |
| 6 | 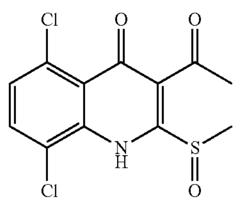 [SMILES: CC(=O)c1c(S(C)=O)[nH]c2c(Cl)ccc(Cl)c2c1=O] | 3-acetyl-5,8-dichloro-2-(methylsulfinyl)quinolin-4(1H)-one |
| 7 | 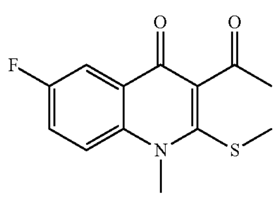 [SMILES: CSc1c(C(C)=O)c(=O)c2cc(F)ccc2n1C] | 3-acetyl-6-fluoro-1-methyl-2-(methylthio)quinolin-4(1H)-one |
| 8 | 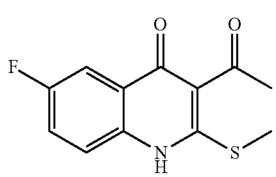 [SMILES: CSc1[nH]c2ccc(F)cc2c(=O)c1C(C)=O] | 1-(6-fluoro-4-hydroxy-2-(methylthio)quinolin-3-yl)ethan-1-one |
| 9 | 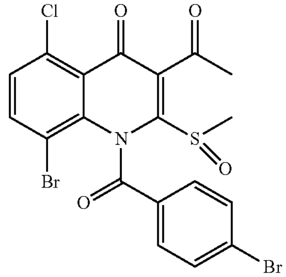 [SMILES: CC(=O)c1c(S(C)=O)n(C(=O)c2ccc(Br)cc2)c2c(Br)ccc(Cl)c2c1=O] | 3-acetyl-8-bromo-1-(4-bromobenzoyl)-5-chloro-2-(methylsulfinyl)quinolin-4(1H)-one |

TABLE 3-continued

| Compound No. | Structure | IUPAC Name |
|---|---|---|
| 10 | 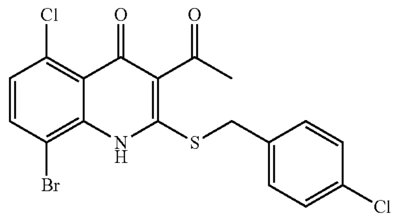 [SMILES: CC(=O)c1c(SCc2ccc(Cl)cc2)[nH]c2c(Br)ccc(Cl)c2c1=O] | 3-acetyl-8-bromo-5-chloro-2-((4-chlorobenzyl)thio)quinolin-4(1H)-one |
| 11 | 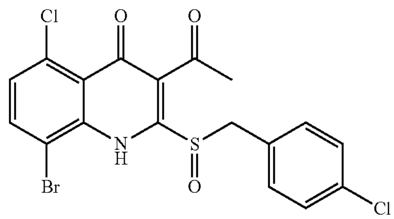 [SMILES: CC(=O)c1c(S(=O)Cc2ccc(Cl)cc2)[nH]c2c(Br)ccc(Cl)c2c1=O] | 3-acetyl-8-bromo-5-chloro-2-((4-chlorobenzyl)sulfinyl)quinolin-4(1H)-one |
| 12 | 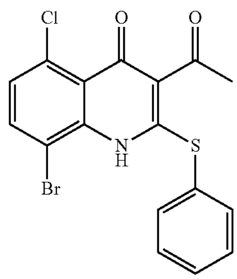 [SMILES: CC(=O)c1c(Sc2ccccc2)[nH]c2c(Br)ccc(Cl)c2c1=O] | 3-acetyl-8-bromo-5-chloro-2-(phenylthio)quinolin-4(1H)-one |
| 13 | 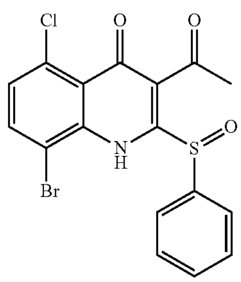 [SMILES: CC(=O)c1c(S(=O)c2ccccc2)[nH]c2c(Br)ccc(Cl)c2c1=O] | 3-acetyl-8-bromo-5-chloro-2-(phenylsulfinyl)quinolin-4(1H)-one |
| 14 | 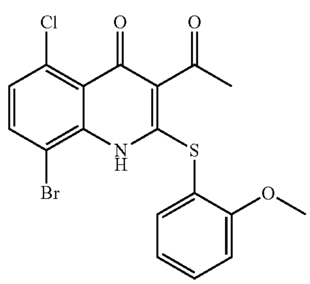 [SMILES: COc1ccccc1Sc1[nH]c2c(Br)ccc(Cl)c2c(=O)c1C(C)=O] | 3-acetyl-8-bromo-5-chloro-2-((2-methoxyphenyl)thio)quinolin-4(1H)-one |
| 15 | 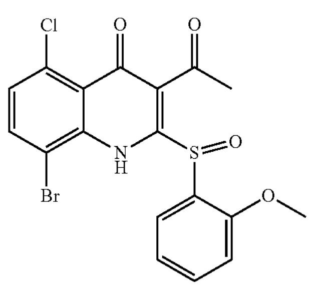 [SMILES: COc1ccccc1S(=O)c1[nH]c2c(Br)ccc(Cl)c2c(=O)c1C(C)=O] | 3-acetyl-8-bromo-5-chloro-2-((2-methoxyphenyl)sulfinyl)quinolin-4(1H)-one |

TABLE 3-continued

| Compound No. | Structure | IUPAC Name |
|---|---|---|
| 16 | 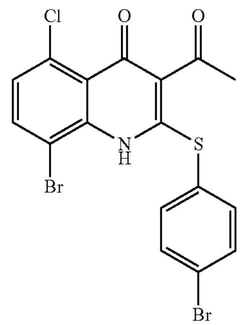 [SMILES: CC(=O)c1c(Sc2ccc(Br)cc2)[nH]c2c(Br)ccc(Cl)c2c1=O] | 3-acetyl-8-bromo-2-((4-bromophenyl)thio)-5-chloroquinolin-4(1H)-one |
| 17 | 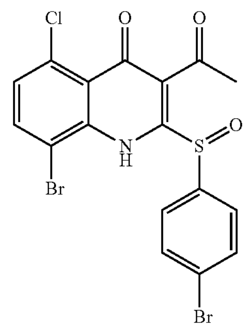 [SMILES: CC(=O)c1c(S(=O)c2ccc(Br)cc2)[nH]c2c(Br)ccc(Cl)c2c1=O] | 3-acetyl-8-bromo-2-((4-bromophenyl)sulfinyl)-5-chloroquinolin-4(1H)-one |
| 18 | 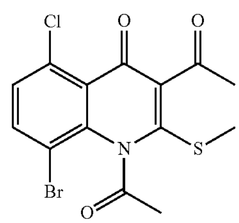 [SMILES: CSc1c(C(C)=O)c(=O)c2c(Cl)ccc(Br)c2n1C(C)=O] | 1,1'-(8-bromo-5-chloro-2-(methylthio)-4-oxoquinoline-1,3(4H)-diyl)bis(ethan-1-one) |
| 19 | 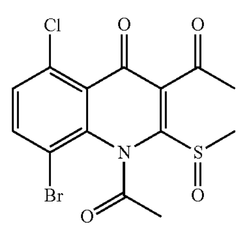 [SMILES: CC(=O)c1c(S(C)=O)n(C(C)=O)c2c(Br)ccc(Cl)c2c1=O] | 1,1'-(8-bromo-5-chloro-2-(methylsulfinyl)-4-oxoquinoline-1,3(4H)-diyl)bis(ethan-1-one) |
| 20 | 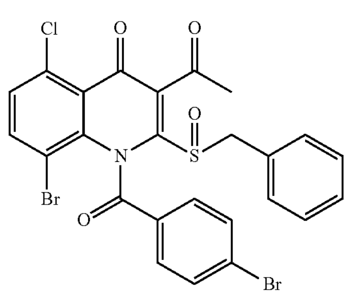 [SMILES: CC(=O)c1c(S(=O)Cc2ccccc2)n(C(=O)c2ccc(Br)cc2)c2c(Br)ccc(Cl)c2c1=O] | 3-acetyl-2-(benzylsulfinyl)-8-bromo-1-(4-bromobenzoyl)-5-chloroquinolin-4(1H)-one |

TABLE 3-continued

| Compound No. | Structure | IUPAC Name |
|---|---|---|
| 21 | 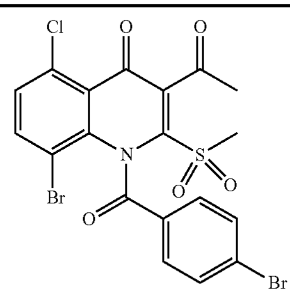 | 3-acetyl-8-bromo-1-(4-bromobenzoyl)-5-chloro-2-(methylsulfonyl)quinolin-4(1H)-one |
| 22 | 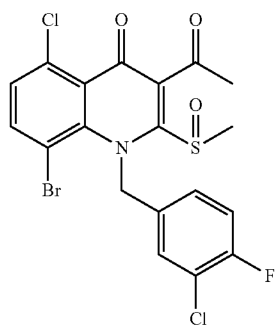 [SMILES: CC(=O)c1c(S(C)=O)n(Cc2ccc(F)c(Cl)c2)c2c(Br)ccc(Cl)c2c1=O] | 3-acetyl-8-bromo-5-chloro-1-(3-chloro-4-fluorobenzyl)-2-(methylsulfinyl)quinolin-4(1H)-one |
| 23 | 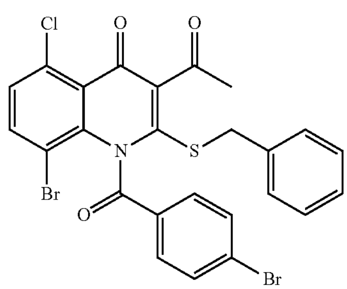 [SMILES: CC(=O)c1c(SCc2ccccc2)n(C(=O)c2ccc(Br)cc2)c2c(Br)ccc(Cl)c2c1=O] | 3-acetyl-2-(benzylthio)-8-bromo-1-(4-bromobenzoyl)-5-chloroquinolin-4(1H)-one |
| 24 | 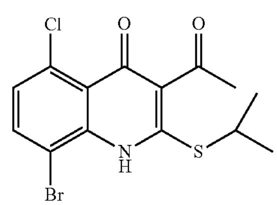 [SMILES: CC(=O)c1c(SC(C)C)[nH]c2c(Br)ccc(Cl)c2c1=O] | 3-acetyl-8-bromo-5-chloro-2-(isopropylthio)quinolin-4(1H)-one |
| 25 | 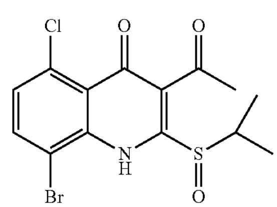 [SMILES: CC(=O)c1c(S(=O)C(C)C)[nH]c2c(Br)ccc(Cl)c2c1=O] | 3-acetyl-8-bromo-5-chloro-2-(isopropylsulfinyl)quinolin-4(1H)-one |
| 26 | 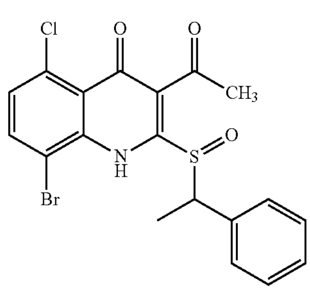 [SMILES: CC(=O)c1c(S(=O)C(C)c2ccccc2)[nH]c2c(Br)ccc(Cl)c2c1=O] | 3-acetyl-8-bromo-5-chloro-2-((1-phenylethyl)sulfinyl)quinolin-4(1H)-one |

TABLE 3-continued

| Compound No. | Structure | IUPAC Name |
|---|---|---|
| 27 | 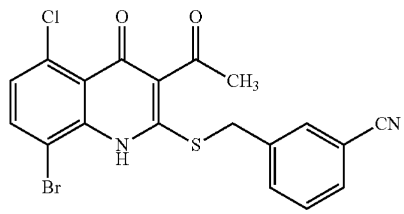 [SMILES: CC(=O)c1c(SCc2cccc(C#N)c2)[nH]c2c(Br)ccc(Cl)c2c1=O] | 3-(((3-acetyl-8-bromo-5-chloro-4-oxo-1,4-dihydroquinolin-2-yl)thio)methyl)benzonitrile |
| 28 | 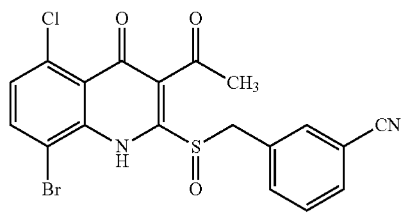 [SMILES: CC(=O)c1c(S(=O)Cc2cccc(C#N)c2)[nH]c2c(Br)ccc(Cl)c2c1=O] | 3-(((3-acetyl-8-bromo-5-chloro-4-oxo-1,4-dihydroquinolin-2-yl)sulfinyl)methyl)benzonitrile |
| 29 | 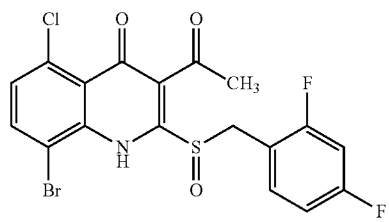 [SMILES: CC(=O)c1c(S(=O)Cc2ccc(F)cc2F)[nH]c2c(Br)ccc(Cl)c2c1=O] | 3-acetyl-8-bromo-5-chloro-2-((2,4-difluorobenzyl)sulfinyl)quinolin-4(1H)-one |
| 30 | 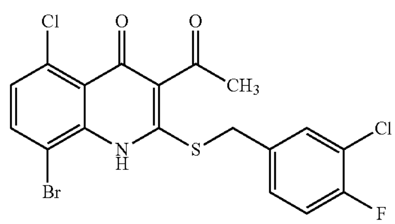 [SMILES: CC(=O)c1c(SCc2ccc(F)c(Cl)c2)[nH]c2c(Br)ccc(Cl)c2c1=O] | 3-acetyl-8-bromo-5-chloro-2-((3-chloro-4-fluorobenzyl)thio)quinolin-4(1H)-one |
| 31 | 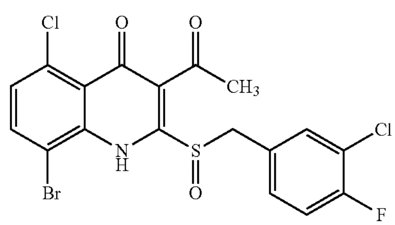 [SMILES: CC(=O)c1c(S(=O)Cc2ccc(F)c(Cl)c2)[nH]c2c(Br)ccc(Cl)c2c1=O] | 3-acetyl-8-bromo-5-chloro-2-((3-chloro-4-fluorobenzyl)sulfinyl)quinolin-4(1H)-one |
| 32 | 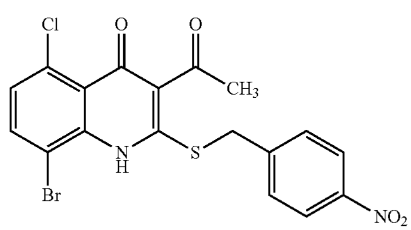 [SMILES: CC(=O)c1c(SCc2ccc([N+](=O)[O-])cc2)[nH]c2c(Br)ccc(Cl)c2c1=O] | 3-acetyl-8-bromo-5-chloro-2-((4-nitrobenzyl)thio)quinolin-4(1H)-one |
| 33 | 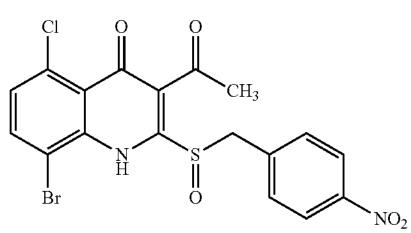 [SMILES: CC(=O)c1c(S(=O)Cc2ccc([N+](=O)[O-])cc2)[nH]c2c(Br)ccc(Cl)c2c1=O] | 3-acetyl-8-bromo-5-chloro-2-((4-nitrobenzyl)sulfinyl)quinolin-4(1H)-one |

TABLE 3-continued

| Compound No. | Structure | IUPAC Name |
|---|---|---|
| 34 | 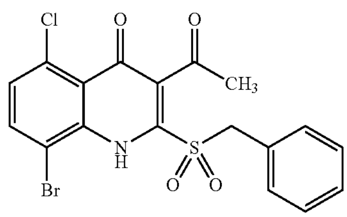 [SMILES: CC(=O)c1c(S(=O)(=O)Cc2ccccc2)[nH]c2c(Br)ccc(Cl)c2c1=O] | 3-acetyl-2-(benzylsulfonyl)-8-bromo-5-chloroquinolin-4(1H)-one |
| 35 | 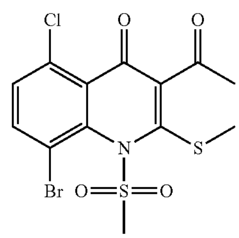 [SMILES: CSc1c(C(C)=O)c(=O)c2c(Cl)ccc(Br)c2n1S(C)(=O)=O] | 3-acetyl-8-bromo-5-chloro-1-(methylsulfonyl)-2-(methylthio)quinolin-4(1H)-one |
| 36 | 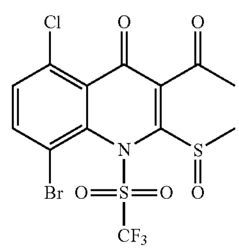 [SMILES: CC(=O)c1c(S(C)=O)n(S(=O)(=O)C(F)(F)F)c2c(Br)ccc(Cl)c2c1=O] | 3-acetyl-8-bromo-5-chloro-2-(methylsulfinyl)-1-((trifluoromethyl)sulfonyl)quinolin-4(1H)-one |
| 37 | 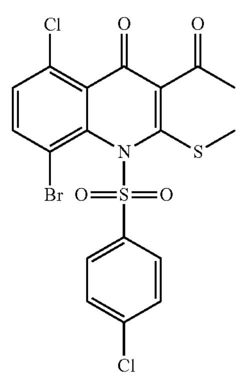 [SMILES: CSc1c(C(C)=O)c(=O)c2c(Cl)ccc(Br)c2n1S(=O)(=O)c1ccc(Cl)cc1] | 3-acetyl-8-bromo-5-chloro-1-((4-chlorophenyl)sulfonyl)-2-(methylthio)quinolin-4(1H)-one |
| 38 | 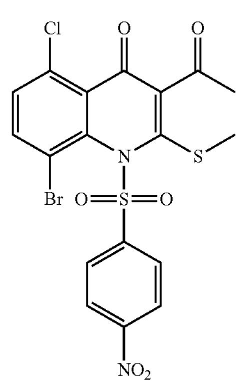 [SMILES: CSc1c(C(C)=O)c(=O)c2c(Cl)ccc(Br)c2n1S(=O)(=O)c1ccc([N+](=O)[O-])cc1] | 3-acetyl-8-bromo-5-chloro-2-(methylthio)-1-((4-nitrophenyl)sulfonyl)quinolin-4(1H)-one |

TABLE 3-continued

| Compound No. | Structure | IUPAC Name |
|---|---|---|
| 39 | 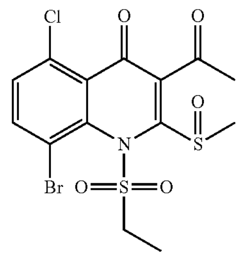 [SMILES: CCS(=O)(=O)n1c(S(C)=O)c(C(C)=O)c(=O)c2c(Cl)ccc(Br)c21] | 3-acetyl-8-bromo-5-chloro-1-(ethylsulfonyl)-2-(methylsulfinyl)quinolin-4(1H)-one |
| 40 | 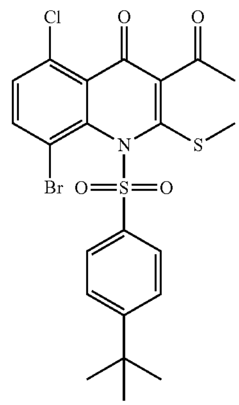 [SMILES: CSc1c(C(C)=O)c(=O)c2c(Cl)ccc(Br)c2n1S(=O)(=O)c1ccc(C(C)(C)C)cc1] | 3-acetyl-8-bromo-1-((4-(tert-butyl)phenyl)sulfonyl)-5-chloro-2-(methylthio)quinolin-4(1H)-one |
| 41 | 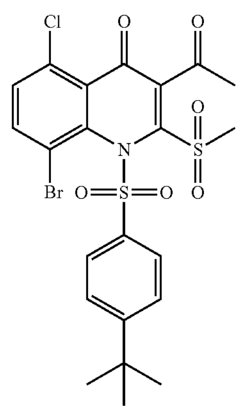 [SMILES: CC(=O)c1c(S(C)(=O)=O)n(S(=O)(=O)c2ccc(C(C)(C)C)cc2)c2c(Br)ccc(Cl)c2c1=O] | 3-acetyl-8-bromo-1-((4-(tert-butyl)phenyl)sulfonyl)-5-chloro-2-(methylsulfonyl)quinolin-4(1H)-one |
| 42 | 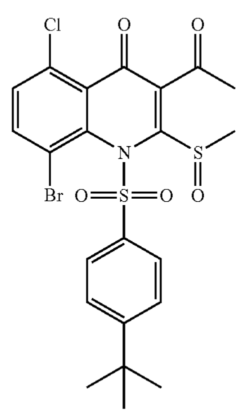 [SMILES: CC(=O)c1c(S(C)=O)n(S(=O)(=O)c2ccc(C(C)(C)C)cc2)c2c(Br)ccc(Cl)c2c1=O] | 3-acetyl-8-bromo-1-((4-(tert-butyl)phenyl)sulfonyl)-5-chloro-2-(methylsulfinyl)quinolin-4(1H)-one |

TABLE 3-continued

| Compound No. | Structure | IUPAC Name |
|---|---|---|
| 43 | 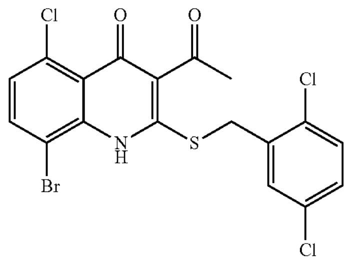 [SMILES: CC(=O)c1c(SCc2cc(Cl)ccc2Cl)[nH]c2c(Br)ccc(Cl)c2c1=O] | 3-acetyl-8-bromo-5-chloro-2-((2,5-dichlorobenzyl)thio)quinolin-4(1H)-one |
| 44 | 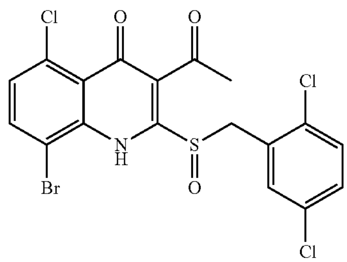 [SMILES: CC(=O)c1c(S(=O)Cc2cc(Cl)ccc2Cl)[nH]c2c(Br)ccc(Cl)c2c1=O] | 3-acetyl-8-bromo-5-chloro-2-((2,5-dichlorobenzyl)sulfinyl)quinolin-4(1H)-one |
| 45 | 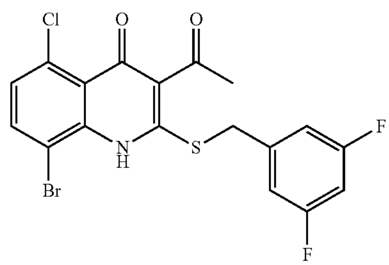 [SMILES: CC(=O)c1c(SCc2cc(F)cc(F)c2)[nH]c2c(Br)ccc(Cl)c2c1=O] | 3-acetyl-8-bromo-5-chloro-2-((3,5-difluorobenzyl)thio)quinolin-4(1H)-one |
| 46 | 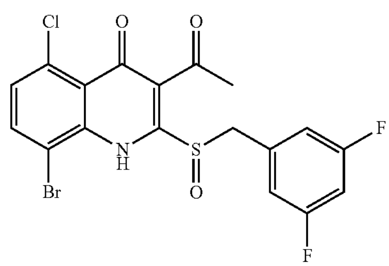 [SMILES: CC(=O)c1c(S(=O)Cc2cc(F)cc(F)c2)[nH]c2c(Br)ccc(Cl)c2c1=O] | 3-acetyl-8-bromo-5-chloro-2-((3,5-difluorobenzyl)sulfinyl)quinolin-4(1H)-one |
| 47 | 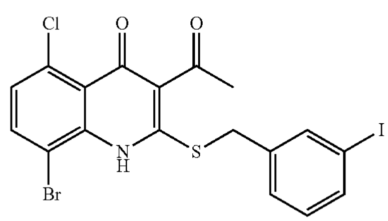 [SMILES: CC(=O)c1c(SCc2cccc(I)c2)[nH]c2c(Br)ccc(Cl)c2c1=O] | 3-acetyl-8-bromo-5-chloro-2-((3-iodobenzyl)thio)quinolin-4(1H)-one |
| 48 | 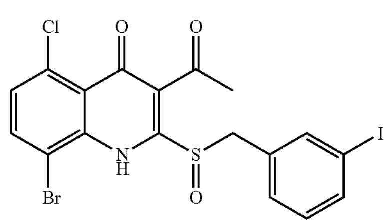 [SMILES: CC(=O)c1c(S(=O)Cc2cccc(I)c2)[nH]c2c(Br)ccc(Cl)c2c1=O] | 3-acetyl-8-bromo-5-chloro-2-((3-iodobenzyl)sulfinyl)quinolin-4(1H)-one |

TABLE 3-continued

| Compound No. | Structure | IUPAC Name |
|---|---|---|
| 49 | 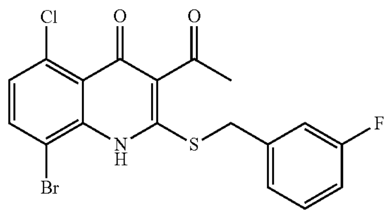 [SMILES: CC(=O)c1c(SCc2cccc(F)c2)[nH]c2c(Br)ccc(Cl)c2c1=O] | 3-acetyl-8-bromo-5-chloro-2-((3-fluorobenzyl)thio)quinolin-4(1H)-one |
| 50 | 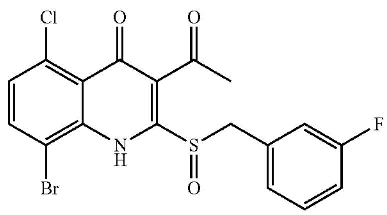 [SMILES: CC(=O)c1c(S(=O)Cc2cccc(F)c2)[nH]c2c(Br)ccc(Cl)c2c1=O] | 3-acetyl-8-bromo-5-chloro-2-((3-fluorobenzyl)sulfinyl)quinolin-4(1H)-one |
| 51 | 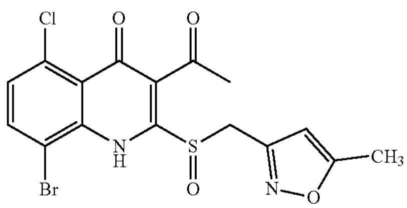 [SMILES: CC(=O)c1c(S(=O)Cc2cc(C)on2)[nH]c2c(Br)ccc(Cl)c2c1=O] | 3-acetyl-8-bromo-5-chloro-2-(((5-methylisoxazol-3-yl)methyl)sulfinyl)quinolin-4(1H)-one |
| 52 | 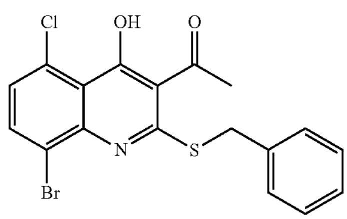 [SMILES: CC(=O)c1c(SCc2ccccc2)nc2c(Br)ccc(Cl)c2c1O] | 1-(2-(benzylthio)-8-bromo-5-chloro-4-hydroxyquinolin-3-yl)ethan-1-one |
| 53 | 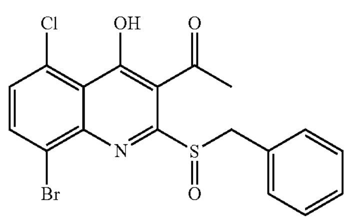 [SMILES: CC(=O)c1c(S(=O)Cc2ccccc2)nc2c(Br)ccc(Cl)c2c1O] | 1-(2-(benzylsulfinyl)-8-bromo-5-chloro-4-hydroxyquinolin-3-yl)ethan-1-one |
| 54 | 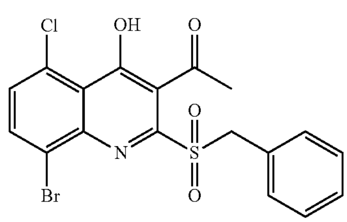 [SMILES: CC(=O)c1c(S(=O)(=O)Cc2ccccc2)nc2c(Br)ccc(Cl)c2c1O] | 1-(2-(benzylsulfonyl)-8-bromo-5-chloro-4-hydroxyquinolin-3-yl)ethan-1-one |
| 55 | 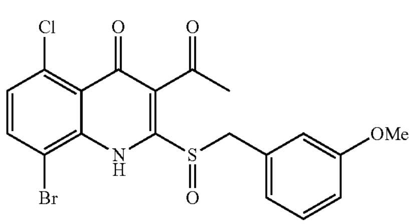 [SMILES: COc1cccc(CS(=O)c2[nH]c3c(Br)ccc(Cl)c3c(=O)c2C(C)=O)c1] | 3-acetyl-8-bromo-5-chloro-2-((3-methoxybenzyl)sulfinyl)quinolin-4(1H)-one |

TABLE 3-continued

| Compound No. | Structure | IUPAC Name |
|---|---|---|
| 56 | 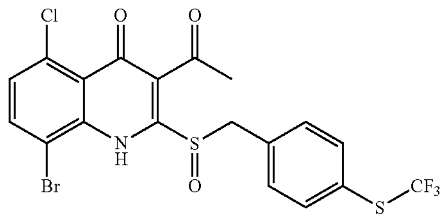 [SMILES: CC(=O)c1c(S(=O)Cc2ccc(SC(F)(F)F)cc2)[nH]c2c(Br)ccc(Cl)c2c1=O] | 3-acetyl-8-bromo-5-chloro-2-((4-((trifluoromethyl)thio)benzyl)sulfinyl)quinolin-4(1H)-one |
| 57 | 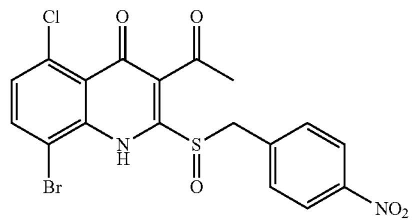 [SMILES: CC(=O)c1c(S(=O)Cc2ccc([N+](=O)[O-])cc2)[nH]c2c(Br)ccc(Cl)c2c1=O] | 3-acetyl-5,8-dichloro-2-((4-nitrobenzyl)sulfinyl)quinolin-4(1H)-one |
| 58 | 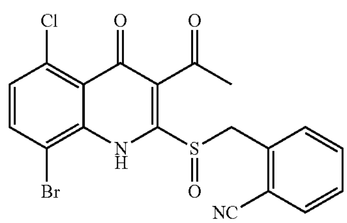 [SMILES: CC(=O)c1c(S(=O)Cc2ccccc2C#N)[nH]c2c(Br)ccc(Cl)c2c1=O] | 2-(((3-acetyl-8-bromo-5-chloro-4-oxo-1,4-dihydroquinolin-2-yl)sulfinyl)methyl)benzonitrile |
| 59 | 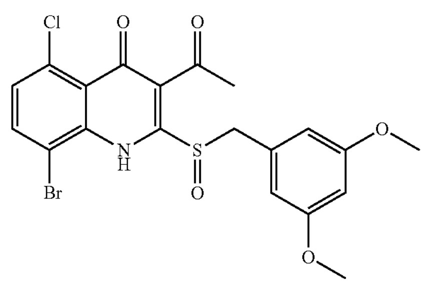 [SMILES: COc1cc(CS(=O)c2[nH]c3c(Br)ccc(Cl)c3c(=O)c2C(C)=O)cc(OC)c1] | 3-acetyl-8-bromo-5-chloro-2-((3,5-dimethoxybenzyl)sulfinyl)quinolin-4(1H)-one |
| 60 | 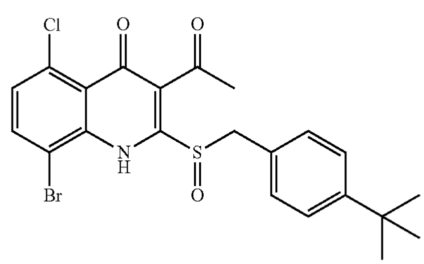 [SMILES: CC(=O)c1c(S(=O)Cc2ccc(C(C)(C)C)cc2)[nH]c2c(Br)ccc(Cl)c2c1=O] | 3-acetyl-8-bromo-2-((4-(tert-butyl)benzyl)sulfinyl)-5-chloroquinolin-4(1H)-one |
| 61 | 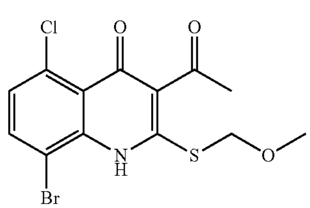 [SMILES: COCSc1[nH]c2c(Br)ccc(Cl)c2c(=O)c1C(C)=O] | 3-acetyl-8-bromo-5-chloro-2-((methoxymethyl)thio)quinolin-4(1H)-one |

TABLE 3-continued

| Compound No. | Structure | IUPAC Name |
|---|---|---|
| 62 | 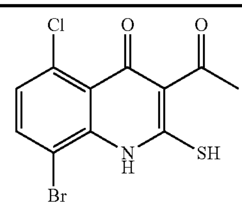 | 3-acetyl-8-bromo-5-chloro-2-mercaptoquinolin-4(1H)-one |
| 63 | 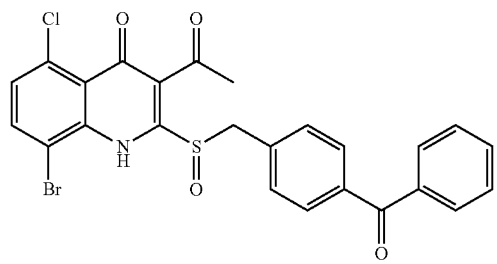 [SMILES: CC(=O)c1c(S(=O)Cc2ccc(C(=O)c3ccccc3)cc2)[nH]c2c(Br)ccc(Cl)c2c1=O] | 3-acetyl-2-((4-benzoylbenzyl)sulfinyl)-8-bromo-5-chloroquinolin-4(1H)-one |
| 64 | 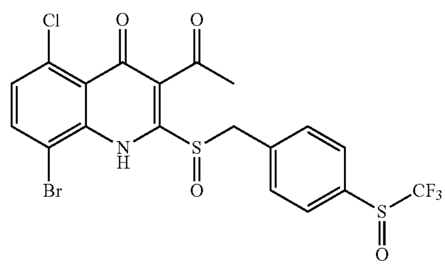 [SMILES: CC(=O)c1c(S(=O)Cc2ccc(S(=O)C(F)(F)F)cc2)[nH]c2c(Br)ccc(Cl)c2c1=O] | 3-acetyl-8-bromo-5-chloro-2-((4-((trifluoromethyl)sulfinyl)benzyl)sulfinyl)quinolin-4(1H)-one |
| 65 | 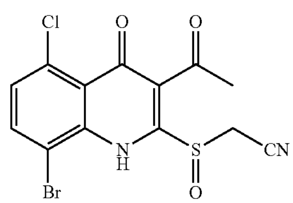 [SMILES: CC(=O)c1c(S(=O)CC#N)[nH]c2c(Br)ccc(Cl)c2c1=O] | 2-((3-acetyl-8-bromo-5-chloro-4-oxo-1,4-dihydroquinolin-2-yl)sulfinyl)acetonitrile |
| 66 | 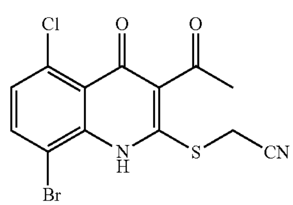 [SMILES: CC(=O)c1c(SCC#N)[nH]c2c(Br)ccc(Cl)c2c1=O] | 2-((3-acetyl-8-bromo-5-chloro-4-oxo-1,4-dihydroquinolin-2-yl)thio)acetonitrile |
| 67 | 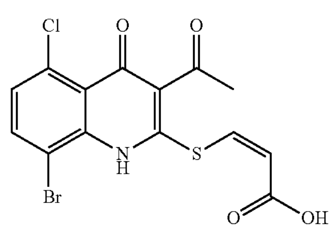 [SMILES: CC(=O)c1c(S/C=C\C(=O)O)[nH]c2c(Br)ccc(Cl)c2c1=O] | (Z)-3-((3-acetyl-8-bromo-5-chloro-4-oxo-1,4-dihydroquinolin-2-yl)thio)acrylic acid |
| 68 | 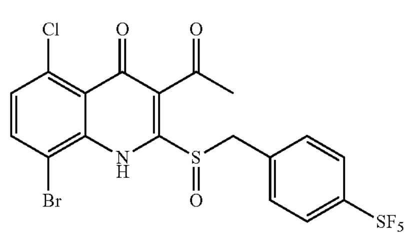 [SMILES: CC(=O)c1c(S(=O)Cc2ccc(C(F)(F)F)cc2)[nH]c2c(Br)ccc(Cl)c2c1=O] | 3-acetyl-8-bromo-5-chloro-2-((4-(pentafluoro-16-sulfanyl)benzyl)sulfinyl)quinolin-4(1H)-one |

TABLE 3-continued

| Compound No. | Structure | IUPAC Name |
|---|---|---|
| 69 | 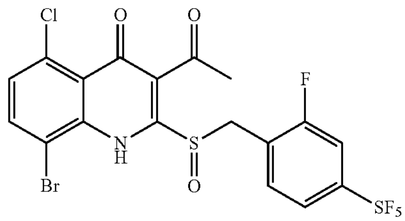 | 3-acetyl-8-bromo-5-chloro-2-((2-fluoro-4-(pentafluoro-l6-sulfanyl)benzyl)sulfinyl)quinolin-4(1H)-one |
| 70 | 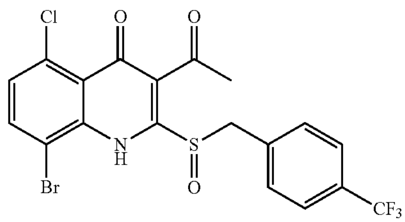 | 3-acetyl-8-bromo-5-chloro-2-((4-(trifluoromethyl)benzyl)sulfinyl)quinolin-4(1H)-one |
| 71 | 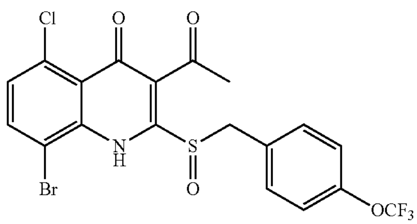 [SMILES: CC(=O)c1c(S(=O)Cc2ccc(OC(F)(F)F)cc2)[nH]c2c(Br)ccc(Cl)c2c1=O] | 3-acetyl-8-bromo-5-chloro-2-((4-(trifluoromethoxy)benzyl)sulfinyl)quinolin-4(1H)-one |
| 72 | 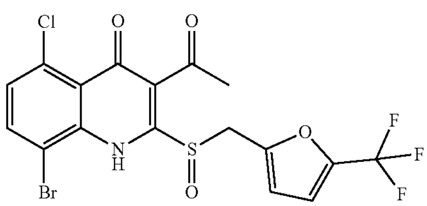 [SMILES: CC(=O)c1c(S(=O)Cc2ccc(C(F)(F)F)o2)[nH]c2c(Br)ccc(Cl)c2c1=O] | 3-acetyl-8-bromo-5-chloro-2-(((5-(trifluoromethyl)furan-2-yl)methyl)sulfinyl)quinolin-4(1H)-one |
| 73 | 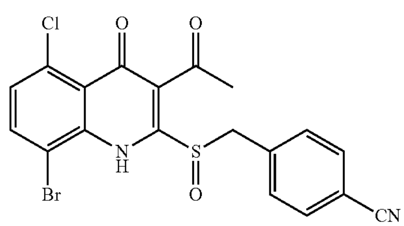 [SMILES: CC(=O)c1c(S(=O)Cc2ccc(C#N)cc2)[nH]c2c(Br)ccc(Cl)c2c1=O] | 4-(((3-acetyl-8-bromo-5-chloro-4-oxo-1,4-dihydroquinolin-2-yl)sulfinyl)methyl)benzonitrile |
| 74 | 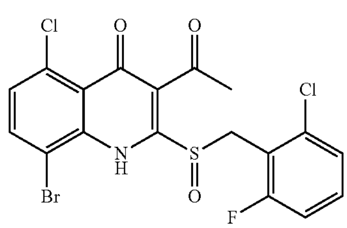 [SMILES: CC(=O)c1c(S(=O)Cc2c(F)cccc2Cl)[nH]c2c(Br)ccc(Cl)c2c1=O] | 3-acetyl-8-bromo-5-chloro-2-((2-chloro-6-fluorobenzyl)sulfinyl)quinolin-4(1H)-one |
| 75 | 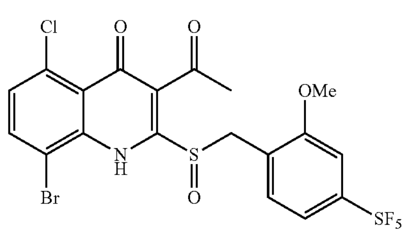 | 3-acetyl-8-bromo-5-chloro-2-((2-methoxy-4-(pentafluoro--sulfanyl)benzyl)sulfinyl)quinolin-4(1H)-one |

TABLE 3-continued

| Compound No. | Structure | IUPAC Name |
|---|---|---|
| 76 | 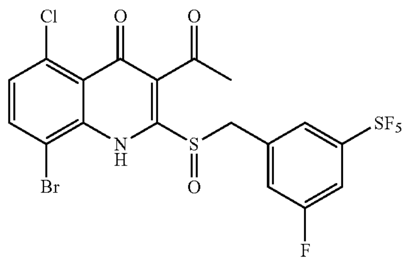 | 3-acetyl-8-bromo-5-chloro-2-((3-fluoro-5-(pentafluoro-sulfanyl)benzyl)sulfinyl)quinolin-4(1H)-one |
| 77 | 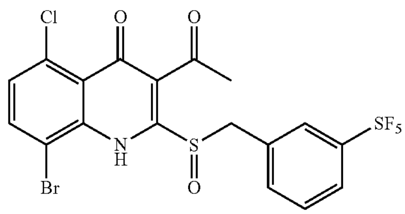 | 3-acetyl-8-bromo-5-chloro-2-((3-(pentafluoro-sulfanyl)benzyl)sulfinyl)quinolin-4(1H)-one |
| 78 | 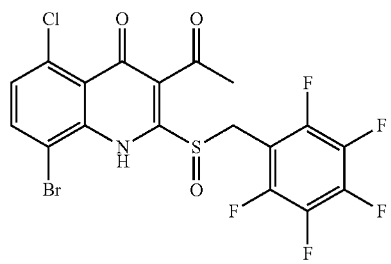 [SMILES: CC(=O)c1c(S(=O)Cc2c(F)c(F)c(F)c(F)c2F)[nH]c2c(Br)ccc(Cl)c2c1=O] | 3-acetyl-8-bromo-5-chloro-2-(((perfluorophenyl)methyl)sulfinyl)quinolin-4(1H)-one |
| 79 | 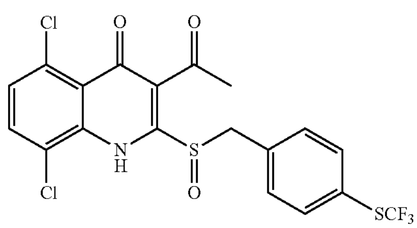 | 3-acetyl-5,8-dichloro-2-((4-((trifluoromethyl)thio)benzyl)sulfinyl)quinolin-4(1H)-one |
| 80 | 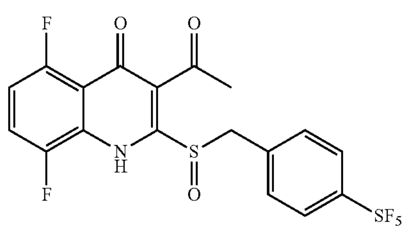 | 3-acetyl-5,8-difluoro-2-((4-(pentafluoro-sulfanyl)benzyl)sulfinyl)quinolin-4(1H)-one |
| 81 | 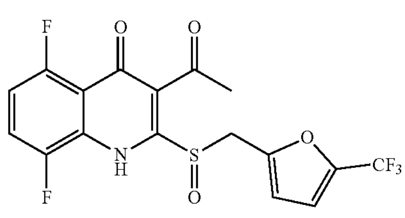 [SMILES: CC(=O)c1c(S(=O)Cc2ccc(C(F)(F)F)o2)[nH]c2c(F)ccc(F)c2c1=O] | 3-acetyl-5,8-difluoro-2-(((5-(trifluoromethyl)furan-2-yl)methyl)sulfinyl)quinolin-4(1H)-one |

TABLE 3-continued

| Compound No. | Structure | IUPAC Name |
|---|---|---|
| 82 | 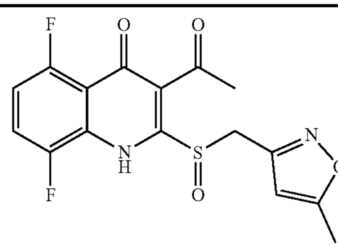 | 3-acetyl-5,8-difluoro-2-(((5-methylisoxazol-3-yl)methyl)sulfinyl)quinolin-4(1H)-one |
| 83 | 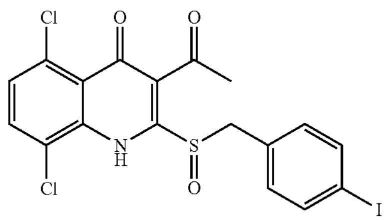 [SMILES: CC(=O)c1c(S(=O)Cc2ccc(I)cc2)[nH]c2c(Cl)ccc(Cl)c2c1=O] | 3-acetyl-5,8-dichloro-2-((4-iodobenzyl)sulfinyl)quinolin-4(1H)-one |
| 84 | 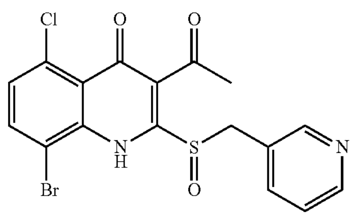 [SMILES: CC(=O)c1c(S(=O)Cc2cccnc2)[nH]c2c(Br)ccc(Cl)c2c1=O] | 3-acetyl-8-bromo-5-chloro-2-((pyridin-3-ylmethyl)sulfinyl)quinolin-4(1H)-one |
| 85 | 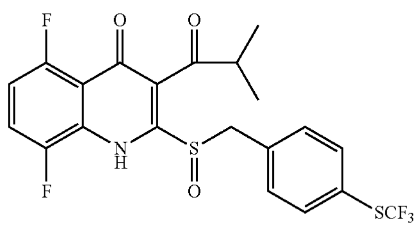 | 5,8-difluoro-3-isobutyryl-2-((4-((trifluoromethyl)thio)benzyl)sulfinyl)quinolin-4(1H)-one |
| 86 | 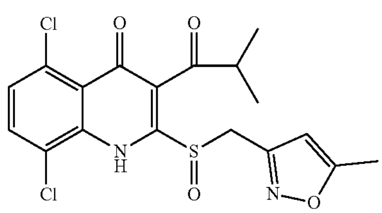 [SMILES: Cc1cc(CS(=O)c2[nH]c3c(Cl)ccc(Cl)c3c(=O)c2C(=O)C(C)C)no1] | 5,8-dichloro-3-isobutyryl-2-(((5-methylisoxazol-3-yl)methyl)sulfinyl)quinolin-4(1H)-one |
| 87 | 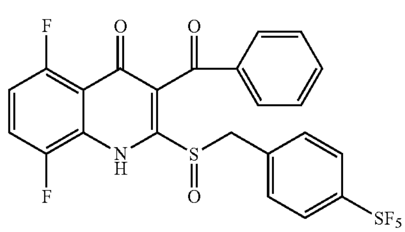 | 3-benzoyl-5,8-difluoro-2-((4-(pentafluorosulfanyl)benzyl)sulfinyl)quinolin-4(1H)-one |
| 88 | 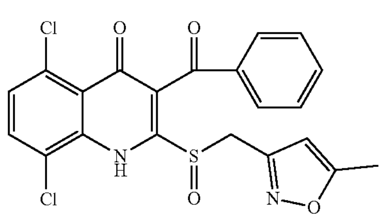 [SMILES: Cc1cc(CS(=O)c2[nH]c3c(Cl)ccc(Cl)c3c(=O)c2C(=O)c2ccccc2)no1] | 3-benzoyl-5,8-dichloro-2-(((5-methylisoxazol-3-yl)methyl)sulfinyl)quinolin-4(1H)-one |

TABLE 3-continued

| Compound No. | Structure | IUPAC Name |
| --- | --- | --- |
| 89 | 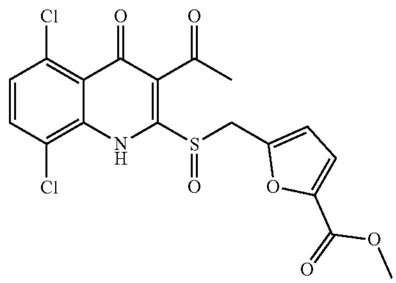 [SMILES: COC(=O)c1ccc(CS(=O)c2[nH]c3c(Cl)ccc(Cl)c3c(=O)c2C(C)=O)o1] | methyl 5-(((3-acetyl-5,8-dichloro-4-oxo-1,4-dihydroquinolin-2-yl)sulfinyl)methyl)furan-2-carboxylate |
| 90 | 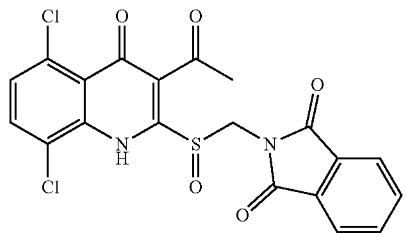 [SMILES: CC(=O)c1c(S(=O)CN2C(=O)c3ccccc3C2=O)[nH]c2c(Cl)ccc(Cl)c2c1=O] | 2-(((3-acetyl-5,8-dichloro-4-oxo-1,4-dihydroquinolin-2-yl)sulfinyl)methyl)isoindoline-1,3-dione |
| 91 | 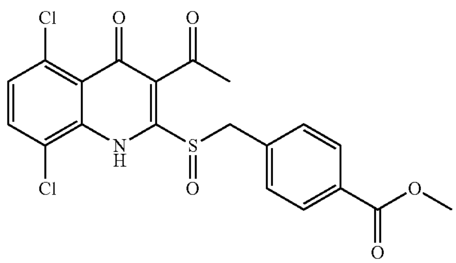 [SMILES: COC(=O)c1ccc(CS(=O)c2[nH]c3c(Cl)ccc(Cl)c3c(=O)c2C(C)=O)cc1] | methyl 4-(((3-acetyl-5,8-dichloro-4-oxo-1,4-dihydroquinolin-2-yl)sulfinyl)methyl)benzoate |
| 92 | 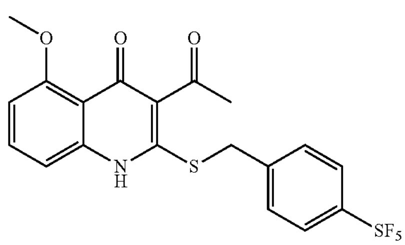 | 3-acetyl-5-methoxy-2-((4-(pentafluorosulfanyl)benzyl)thio)quinolin-4(1H)-one |
| 93 | 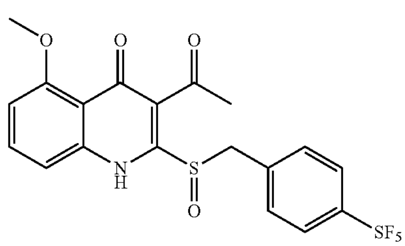 | 3-acetyl-5-methoxy-2-((4-(pentafluorosulfanyl)benzyl)sulfinyl)quinolin-4(1H)-one |
| 94 | 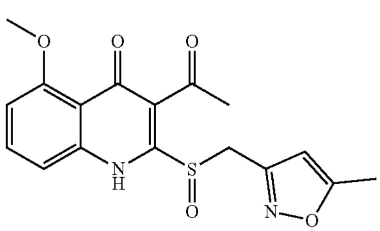 [SMILES: COc1cccc2[nH]c(S(=O)Cc3cc(C)on3)c(C(C)=O)c(=O)c12] | 3-acetyl-5-methoxy-2-(((5-methylisoxazol-3-yl)methyl)sulfinyl)quinolin-4(1H)-one |

TABLE 3-continued

| Compound No. | Structure | IUPAC Name |
|---|---|---|
| 95 | 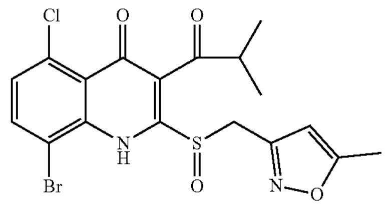 [SMILES: Cc1cc(CS(=O)c2[nH]c3c(Br)ccc(Cl)c3c(=O)c2C(=O)C(C)C)no1] | 8-bromo-5-chloro-3-isobutyryl-2-(((5-methylisoxazol-3-yl)methyl)sulfinyl)quinolin-4(1H)-one |
| 96 | 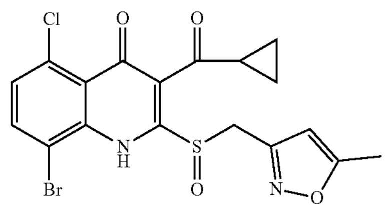 [SMILES: Cc1cc(CS(=O)c2[nH]c3c(Br)ccc(Cl)c3c(=O)c2C(=O)C2CC2)no1] | 8-bromo-5-chloro-3-(cyclopropanecarbonyl)-2-(((5-methylisoxazol-3-yl)methyl)sulfinyl)quinolin-4(1H)-one |
| 97 | 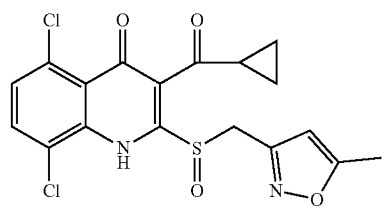 [SMILES: Cc1cc(CS(=O)c2[nH]c3c(Cl)ccc(Cl)c3c(=O)c2C(=O)C2CC2)no1] | 5,8-dichloro-3-(cyclopropanecarbonyl)-2-(((5-methylisoxazol-3-yl)methyl)sulfinyl)quinolin-4(1H)-one |
| 98 | 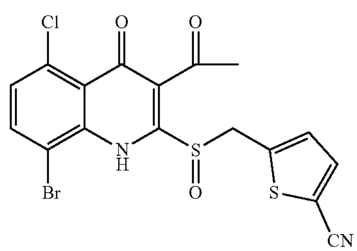 [SMILES: CC(=O)c1c(S(=O)Cc2ccc(C#N)s2)[nH]c2c(Br)ccc(Cl)c2c1=O] | 5-(((3-acetyl-8-bromo-5-chloro-4-oxo-1,4-dihydroquinolin-2-yl)sulfinyl)methyl)thiophene-2-carbonitrile |
| 99 | 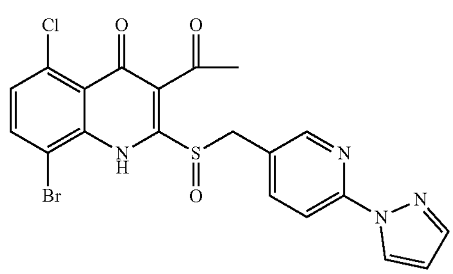 [SMILES: CC(=O)c1c(S(=O)Cc2ccc(-n3cccn3)nc2)[nH]c2c(Br)ccc(Cl)c2c1=O] | 2-(((6-(1H-pyrazol-1-yl)pyridin-3-yl)methyl)sulfinyl)-3-acetyl-8-bromo-5-chloroquinolin-4(1H)-one |
| 100 | 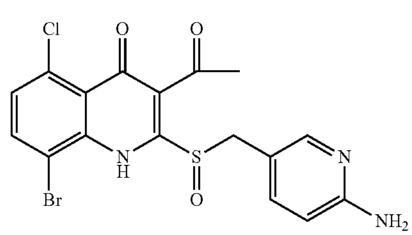 [SMILES: CC(=O)c1c(S(=O)Cc2ccc(N)nc2)[nH]c2c(Br)ccc(Cl)c2c1=O] | 3-acetyl-2-(((6-aminopyridin-3-yl)methyl)sulfinyl)-8-bromo-5-chloroquinolin-4(1H)-one |

TABLE 3-continued

| Compound No. | Structure | IUPAC Name |
|---|---|---|
| 101 | 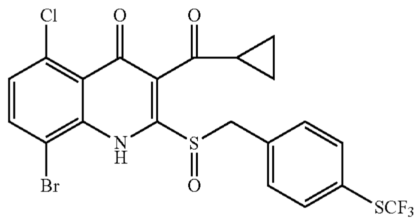 | 8-bromo-5-chloro-3-(cyclopropanecarbonyl)-2-((4-((trifluoromethyl)thio)benzyl)sulfinyl)quinolin-4(1H)-one |
| 102 | 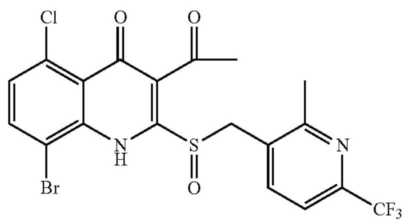 [SMILES: CC(=O)c1c(S(=O)Cc2ccc(C(F)(F)F)nc2C)[nH]c2c(Br)ccc(Cl)c2c1=O] | 3-acetyl-8-bromo-5-chloro-2-(((2-methyl-6-(trifluoromethyl)pyridin-3-yl)methyl)sulfinyl)quinolin-4(1H)-one |
| 103 | 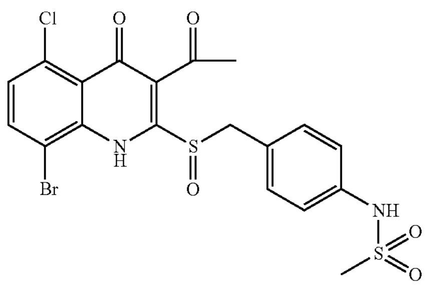 [SMILES: CC(=O)c1c(S(=O)Cc2ccc(NS(C)(=O)=O)cc2)[nH]c2c(Br)ccc(Cl)c2c1=O] | N-(4-(((3-acetyl-8-bromo-5-chloro-4-oxo-1,4-dihydroquinolin-2-yl)sulfinyl)methyl)phenyl)methanesulfonamide |
| 104 | 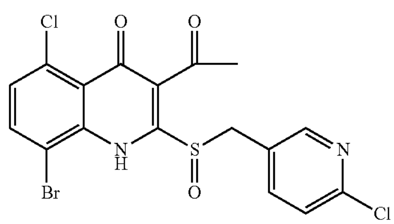 [SMILES: CC(=O)c1c(S(=O)Cc2ccc(Cl)nc2)[nH]c2c(Br)ccc(Cl)c2c1=O] | 3-acetyl-8-bromo-5-chloro-2-(((6-chloropyridin-3-yl)methyl)sulfinyl)quinolin-4(1H)-one |
| 105 | 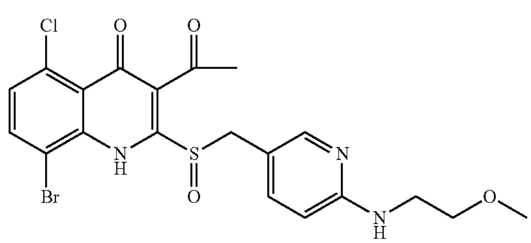 [SMILES: COCCNc1ccc(CS(=O)c2[nH]c3c(Br)ccc(Cl)c3c(=O)c2C(C)=O)cn1] | 3-acetyl-8-bromo-5-chloro-2-(((6-((2-methoxyethyl)amino)pyridin-3-yl)methyl)sulfinyl)quinolin-4(1H)-one |
| 106 | 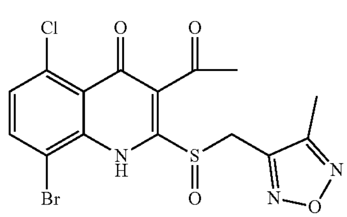 [SMILES: CC(=O)c1c(S(=O)Cc2nonc2C)[nH]c2c(Br)ccc(Cl)c2c1=O] | 3-acetyl-8-bromo-5-chloro-2-(((4-methyl-1,2,5-oxadiazol-3-yl)methyl)sulfinyl)quinolin-4(1H)-one |

TABLE 3-continued

| Compound No. | Structure | IUPAC Name |
|---|---|---|
| 107 | 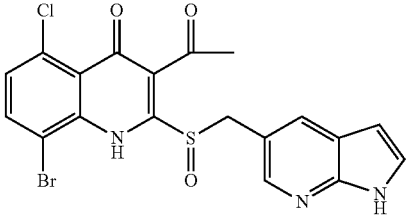 [SMILES: CC(=O)c1c(S(=O)Cc2cnc3[nH]ccc3c2)[nH]c2c(Br)ccc(Cl)c2c1=O] | 2-(((1H-pyrrolo[2,3-b]pyridin-5-yl)methyl)sulfinyl)-3-acetyl-8-bromo-5-chloroquinolin-4(1H)-one |

In another aspect, the present invention provides a pharmaceutical composition for treating or preventing cancer, containing a therapeutically effective amount of a compound of Formula 1, 2, or 3 according to the present invention or a pharmaceutically acceptable salt thereof, and a pharmaceutically acceptable carrier.

In still another aspect, the present invention provides a pharmaceutical composition for treating or preventing cancer, containing a therapeutically effective amount of the compound of Formula 1, 2 or 3 according to the present invention or a pharmaceutically acceptable salt thereof, a pharmaceutically acceptable carrier, and a therapeutically effective amount of an active pharmaceutical ingredient selected from the group consisting of another anticancer agent other than the compound of the present invention, a cytostatic drug, an angiogenesis inhibitor, a kinase inhibitor, a cytokine blocker, and a cell adhesion molecule inhibitor.

In yet another aspect, the present invention provides a method for treating a disease or condition, including a step of administering a therapeutically effective amount of a compound of Formula 1, 2, or 3 or a pharmaceutically acceptable salt thereof to a subject in need thereof, in which the disease or the condition is cancer, neoplasia, or a tumor including lung cancer (including small cell lung cancer and non-small cell lung cancer), colorectal cancer, colon cancer, rectal cancer, breast cancer, prostate cancer, bladder cancer, blood cancer, leukemia, myelogenous leukemia, lymphoma, cervical carcinoma, osteosarcoma, glioblastoma, melanoma, pancreatic cancer, gastric cancer, liver cancer, renal cancer, gallbladder cancer, bile duct cancer, esophageal cancer, ovarian cancer, neuroblastoma, and the like. In yet another aspect, the subject is a human. In yet another aspect, the disease or condition is bladder cancer. In yet another aspect, the disease or condition is prostate cancer. In yet another aspect, the disease or condition is lung cancer. In yet another aspect, the disease or condition is breast cancer. In yet another aspect, the disease or condition is blood cancer. In yet another aspect, the disease or condition is pancreatic cancer. In yet another aspect, the disease or condition is colorectal cancer. In yet another aspect, the disease or condition is glioblastoma. In yet another aspect, the disease or condition is neuroblastoma. In yet another aspect, the disease or condition is melanoma. In yet another aspect, the disease or condition is liver cancer. In yet another aspect, the disease or condition is cervical carcinoma. In yet another aspect, the disease or condition is renal cancer.

That is, the present invention provides a medical use of using, as an active ingredient, the compound of Formula 1, 2, or 3 or a pharmaceutically acceptable salt thereof. In an aspect, the medical use of the present invention is a use of treating or preventing the disease or condition described in the present specification.

The present invention further provides a method for treating the following disease or condition in a subject having or likely to have the following disease or condition by administering a therapeutically effective amount of one or more of the aforementioned compound to the subject. In an aspect, the treatment is preventative treatment. In another aspect, the treatment is palliative treatment. In still another aspect, the treatment is restorative treatment.

The compounds for inhibiting the formation of a c-Myc/Max/DNA complex of the present invention are useful for various therapeutic or preventative uses (for example, antitumor). These compounds may be used to inhibit c-Myc mediated cell activity and may also be used to treat a tumor or cancer or to prevent deterioration of these diseases. Accordingly, the present invention provides a method for inhibiting intracellular c-Myc mediated biochemical activity or a c-Myc signaling pathway. In the method, the cells are brought into contact with an effective amount of the compound of the present invention. In an embodiment, the cells are present in a subject (for example, a patient with cancer). In an embodiment, the present invention provides a therapeutic use of preventing tumor progression or treating cancer in a subject by using the compound of the present invention. The method of the present invention includes administering a pharmaceutical composition including a therapeutically or preventatively effective amount of an inhibitor of the formation of the c-Myc/Max/DNA complex to a subject in need of treatment or prevention.

In an embodiment, the present invention provides a method for inhibiting a c-Myc signaling pathway in tumor or cancer cells. For example, the present invention may be used to suppress lung cancer (including small cell lung cancer and non-small cell lung cancer), colorectal cancer, colon cancer, rectal cancer, breast cancer, prostate cancer, bladder cancer, blood cancer, leukemia, myelogenous leukemia, lymphoma, cervical carcinoma, osteosarcoma, glioblastoma, melanoma, pancreatic cancer, gastric cancer, liver cancer, renal cancer, gallbladder cancer, bile duct cancer, esophageal cancer, ovarian cancer, neuroblastoma, and the like from forming a c-Myc/Max/DNA complex in cells. In the method, the present invention provides a method for suppressing growth or proliferation of cells, particularly, tumor or cancer cells, in a subject. In the method, the cancer cells are present in in vivo state in a subject. The compound of the present invention may be administered in a form of a pharmaceutical composition described in the present specification to the subject.

In an embodiment, the present invention provides a method for treating or preventing cancer or a tumor in a subject, and examples of the cancer include lung cancer (including small cell lung cancer and non-small cell lung cancer), colorectal cancer, colon cancer, rectal cancer, breast cancer, prostate cancer, bladder cancer, blood cancer, leukemia, myelogenous leukemia, lymphoma, cervical carcinoma, osteosarcoma, glioblastoma, melanoma, pancreatic cancer, gastric cancer, liver cancer, renal cancer, gallbladder cancer, bile duct cancer, esophageal cancer, ovarian cancer, and neuroblastoma. The method includes administering, to a subject in need of treatment, an amount sufficient to inhibit formation of the c-Myc/Max/DNA complex, that is, a therapeutically effective amount of the compound of the present invention.

The cancer and tumor suitable for being treated by the composition and method of the present invention may be diverse depending on the tissue and organ. Examples of the cancer and tumor include a brain tumor (glioblastoma multiforme, and the like), a spinal tumor, maxillary sinus cancer, pancreatic cancer, pancreatic acinar cancer, gum cancer, tongue cancer, lip cancer, nasopharyngeal cancer, hypopharyngeal cancer, laryngeal cancer, thyroid cancer, parathyroid cancer, lung cancer, pleural tumor, cancerous peritonitis, cancerous pleuritic, esophageal cancer, gastric cancer, colorectal cancer, bile duct cancer, gallbladder cancer, liver cancer, renal cancer, gallbladder cancer, prostate cancer, penile cancer, testicular tumor, cancer of the adrenal gland, uterocervical cancer, endometrial cancer, vaginal cancer, vulvar cancer, ovarian cancer, ciliated epithelial cancer, a malignant bone tumor, soft-tissue sarcoma, breast cancer, skin cancer, malignant melanoma, a basal cell tumor, leukemia, myelogenous leukemia, myelofibrosis (particularly myelofibrosis with myeloid metaplasia, lymphoma, Hodgkin's disease, plasmacytoma, and glioma, but are not limited thereto.

In an embodiment, the cancer and tumor include lung cancer (including small cell lung cancer and non-small cell lung cancer), colorectal cancer, colon cancer, rectal cancer, breast cancer, prostate cancer, bladder cancer, blood cancer, leukemia, myelogenous leukemia, lymphoma, cervical carcinoma, osteosarcoma, glioblastoma, melanoma, pancreatic cancer, gastric cancer, liver cancer, renal cancer, gallbladder cancer, bile duct cancer, esophageal cancer, ovarian cancer, or neuroblastoma.

In another embodiment, the cancer is bladder cancer.

In another aspect, the cancer is prostate cancer, and the prostate cancer may be hormone-dependent or hormone-independent prostate cancer.

In still another aspect, the cancer is lung cancer, and the lung cancer may be small cell or non-small cell lung cancer.

In yet another aspect, the cancer is breast cancer, and the breast cancer may be HER2-receptor positive or triple-negative breast cancer.

In yet another aspect, the cancer is blood cancer, and the blood cancer may be selected from the group consisting of acute and chronic leukemia, lymphoma, multiple myeloma, and myelodysplastic syndrome.

In yet another aspect, the cancer is pancreatic cancer, and the pancreatic cancer may be a pancreatic cystic tumor or malignant pancreatic tumor.

In yet another aspect, the cancer is colorectal cancer, and the colorectal cancer may be selected from the group consisting of glandular cancer, lymphoma, malignant carcinoid, and leiomyosarcoma occurring in the large intestine.

In yet another aspect, the disease or condition is glioblastoma, and the glioblastoma may be neuroglioma, meningioma, pituitary adenoma, a metastatic brain tumor, and acoustic neurinoma.

In yet another aspect, the disease or condition is neuroblastoma, and the neuroblastoma may be neuroblastoma, ganglioneuroblastoma, and gangliocytoma.

In yet another aspect, the disease or condition is melanoma, and the melanoma may be acral lentiginous melanoma, nodular melanoma, superficial spreading melanoma, and lentigo maligna melanoma.

In yet another aspect, the disease or condition is liver cancer, and the liver cancer may be hepatocellular carcinoma, cholangiocarcinoma, hepatoblastoma, and angiosarcoma.

In yet another aspect, the disease or condition is uterine cancer, and the uterine cancer may be cervical carcinoma, endometrial cancer, and uterine sarcoma.

In yet another aspect, the disease or condition is renal cancer, and the renal cancer may be clear cell type renal cell cancer, papillary renal cell cancer, anaerobic dye renal cell cancer, and collecting duct renal cell cancer.

A suitable subject to be treated according to the present invention includes a mammalian subject. The mammal according to the present invention is not limited to, but includes humans, canines, felines, bovines, caprines, equines, ovines, swine, rodents, lagomorphs, primates, and the like, and includes a mammal in utero. The subject may be either gender and may be any step of development.

In an aspect, the suitable subject to be treated according to the present invention is a human.

The compound of the present invention is generally administered in a therapeutically effective amount.

The compound of the present invention can be administered by any suitable route in the form of a pharmaceutical composition suitable for the route, and in an effective dose for a desired treatment. The effective dose may be generally about 0.001 to about 100 mg/kg of body weight/day, preferably about 0.01 to about 30 mg/kg of body weight/day as a single or divided dose. Depending on the age, species, and disease or condition to be treated, a dose level less than the lower limit of the above range may be suitable. In other cases, a larger dose may be still used without harmful side effects. The larger dose may be divided into several small doses for daily administration. Methods for determining an appropriate dose are well known in the art to which the present invention pertains, and for example, the document Remington: The Science and Practice of Pharmacy, Mack Publishing Co., $20^{th}$ ed., 2000 may be referenced.

For the treatment of the disease or condition described above, the compound described in the present specification or a therapeutically acceptable salt thereof may be administered as follows.

The compound of the present invention may be administered into the mouth, and the mouth is a concept including swallowing. The compound of the present invention may enter the gastrointestinal tract by oral administration, or may be directly absorbed from the mouth into the bloodstream, for example, as in buccal or sublingual administration.

A composition suitable for oral administration may be in the form of a solid, liquid, gel, or powder, and may have a dosage form such as a tablet, a lozenge, a capsule, a granule, and a powder.

A composition for oral administration may optionally be enterically coated, and may exhibit delayed or sustained release through the enteric coating. That is, the composition for oral administration according to the present invention may be a dosage form having an immediate or modified release pattern.

A liquid dosage form may include a solution, a syrup, and a suspension, and the liquid composition may be in a form of being contained in a soft or hard capsule. This dosage form may include a pharmaceutically acceptable carrier, for example, water, ethanol, polyethylene glycol, cellulose, or oil. The dosage form may also include one or more emulsifiers and/or suspending agents.

In a tablet dosage form, a drug which is an active agent may be present in an amount of about 0.05 wt % to about 95 wt % based on the total weight of the tablet, and may be more generally present in an amount of about 2 wt % to about 50 wt % of the dosage form. Further, the tablet may contain a disintegrant which is included in an amount of about 0.5 wt % to about 35 wt %, more generally, about 2 wt % to about 25 wt % of the dosage form. As an example of the disintegrant, lactose, starch, sodium starch glycolate, crospovidone, croscarmellose sodium, maltodextrin, or a mixture thereof may be used, but the example is not limited thereto.

A suitable glidant included for preparation of a tablet may be present in an amount of about 0.1 wt % to about 5 wt %, talc, silicon dioxide, stearic acid, calcium, zinc or magnesium stearate, sodium stearyl fumarate, and the like may be used as the glidant, but the present invention is not limited to these types of additives.

As a binder for preparing a tablet, gelatin, polyethylene glycol, sugar, gum, starch, polyvinyl pyrrolidone, hydroxypropyl cellulose, hydroxypropyl methyl cellulose, and the like may be used, and as a diluent suitable for preparing a tablet, mannitol, xylitol, lactose, dextrose, sucrose, sorbitol, starch, microcrystalline cellulose, and the like may be used, but the present invention is not limited to these types of additives.

Optionally, a solubilizer to be included in the tablet may be used in an amount of about 0.1 wt % to about 3 wt % based on the total weight of the tablet, and for example, polysorbate, sodium lauryl sulfate, sodium dodecyl sulfate, propylene carbonate, diethylene glycol monoethyl ether, dimethylisosorbide, polyoxyethylene glycolated natural or hydrogenated castor oil, HCOR™ (Nikkol), oleyl ester, Gelucire™, caprylic/capric acid mono/diglyceride, sorbitan fatty acid ester, Solutol HS™, and the like may be used in the pharmaceutical composition according to the present invention, but the present invention is not limited to these specific types of solubilizer.

The compound of the present invention may be administered directly into the bloodstream, muscle, or internal organs. A suitable method for parenteral administration includes intravenous, intra-muscular, subcutaneous intraarterial, intraperitoneal, intrathecal, intracranial injections, and the like. A suitable device for parenteral administration includes a syringe (injector)(including needle and needle-free syringes) and an infusion method.

A composition for parenteral administration may be a dosage form having an immediate or modified release pattern, and the modified release pattern may be a delayed or sustained release pattern.

Most of the parenteral dosage forms are liquid compositions, and the liquid composition is an aqueous solution including a medicinal ingredient according to the present invention, a salt, a buffer, an isotonic agent, and the like.

The parenteral dosage form may also prepared in a dried form (for example, lyophilized) or as a sterile non-aqueous solution. These dosage forms may be used with a suitable vehicle such as sterile water. A solubility-enhancing agent may also be used for the preparation of a parenteral solution.

The compound of the present invention may be administered topically onto the skin or transdermally. The dosage form for topical administration includes a lotion, solution, cream, gel, hydrogel, ointment, foam, implant, patch, and the like. A pharmaceutically acceptable carrier for topical administration dosage form may include water, an alcohol, mineral oil, glycerin, polyethylene glycol, and the like. The topical administration may also be performed by electroporation, iontophoresis, phonophoresis, and the like.

A composition for topical administration may be a dosage form having an immediate or modified release pattern, and the modified release pattern may be a delayed or sustained release pattern.

A method for preparing a pharmaceutical composition for appropriately treating or preventing a disease or condition is well known to a person with ordinary skill in the art to which the present invention pertains. For example, according to the those described in *Handbook of Pharmaceutical Excipients* ($7^{th}$ ed.), *Remington: The Science and Practice of Pharmacy* ($20^{th}$ ed.), *Encyclopedia of Pharmaceutical Technology* ($3^{rd}$ ed.), *Sustained and Controlled Release Drug Delivery Systems* (1978), and the like, a pharmaceutical composition for the object of the present invention may be prepared by appropriately mixing a pharmaceutically acceptable carrier, a vehicle, additives, and the like with the compound according to the present invention.

The compound of the present invention may be used alone or in combination with another pharmaceutically active compound to treat the condition as described above. The compound(s) of the present invention and (an)other pharmaceutically active compound(s) may be administered simultaneously (in the same dosage form or in separate dosage forms) or sequentially. Accordingly, in an aspect, the present invention includes a method for treating a condition by administering, to a subject, a therapeutically effective amount of the compound of the present invention and one or more additional pharmaceutically active compounds.

In another aspect, provided is a pharmaceutical composition containing one or more compounds of the present invention, one or more additional pharmaceutically active compounds, and a pharmaceutically acceptable carrier.

In still another aspect, the one or more additional pharmaceutically active compounds are an anticancer agent. For example, the anticancer agent is an EGFR kinase inhibitor, MEK inhibitor, VEGFR inhibitor, anti-VEGFR2 antibody, KDR antibody, AKT inhibitor, PDK-1 inhibitor, PI3K inhibitor, c-kit/Kdr tyrosine kinase inhibitor, Bcr-Abl tyrosine kinase inhibitor, VEGFR2 inhibitor, PDGFR-beta inhibitor, KIT inhibitor, Flt3 tyrosine kinase inhibitor, PDGF receptor family inhibitor, RET tyrosine kinase receptor family inhibitor, VEGF-3 receptor antagonist, Raf protein kinase family inhibitor, angiogenesis inhibitor, Erb2 inhibitor, mTOR inhibitor, IGF-1R antibody, NFkB inhibitor, proteasome inhibitor, chemotherapy agent, or glucose reduction agent.

In an embodiment, a medicinal ingredient used for the complex and/or combination treatment according to the present invention together with the compound of the present invention is an anticancer agent. That is, the specific compound according to the present invention may be administered simultaneously or sequentially to a subject receiving chemotherapy including one or more anticancer agents. Examples of the anticancer agent include alkylating agents including nitrogen mustard, chlorambucil, cyclophosphamide (cytoxan), ifosfamide, melphalan, thiptepa and busulfan; antimetabolites including methotrexate, 5-fluorouracil, cytoxin arabinoside (ara-C), 5-azacytidine, 6-mercaptopurine, 6-thioguanine, and fludarabine phosphate; antitumor antibiotics including todoxorubicin (adriamycin), daunorubicin, dactinomycin, bleomycin, mitomycin C, plicamycin, idarubicin, and mitoxantrone; vinca alkaloids and epipodophyllotoxins including vincristine, vinblastine, vindesine, etoposide, and teniposide; nitrosoureas including carmustine, lomustine, semustine and streptozocin; synthetic drugs including Dacrabazine, hexamethylmelamine, hydroxyurea, mitotane procabazine, cisplatin, cisplatinum, and carboplatin; liquid therapeutic agents including corticosteroids (cortisone acetate, hydrocortisone, prednisone, prednisolone, methyl prednisolone and dexamethasone), estrogens (diethylstibesterol, estradiol, esterified estrogens, conjugated estrogens, chlorotiasnene), progestins (medroxyprogesterone acetate, hydroxy progesterone caproate, megestrol acetate), antiestrogens (tamoxifen), aromastase inhibitors (aminoglutethimide), androgens (testosterone propionate, methyltestosterone, fluoxymesterone, testolactone), antiandrogens (flutamide), LHRH analogues (leuprolide acetate), and endocrines for prostate cancer (ketoconazole), but the present invention is not limited to these types of second active agent.

In an embodiment, the anticancer agent used for the complex and/or combination treatment according to the present invention together with the compound of the present invention is a therapeutic agent for bladder cancer. In an embodiment, the therapeutic agent for bladder cancer is gemcitabine, paclitaxel, doxorubicin, and/or mitomycin C. When the compound of the present invention is used with another therapeutic agent for bladder cancer, a topical treatment method by a drug injection therapy in the bladder for treatment of non-muscle invasive bladder cancer may be used in the compound of the present invention.

In an embodiment, the anticancer agent used for the complex and/or combination treatment according to the present invention together with the compound of the present invention is a therapeutic agent for prostate cancer. In an embodiment, the therapeutic agent for prostate cancer is enzalutamide, satraplatin (SPARC trial), cabazitaxel (TROPIC trial), abiraterone acetate (COU-AA-301), and/or MDV3100.

In an embodiment, the anticancer agent used for the complex and/or combination treatment according to the present invention together with the compound of the present invention is a therapeutic agent for blood cancer. In an embodiment, the therapeutic agent for blood cancer is enzalutamide, satraplatin (SPARC trial), cabazitaxel (TROPIC trial), abiraterone acetate (COU-AA-301), and/or MDV3100.

In an embodiment, the anticancer agent used for the complex and/or combination treatment according to the present invention together with the compound of the present invention is a therapeutic agent for pancreatic cancer. In an embodiment, the therapeutic agent for pancreatic cancer is gemcitabine, erlotinib, capecitabine, a platinum-based drug, 5-FU, capecitabine, or tegafur/gemeracil/oteracil.

In an embodiment, the anticancer agent used for the complex and/or combination treatment according to the present invention together with the compound of the present invention is a therapeutic agent for colorectal cancer. In an embodiment, the therapeutic agent for colorectal cancer is a fluoropyrimidine-based drug such as 5-fluorouracil, tegafururacil (UFT), and capecitabine, irinotecan, oxaliplatin, bevacizumab (trade name Avastin), cetuximab (trade name Erbitux), regorafenib (trade name Stivarga), and aflibercept (trade name Zaltrap).

When the compound of the present invention is used as a medicinal ingredient in the complex, the therapeutically effective dose may vary. The combination treatment may further include periodic treatment that starts and stops at various times to aid in the clinical management of a patient. In any case, the multiple therapeutic agents (one of which is a c-Myc/Max/DNA complex formation inhibitor as described in the present application) are administered in any order or simultaneously. When administered simultaneously, the multiple therapeutic agents are arbitrarily provided alone, in a unified form, or in a multiple form (as an example, as one pill or two separate pills).

In an aspect, one of the therapeutic agents is given in multiple doses or both of the therapeutic agents are given in multiple doses. When the multiple therapeutic agents are not simultaneously administered, the time between multiple doses may vary arbitrarily from more than 0 weeks to less than 20 weeks.

Further, the combination method, the composition, and the dosage form are not limited to the use of only two preparations, and a combination of multiple treatments is also conceived. A dosage regimen for treating, preventing, or ameliorating a pathological condition(s) may be arbitrarily changed depending on various factors. These factors include not only the age, body weight, sex, diet, and medical condition of a subject, but also the disorder that the subject is suffering from.

A pharmaceutical preparation constituting the combination treatment disclosed in the present specification is any combined dosage form or a typically separate dosage form for simultaneous administration. The pharmaceutical preparation constituting the combination treatment can also be administered sequentially with any one of the preparations to be administered by a regimen requiring a two-step administration. The two-step dosage regimen may require an active agent to be sequentially administered or a separate active agent to be separately administered. The time period between the multiple administration steps ranges from several minutes to several hours depending on the characteristics of each pharmaceutical preparation such as potency, solubility, bioavailability, plasma half-life, and kinetic profile of the pharmaceutical preparation. The circadian variation of the target molecule concentration is used to determine the optimal administration interval.

Hereinafter, the present invention will be described in detail with reference to Examples and the like to help understanding of the present invention. However, the Examples according to the present invention may be modified into various forms, and it shall not be interpreted that the scope of the present invention is limited to the following Examples. The Examples of the present invention are provided for more completely explaining the present invention to the person with ordinary skill in the art to which the present invention pertains.

EXAMPLES

Example 1. Preparation of a Compound Used as an Active Ingredient of the Present Invention The reagents and solvents used below can be purchased from Aldrich Chemical Co. (Milwaukee, Wis., USA). The $^1$H-NMR spectrum was measured by using a Varian Gemini 400 MHz NMR spectrometer.

Example 2. Preparation of 3-acetyl-8-bromo-5-chloro-2-(methylthio)quinolin-4(1H)-one (4a), 3-acetyl-2-(benzylthio)-8-bromo-5-chloroquinolin-4(1H)-one (4b), 3-acetyl-8-bromo-5-chloro-2-(methylsulfinyl)quinolin-4(1H)-one (5a), and 3-acetyl-2-(benzylsulfinyl)-8-bromo-5-chloroquinolin-4(1H)-one (5b)

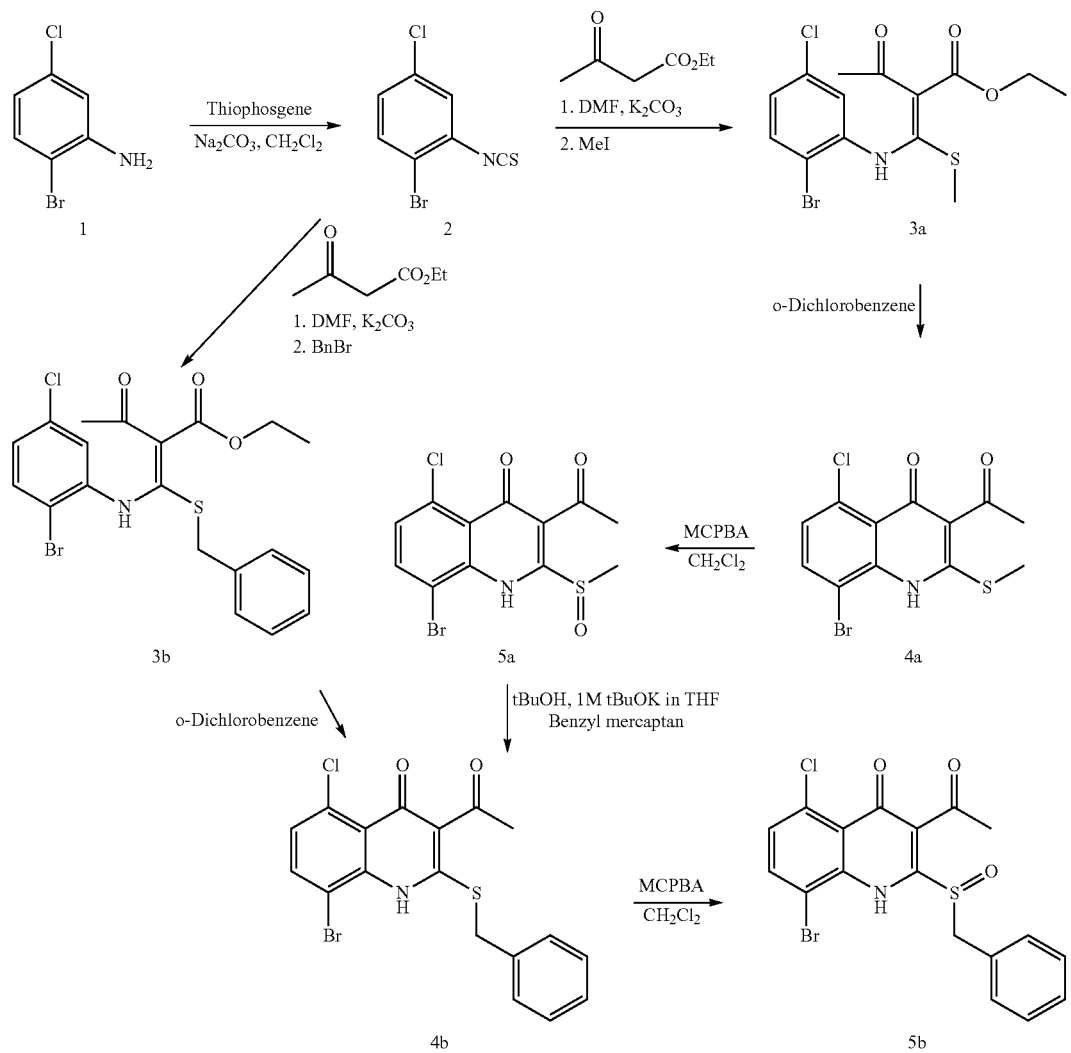

2-1. Synthesis of 2-bromo-5-chlorophenyl isothiocyanate (Isothiocyanate Formation)

After 2-bromo-5-chloroaniline 1 (10 g, 48.5 mmol) was dissolved in anhydrous dichloroethane (CH$_2$Cl$_2$, 250 mL), sodium carbonate (Na$_2$CO$_3$, 11 g, 97 mmol) was put thereinto. In a state where the solution was cooled to 5° C. by using ice water under a nitrogen gas, thiophosgene (5.5 mL, 72.7 mmol) was very slowly added thereto. After the reaction solution was stirred at room temperature for 12 hours, inorganic materials were removed by filtering the reaction solution. After the solvent was removed by distillation under reduced pressure, hexane (n-hexane, 50 mL) was added to the produced solid, the resulting mixture was stirred for 10 minutes and then filtered, and the title compound, which is a yellow solid, was quantitatively obtained as a product.

$^1$H NMR (300 MHz, CDCl$_3$) δ 7.51-7.49 (d, J=8.61 Hz, 1H), 7.26-7.25 (d, J=2.4 Hz, 1H), 7.13-7.09 (dd, J=2.46, 6.18 Hz, 1H).

LC/MS data: 249.52 g/mol

2-2. Synthesis of ethyl (Z)-2-(((2-bromo-5-chlorophenyl)amino)(methylthio)methylene)-3-oxobutanoate 3a (C═C Bond Formation)

After the isothiothianate 2 (10 g, 40 mmol) synthesized in Step 1 was dissolved in anhydrous DMF (20 mL), the solution was slowly added to a solution in which ethyl oxobutanoate (5.2 g, 40 mmol) and K$_2$CO$_3$ (5.6 g, 40 mmol) were dissolved in DMF (100 mL) at room temperature. After the solution was stirred at room temperature for 12 hours, iodomethane (5.7 g, 40 mmol) was slowly added thereto at room temperature. Thereafter, the solution was stirred at room temperature for a day. After it was confirmed by TLC that the reaction was completed, water and ethyl acetate were put thereinto, and a desired compound was extracted with an organic layer. After water of the extracted organic layer was removed using MgSO$_4$ and the resulting product was distilled under reduced pressure, purification was performed by using column chromatography to obtain the title compound 3a.

$^1$H NMR (300 MHz, CDCl$_3$) δ 12.90 (s, 1H), 7.45-7.42 (d, J=8.41 Hz, 1H), 6.90-6.86 (d, J=7.74 Hz, 1H), 6.68 (s, 1H), 4.36-4.29 (m, 2H), 2.54 (s, 3H), 2.04 (s, 3H), 1.37-1.33 (t, J=7.26 Hz, 3H).

LC/MS data: 393.69 g/mol

2-3. Synthesis of 3-acetyl-8-bromo-5-chloro-2-(methylthio)quinolin-4(1H)-one 4a (Cyclization)

After the compound 3a synthesized in Step 2 was dissolved in o-dichlorobenzene, the resulting solution was stirred for 12 hours while being heated at 180° C. After the reaction was completed, the product was cooled to room temperature and purified under reduced pressure. After hexane was added to the produced solid, the resulting mixture was stirred for 10 minutes and then filtered to synthesize a desired compound 4a.

$^1$H NMR (300 MHz, CDCl$_3$) δ 8.67 (s, 1H), 7.91-7.88 (d, J=8.19 Hz, 1H), 7.71-7.68 (d, J=8.49 Hz, 1H), 2.97 (s, 3H), 2.79 (s, 3H).

LC/MS data: 347.62 g/mol

2-4. Synthesis of 3-acetyl-8-bromo-5-chloro-2-(methylsulfinyl)quinolin-4(1H)-one 5a (Oxidation)

The quinoline 4a obtained in Step 3 was oxidized under anhydrous dichloroethane (CH$_2$Cl$_2$, 10 mL) by using MCPBA (1.5 eq.) to obtain the title compound 5a.

$^1$H NMR (300 MHz, CDCl$_3$) δ 11.13 (s, 1H), 7.82-7.79 (d, J=8.43 Hz, 1H), 7.38-7.36 (d, J=8.46 Hz, 1H), 3.02 (s, 3H), 2.78 (s, 3H).

LC/MS data: 363.62 g/mol

2-5. Synthesis of ethyl (Z)-2-((benzylthio)((2-bromo-5-chlorophenyl)amino)methylene)-3-oxobutanoate 3b The title compound 3b was synthesized by using benzyl bromide instead of MeI in a manner similar to the case where 3a was synthesized.

$^1$H NMR (300 MHz, CDCl$_3$) δ 12.90 (s, 1H), 7.46-7.44 (m, 2H), 7.35-7.24 (m, 4H), 6.91-6.89 (d, J=7.95 Hz, 1H), 6.70 (s, 1H), 4.49-4.19 (m, 4H), 2.05 (s, 3H), 1.36-1.31 (t, J=7.11 Hz, 3H).

LC/MS data: 469.79 g/mol

2-6. Synthesis of 3-acetyl-2-(benzylthio)-8-bromo-5-chloroquinolin-4(1H)-one 4b The title compound 4b was synthesized in a manner similar to the case where 4a was synthesized.

$^1$H NMR (300 MHz, CDCl$_3$) δ 8.59 (s, 1H), 7.93-7.90 (d, J=8.25 Hz, 1H), 7.52-7.47 (m, 2H), 7.42-7.21 (m, 4H), 4.80 (s, 2H), 2.93 (s, 3H).

LC/MS data: 423.72 g/mol

2-7. Synthesis of 3-acetyl-2-(benzylsulfinyl)-8-bromo-5-chloroquinolin-4(1H)-one 5b The title compound 5b was synthesized in a manner similar to the case where 5a was synthesized.

The following compounds according to the present invention were synthesized by appropriately changing the reactants and/or the starting materials using the mentioned method, and the LC/MS and $^1$H NMR measurement results are summarized and shown in the following Table 4. In the following Table 4, MW means an average molecular weight, and MS is a value obtained by analyzing the actually prepared compound.

TABLE 4

| Compound No. | Formula Name | MW (molecular weight) | LC/MS data | $^1$H NMR |
|---|---|---|---|---|
| 1 | 3-acetyl-8-bromo-5-chloro-2-(methylsulfinyl)quinolin-4(1H)-one | 362.62 | 363 | $^1$H NMR (300 MHz, CDCl$_3$)δ11.13 (br, 1H), 7.81 (d, J = 8.4 Hz, 1H), 7.37 (d, J = 8.4 Hz, 1H), 3.02 (s, 3H), 2.78 (s, 3H). |
| 2 | 3-acetyl-8-bromo-5-chloro-2-(methylthio)quinolin-4(1H)-one | 346.63 | 348 | $^1$H NMR (300 MHz, CDCl$_3$)δ8.67(s, 1H), 7.91-7.88(d, J = 8.19 Hz, 1H), 7.71-7.68(d, J = 8.49 Hz, 1H), 2.97(s, 3H), 2.79(s, 3H). |
| 3 | 3-acetyl-2-(benzylthio)-8-bromo-5-chloroquinolin-4(1H)-one | 422.72 | 423 | $^1$H NMR (300 MHz, CDCl$_3$)δ16.43 (s, 0.5H), 8.59 (br, 0.5H), 7.91 (d, J = 8.3 Hz, 1H), 7.62 (d, J = 8.4 Hz, 0.5H), 7.48 7.52 (m, 3H), 7.27 7.43 (m, 5H), 7.22 (d, J = 8.4 Hz, 0.5H), 4.80 (s, 2H), 4.32 (s, 1H), 2.93 (s, 3H), 2.69 (s, 1.5H). |
| 4 | 3-acetyl-2-(benzylsulfinyl)-8-bromo-5-chloroquinolin-4(1H)-one | 438.72 | 439 | $^1$H NMR (300 MHz, CDCl$_3$)δ10.24 (br, 1H), 7.67 (d, J = 8.4 Hz, 1H), 7.29 (d, J = 8.4 Hz, 1H), 7.13 7.22 (m, 3H), 7.08 7.11 (m, 2H), 4.59 4.25 (m, 2H), 2.84 (s, 3H). |
| 5 | 3-acetyl-8-bromo-5-chloro-1-methyl-2-(methylthio)quinolin-4(1H)-one | 360.65 | 360 | $^1$H NMR (300 MHz, CDCl$_3$)δ7.92-7.89(d, J = 8.22 Hz, 1H), 7.36-7.33(d, J = 8.13 Hz, 1H), 3.89(s, 3H), 2.74(s, 3H), 2.65(s, 3H). |
| 6 | 3-acetyl-5,8-dichloro-2-(methylsulfinyl)quinolin-4(1H)-one | 318.17 | 318 | $^1$H NMR (300 MHz, CDCl$_3$)δ11.07(s, 1H), 7.67-7.64(d, J = 8.46 Hz, 1H), 7.44-7.41(d, J = 8.46 Hz, 1H), 3.02(s, 3H), 2.78(s, 3H). |

TABLE 4-continued

| Compound No. | Formula Name | MW (molecular weight) | LC/MS data | $^1$H NMR |
|---|---|---|---|---|
| 7 | 3-acetyl-6-fluoro-1-methyl-2-(methylthio)quinolin-4(1H)-one | 265.30 | 266 | $^1$H NMR (300 MHz, CDCl$_3$)δ7.92-7.87(q, J = 5.1, 3.99 Hz, 1H), 7.69-7.65(q, J = 2.88, 6.45 Hz, 1H), 7.48-7.39(m, 1H), 4.53-4.46(q, J = 7.14, 7.14 Hz, 2H), 4.08(s, 3H), 3.66(s, 3H), 1.48-1.44(t, J = 7.14 Hz, 3H). |
| 8 | 1-(6-fluoro-4-hydroxy-2-(methylthio)quinolin-3-yl)ethan-1-one | 251.28 | 252 | $^1$H NMR (300 MHz, CDCl$_3$)δ7.83-7.78(m, 2H), 7.49-7.42(m, 1H), 4.59-4.52(q, J = 7.14 Hz, 2H), 2.58(s, 3H), 1.56-1.51(t, J = 7.14 Hz, 3H). |
| 9 | 3-acetyl-8-bromo-1-(4-bromobenzoyl)-5-chloro-2-(methylthio)quinolin-4(1H)-one | 545.63 | 544 | $^1$H NMR (300 MHz, CDCl$_3$)δ8.09-8.07(d, J = 5.73 Hz, 1H), 8.06-8.04(d, J = 6.15 Hz, 2H), 7.73-7.70(d, J = 8.58 Hz, 2H), 7.56-7.54(d, J = 8.22 Hz, 1H), 3.15(s, 3H), 2.63(s, 3H). |
| 10 | 3-acetyl-8-bromo-5-chloro-2-((4-chlorobenzyl)thio)quinolin-4(1H)-one | 457.16 | 456 | $^1$H NMR (300 MHz, DMSO) δ 7.65-7.62(d, J = 8.13 Hz, 1H), 7.45-7.42(d, J = 6.69 Hz, 2H), 7.29-7.26(d, J = 8.34 Hz, 2H), 6.91-6.88(d, J = 8.19 Hz, 1H), 4.44(s, 2H), 2.40(s, 3H). |
| 11 | 3-acetyl-8-bromo-5-chloro-2-((4-chlorobenzyl)sulfinyl)quinolin-4(1H)-one | 473.16 | 472 | $^1$H NMR (300 MHz, CDCl$_3$)δ10.21(s, 1H), 7.73-7.71(d, J = 8.43 Hz, 1H), 7.33-7.31(d, J = 8.37 Hz, 1H), 7.18-7.15(d, J = 9 Hz, 2H), 7.05-7.03(d, J = 8.25 Hz, 2H), 4.37(s, 2H), 2.84(s, 3H). |
| 12 | 3-acetyl-8-bromo-5-chloro-2-(phenylthio)quinolin-4(1H)-one | 408.69 | 408 | $^1$H NMR (300 MHz, MeOD) δ 7.51-7.48(m, 2H), 7.46-7.43(d, J = 8.11 Hz, 1H), 7.31-7.28(d, J = 7.71 Hz, 3H), 6.81-6.78(d, J = 8.19 Hz, 1H). |
| 13 | 3-acetyl-8-bromo-5-chloro-2-(phenylsulfinyl)quinolin-4(1H)-one | 424.69 | 424 | $^1$H NMR (300 MHz, CDCl$_3$)δ7.84-7.75(m, 2H), 7.68-7.64(m, 2H), 7.52-7.50(d, J = 8.43 Hz, 1H), 7.48-7.45(m, 1H), 7.38-7.35(d, J = 8.43 Hz, 1H), 2.78(s, 3H). |
| 14 | 3-acetyl-8-bromo-5-chloro-2-((2-methoxyphenyl)thio)quinolin-4(1H)-one | 438.72 | 438 | $^1$H NMR (300 MHz, CDCl$_3$)δ8.55(s, 1H), 7.709(m, 1H), 7.633 (m, 1H), 7.511(d, 1H, J = 8.43 Hz), 7.158(m, 3H), 3.861(s, 3H), 2.781(s, 3H). |
| 15 | 3-acetyl-8-bromo-5-chloro-2-((2-methoxyphenyl)sulfinyl)quinolin-4(1H)-one | 454.72 | 454 | $^1$H NMR (300 MHz, CDCl$_3$)δ7.84(d, J = 8.4 Hz, 1H), 7.383 (d, J = 8.4 Hz, 1H), 7.53 (m, 1H), 7.415 (m, 1H), 6.949 (s, 1H), 6.956 (s, 1H), 3.86 (s, 3H), 2.634 (s, 3H). |
| 16 | 3-acetyl-8-bromo-2-((4-bromophenyl)thio)-5-chloroquinolin-4(1H)-one | 487.59 | 486 | $^1$H NMR (300 MHz, CDCl$_3$)δ8.30(s, 1H), 7.779(d, J = 8.4 Hz, 2H), 7.614(d, J = 8.46 Hz, 2H), 7.541(d, J = 8.4 Hz, 1H), 7.183(d, J = 8.46 Hz, 1H), 2.77(s, 3H). |
| 17 | 3-acetyl-8-bromo-2-((4-bromophenyl)sulfinyl)-5-chloroquinolin-4(1H)-one | 503.59 | 502 | $^1$H NMR (300 MHz, CDCl$_3$)δ11.37(s, 1H), 7.84-7.81(d, J = 8.46 Hz, 1H), 7.73-7.70(d, J = 8.73 Hz, 2H), 7.60-7.57(d, J = 8.67 Hz, 2H), 7.39-7.38(d, J = 8.43 Hz, 1H), 2.70(s, 3H). |
| 18 | 1,1'-(8-bromo-5-chloro-2-(methylthio)-4-oxoquinoline-1,3(4H)-diyl)bis(ethan-1-one) | 388.66 | 388 | $^1$H NMR (300 MHz, MeOD) δ 7.84 (d, J = 8.25 Hz, 1H), 7.19(d, J = 8.25 Hz, 1H), 2.72(s, dH), 2.57(s, 3H), 2.18(s, 3H). |
| 19 | 1,1'-(8-bromo-5-chloro-2-(methylsulfinyl)-4-oxoquinoline-1,3(4H)-diyl)bis(ethan-1-one) | 404.66 | 404 | $^1$H NMR (300 MHz, CDCl$_3$)δ8.07(m, 1H), 7.60(m, 1H), 3.03 (s, 3H), 3.02(s, 3H), 2.78(s, 3H). |
| 20 | 3-acetyl-2-(benzylsulfinyl)-8-bromo-1-(4-bromobenzoyl)-5-chloroquinolin-4(1H)-one | 621.72 | 620 | $^1$H NMR (300 MHz, (CD$_3$)$_2$CO)δ7.96-7.93(d, J = 8.22 Hz, 1H), 7.73-7.60(m, 7H), 7.45-7.42(d, J = 8.25 Hz, 2H), 7.16-7.13(d, J = 8.19 Hz, 1H), 2.86(s, 3H). |
| 21 | 3-acetyl-8-bromo-1-(4-bromobenzoyl)-5-chloro-2-(methylsulfonyl)quinolin-4(1H)-one | 561.63 | 560 | $^1$H NMR (300 MHz, CDCl$_3$)δ8.10(d, J = 8.22 Hz, 1H), 8.03-7.67 (dd, J = 8.61, 88.8 Hz, 4H), 7.60(J = 8.22 Hz, 1H), 3.53(s, 3H), 2.67(s, 3H). |
| 22 | 3-acetyl-8-bromo-5-chloro-1-(3-chloro-4-fluorobenzyl)-2-(methylsulfinyl)quinolin-4(1H)-one | 505.18 | 504 | $^1$H NMR (300 MHz, CDCl$_3$)δ7.42-7.37(m, 2H), 7.24-7.09(m, 3H), 4.49(s, 2H), 3.44(s, 3H), 2.14(s, 3H). |

TABLE 4-continued

| Compound No. | Formula Name | MW (molecular weight) | LC/MS data | ¹H NMR |
|---|---|---|---|---|
| 23 | 3-acetyl-2-(benzylthio)-8-bromo-1-(4-bromobenzoyl)-5-chloroquinolin-4(1H)-one | 605.73 | 604 | ¹H NMR (300 MHz, CDCl₃)δ8.06-8.03(d, J = 8.28 Hz, 1H), 7.93-7.91(d, J = 8.64 Hz, 2H), 7.71-7.68(d, 8.64 Hz, 2H), 7.54-7.51(d, J = 7.02 Hz, 2H), 7.49-7.46(d, J = 8.25 Hz, 1H), 7.30-7.27(d, J = 7.33 Hz, 2H), 6.97(s, 1H), 4.71(s, 2H). |
| 24 | 3-acetyl-8-bromo-5-chloro-2-(isopropylthio)quinolin-4(1H)-one | 374.68 | 374 | ¹H NMR (300 MHz, CDCl₃)δ16.32(s, 1H), 7.77-7.86(d, J = 8.13 Hz, 1H), 7.26-7.23(d, J = 8.61 HZ, 1H), 4.54-4.45(m, 1H), 2.94(s, 3H), 1.54-1.51(m, 6H). |
| 25 | 3-acetyl-8-bromo-5-chloro-2-(isopropylsulfinyl)quinolin-4(1H)-one | 390.68 | 390 | ¹H NMR (300 MHz, CDCl₃)δ10.99(s, 1H), 7.80-7.77(d, J = 8.37 Hz, 1H), 7.36-7.34(d, J = 8.4 Hz, 1H), 3.61-3.51(m, 1H), 2.77(s, 3H), 1.63-1.61(d, J = 7.12 Hz, 3H), 1.01-0.99(d, J = 6.78 Hz, 3H). |
| 26 | 3-acetyl-8-bromo-5-chloro-2-((1-phenylethyl)sulfinyl)quinolin-4(1H)-one | 452.75 | 452 | ¹H NMR (300 MHz, CDCl₃)δ11.06(br, 1H), 7.82(d, J = 8.4 Hz, 1H), 7.60-7.65 (m, 2H), 7.41-7.50 (m, 3H), 7.38 (d, J = 8.5 Hz, 1H), 4.72 (q, J = 7.3 Hz, 1H), 2.84 (s, 3H), 1.42 (d, J = 7.1 Hz, 3H). |
| 27 | 3-(((3-acetyl-8-bromo-5-chloro-4-oxo-1,4-dihydroquinolin-2-yl)thio)methyl)benzonitrile | 447.73 | 447 | ¹H NMR (300 MHz, CDCl₃)δ7.92 (d, J = 8.3 Hz, 1H), 7.83 (s, 1H), 7.76 (d, J = 7.9 Hz, 1H), 7.55 (d, J = 7.7 Hz, 1H), 7.42 (t, J = 7.8 Hz, 1H), 7.32 (d, J = 8.3 Hz, 1H), 4.82 (s, 2H), 2.94 (s, 3H). |
| 28 | 3-(((3-acetyl-8-bromo-5-chloro-4-oxo-1,4-dihydroquinolin-2-yl)sulfinyl)methyl)benzonitrile | 463.73 | 463 | ¹H NMR (300 MHz, CDCl₃)δ10.27(br, 1H), 7.72(d, J = 8.5 Hz, 1H), 7.53-7.57 (m, 1H), 7.27-7.40 (m, 2H), 4.59 4.22 (m, 2H), 2.85 (s, 3H). |
| 29 | 3-acetyl-8-bromo-5-chloro-2-((2,4-difluorobenzyl)sulfinyl)quinolin-4(1H)-one | 474.70 | 474 | ¹H NMR (300 MHz, CDCl₃)δ10.34(br, 1H), 7.74(d, J = 8.4 Hz, 1H), 7.35 (d, J = 8.4 Hz, 1H), 7.20-7.28 (m, 1H), 6.81-6.87 (m, 1H), 6.60-6.75 (m, 1H), 4.53 (dd, J = 48.9, 13.2 Hz, 2H), 2.85 (s, 3H). |
| 30 | 3-acetyl-8-bromo-5-chloro-2-((3-chloro-4-fluorobenzyl)thio)quinolin-4(1H)-one | 475.15 | 474 | ¹H NMR (300 MHz, CDCl₃)δ7.92(d, J = 8.3 Hz, 1H), 7.83 (s, 1H), 7.76 (d, J = 7.9 Hz, 1H), 7.55 (d, J = 7.7 Hz, 1H), 7.42 (t, J = 7.8 Hz, 1H), 7.32 (d, J = 8.3 Hz, 1H), 4.82 (s, 2H), 2.94 (s, 3H). |
| 31 | 3-acetyl-8-bromo-5-chloro-2-((3-chloro-4-fluorobenzyl)sulfinyl)quinolin-4(1H)-one | 491.15 | 490 | ¹H NMR (300 MHz, CDCl₃)δ10.27(br, 1H), 7.73(d, J = 8.4 Hz, 1H), 7.33 (d, J = 8.4 Hz, 1H), 7.22-7.24 (m, 1H), 6.95-6.98 (m, 2H), 4.33 (q, J = 12.8 Hz, 2H), 2.84 (s, 3H). |
| 32 | 3-acetyl-8-bromo-5-chloro-2-((4-nitrobenzyl)thio)quinolin-4(1H)-one | 467.72 | 467 | ¹H NMR (300 MHz, CDCl₃)δ8.16(d, J = 8.6 Hz, 2H), 7.92 (d, J = 8.3 Hz, 1H), 7.69 (d, J = 8.6 Hz, 2H), 7.32 (d, J = 8.2 Hz, 1H), 4.90 (s, 2H), 2.94 (s, 3H). |
| 33 | 3-acetyl-8-bromo-5-chloro-2-((4-nitrobenzyl)sulfinyl)quinolin-4(1H)-one | 483.72 | 483 | ¹H NMR (300 MHz, CDCl₃)δ10.23(br, 1H), 8.08(d, J = 8.7 Hz, 2H), 7.70 (d, J = 8.4 Hz, 1H), 7.34 (dd, J = 8.5, 3.9 Hz, 3H), 4.49 (dd, J = 27.8, 12.6 Hz, 2H), 2.85 (s, 3H). |
| 34 | 3-acetyl-2-(benzylsulfonyl)-8-bromo-5-chloroquinolin-4(1H)-one | 454.72 | 454 | ¹H NMR (300 MHz, CDCl₃)δ10.25(s, 1H), 7.66(d, J = 8.46 Hz, 1H), 7.28(d, J = 8.43 Hz, 1H), 7.20-7.08(m, 5H), 4.41(d, J = 3, 2H), 2.84(s, 3H). |
| 35 | 3-acetyl-8-bromo-5-chloro-1-(methylsulfonyl)-2-(methylthio)quinolin-4(1H)-one | 424.71 | 424 | ¹H NMR (300 MHz, CDCl₃)δ7.96(d, J = 8.25 Hz, 1H), 7.42(d, J = 8.28 Hz, 1H), 3.30(s, 3H), 2.76(s, 3H), 2.73(s, 3H). |
| 36 | 3-acetyl-8-bromo-5-chloro-2-(methylsulfinyl)-1-((trifluoromethyl)sulfonyl)quinolin-4(1H)-one | 494.68 | 494 | ¹H NMR (300 MHz, CDCl₃)δ8.08-8.05(d, J = 8.22 Hz, 1H), 7.69-7.65(d, J = 8.25 Hz, 1H), 3.11(s, 3H), 2.78(s, 3H). |

TABLE 4-continued

| Compound No. | Formula Name | MW (molecular weight) | LC/MS data | $^1$H NMR |
|---|---|---|---|---|
| 37 | 3-acetyl-8-bromo-5-chloro-1-((4-chlorophenyl)sulfonyl)-2-(methylthio)quinolin-4(1H)-one | 521.22 | 520 | $^1$H NMR (300 MHz, CDCl$_3$)δ7.93-7.91(d, J = 8.22 Hz, 1H), 7.74-7.71(d, J = 8.7 Hz, 2H), 7.50-7.47(d, J = 8.61 Hz, 2H), 7.32-7.30(d, J = 8.25 Hz, 1H), 2.71(s, 3H), 2.62(s, 3H). |
| 38 | 3-acetyl-8-bromo-5-chloro-2-(methylthio)-1-((4-nitrophenyl)sulfonyl)quinolin-4(1H)-one | 531.78 | 531 | $^1$H NMR (300 MHz, CDCl$_3$)δ8.39-8.36(d, J = 8.85 Hz, 2H), 8.03-8.00(d, J = 8.85 Hz, 2H), 7.96-9.93 (d, J = 8.22 Hz, 1H), 7.35-7.32(d, J = 8.22 Hz, 1H), 2.74(s, 3H), 2.62(s, 3H). |
| 39 | 3-acetyl-8-bromo-5-chloro-1-(ethylsulfonyl)-2-(methylsulfinyl)quinolin-4(1H)-one | 454.73 | 454 | $^1$H NMR (300 MHz, CDCl$_3$)δ7.96-7.93(d, J = 8.23 Hz, 1H), 7.42-7.39(d, J = 8.16 Hz, 1H), 3.54-3.46(q, J = 7.41, 7.5 Hz, 2H), 2.76(s, 3H), 2.73(s, 3H), 1.58-1.53(t, J = 7.38, 7.44, 3H). |
| 40 | 3-acetyl-8-bromo-1-((4-(tert-butyl)phenyl)sulfonyl)-5-chloro-2-(methylthio)quinolin-4(1H)-one | 542.89 | 542 | $^1$H NMR (300 MHz, CDCl$_3$)δ7.88-7.85(d, J = 8.16 Hz, 1H), 7.69-7.66(d, J = 8.67 Hz, 2H), 7.47-7.44(d, J = 8.7 Hz, 2H), 7.25-7.23(d, J = 8.13 Hz, 1H), 2.71(s, 3H), 2.63(s, 3H), 1.33 (s, 9H). |
| 41 | 3-acetyl-8-bromo-1-((4-(tert-butyl)phenyl)sulfonyl)-5-chloro-2-(methylsulfonyl)quinolin-4(1H)-one | 574.89 | 574 | $^1$H NMR (300 MHz, CDCl$_3$)δ8.10-8.07(d, J = 8.22 Hz, 1H), 7.80-7.78(d, J = 8.64 Hz, 2H), 7.62-7.59(d, J = 8.25 Hz, 1H), 7.58-7.55(d, J = 8.64 Hz, 2H), 3.48(s, 3H), 2.71(s, 3H), 1.37(s, 9H). |
| 42 | 3-acetyl-8-bromo-1-((4-(tert-butyl)phenyl)sulfonyl)-5-chloro-2-(methylsulfinyl)quinolin-4(1H)-one | 558.89 | 558 | $^1$H NMR (300 MHz, CDCl$_3$)δ8.05-8.03(d, J = 8.16 Hz, 1H), 7.71-7.68(d, J = 8.64 Hz, 2H), 7.52-7.49(d, J = 8.28 Hz, 3H), 3.13(s, 3H), 2.69(s, 3H), 1.35(s, 9H). |
| 43 | 3-acetyl-8-bromo-5-chloro-2-((2,5-dichlorobenzyl)thio)quinolin-4(1H)-one | 491.61 | 490 | $^1$H NMR (300 MHz, DMSO) δ 7.93-7.90(d, J = 8.25 Hz, 1H), 7.84 (s, 1H), 7.52-7.49(d, J = 8.52 Hz, 1H), 7.37-7.33(m, 1H), 7.25-7.22(d, J = 8.34 Hz, 1H), 4.65(s, 2H). |
| 44 | 3-acetyl-8-bromo-5-chloro-2-((2,5-dichlorobenzyl)sulfinyl)quinolin-4(1H)-one | 507.60 | 506 | $^1$H NMR (300 MHz, CDCl$_3$)δ10.35(s, 1H), 7.73-7.72(d, J = 10.86 Hz, 1H), 7.32(s, 2H), 7.17(s, 2H), 4.81-4.49(dd, J = 13.33, 69.53 Hz, 2H), 2.81(s, 3H). |
| 45 | 3-acetyl-8-bromo-5-chloro-2-((3,5-difluorobenzyl)thio)quinolin-4(1H)-one | 458.70 | 458 | $^1$H NMR (300 MHz, CDCl$_3$)δ7.93-7.91(d, J = 8.28 Hz, 1H), 7.33-7.30(d, J = 8.28 Hz, 1H), 7.06-7.04(m, 3H), 4.78(s, 2H), 2.94(s, 3H). |
| 46 | 3-acetyl-8-bromo-5-chloro-2-((3,5-difluorobenzyl)sulfinyl)quinolin-4(1H)-one | 474.70 | 474 | $^1$H NMR (300 MHz, CDCl$_3$)δ10.43(s, 1H), 7.75-7.72(d, J = 8.4 Hz, 1H), 7.35-7.32(d. J = 8.46 Hz, 1H), 6.80-6.68(m, 3H), 4.44-4.23(q, J = 12.63, 36.84 Hz, 2H), 2.84(s, 3H). |
| 47 | 3-acetyl-8-bromo-5-chloro-2-((3-iodobenzyl)thio)quinolin-4(1H)-one | 548.62 | 548 | $^1$H NMR (300 MHz, DMSO) δ 7.97-7.94(d, J = 5.55 Hz, 1H), 7.89(s, 1H), 7.61-7.58(d, J = 8.16 Hz, 1H), 7.49-7.46(d, J = 7.11 Hz, 1H), 7.31-7.29(m, 1H), 7.13-7.80(t, J = 7.76 Hz, 1H), 4.55(s, 2H). |
| 48 | 3-acetyl-8-bromo-5-chloro-2-((3-iodobenzyl)sulfinyl)quinolin-4(1H)-one | 564.62 | 564 | $^1$H NMR (300 MHz, CDCl$_3$)δ10.19(s, 1H), 7.74-7.71(d, J = 8.46 Hz, 1H), 7.56-7.54(d, J = 8.07 Hz, 1H), 7.39(s, 1H), 7.35-7.32(d, J = 8.46 Hz, 1H), 7.09-7.07(d, J = 8.01 Hz, 1H), 6.97-6.92(t, J = 7.74 Hz, 1H), 4.40-4.30(q, J = 12.71, 6.06 Hz, 2H), 2.87(s, 3H). |
| 49 | 3-acetyl-8-bromo-5-chloro-2-((3-fluorobenzyl)thio)quinolin-4(1H)-one | 440.71 | 440 | $^1$H NMR (300 MHz, CDCl$_3$)δ7.93-7.91(d, J = 8.25 Hz, 1H), 7.32-7.30(d, J = 8.19 Hz, 2H), 7.28-7.27(m, 2H), 6.97(s, 1H), 4.79(s, 2H), 2.94(s, 3H). |
| 50 | 3-acetyl-8-bromo-5-chloro-2-((3-fluorobenzyl)sulfinyl)quinolin-4(1H)-one | 456.71 | 456 | $^1$H NMR (300 MHz, CDCl$_3$)δ10.30(s, 1H), 7.70-7.67(d, J = 8.56 Hz, 1H), 7.30-7.27(d, J = 8.43 Hz, 1H), 7.15-7.07(m, 1H), 6.98-6.88(m, 2H), 6.83-6.81(d, J = 7.68 Hz, 1H), 4.42-4.32(q, J = 12.66, 3.33 Hz, 2H), 2.82(s, 3H). |

TABLE 4-continued

| Compound No. | Formula Name | MW (molecular weight) | LC/MS data | $^1$H NMR |
|---|---|---|---|---|
| 51 | 3-acetyl-8-bromo-5-chloro-2-(((5-methylisoxazol-3-yl)methyl)sulfinyl)quinolin-4(1H)-one | 443.70 | 442 | $^1$H NMR (300 MHz, CDCl$_3$)δ10.50(br, 1H), 7.77(d, J = 8.4 Hz, 1H), 7.36 (d, J = 8.4 Hz, 1H), 6.17 (s, 1H), 4.33-4.67 (m, 2H), 2.83 (s, 3H), 2.39 (s, 3H). |
| 52 | 1-(2-(benzylthio)-8-bromo-5-chloro-4-hydroxyquinolin-3-yl)ethan-1-one | 422.72 | 422 | $^1$H NMR (300 MHz, CDCl$_3$)δ7.82(d, J = 8.2 Hz, 1H), 7.53 (d, J = 6.8 Hz, 2H), 7.32-7.48 (m, 3H), 7.26 (d, J = 8.4 Hz, 1H), 6.77 (s, 2H), 5.24 (s, 3H). |
| 53 | 1-(2-(benzylsulfinyl)-8-bromo-5-chloro-4-hydroxyquinolin-3-yl)ethan-1-one | 438.72 | 438 | $^1$H NMR (300 MHz, CDCl$_3$)δ7.99(d, J = 8.2 Hz, 1H), 7.60 (s, 1H), 7.54-7.57 (m, 2H), 7.51 (d, J = 8.2 Hz, 1H), 7.37-7.48 (m, 3H), 5.39 (s, 2H), 3.48(s, 3H). |
| 54 | 1-(2-(benzylsulfonyl)-8-bromo-5-chloro-4-hydroxyquinolin-3-yl)ethan-1-one | 454.72 | 454 | $^1$H NMR (300 MHz, CDCl$_3$)δ7.94(d, J = 8.2 Hz, 1H), 7.73 (s, 1H), 7.54-7.58 (m, 2H), 7.45 (d, J = 8.1 Hz, 2H), 7.38-7.41 (m, 2H), 5.42 (s, 2H), 3.01 (s, 3H). |
| 55 | 3-acetyl-8-bromo-5-chloro-2-((3-methoxybenzyl)sulfinyl)quinolin-4(1H)-one | 468.75 | 468 | $^1$H NMR (300 MHz, CDCl$_3$)δ10.32(s, 1H), 7.71-7.69(d, J = 8.4 Hz, 1H), 7.33-7.30(d, J = 8.43, 1H), 7.09-7.04(t, J = 7.8 Hz, 1H), 6.76-6.70(m, 2H), 6.65-6.63(d, J = 7.47 Hz, 1H), 4.44-4.34(q, J = 12.7, 4.86 Hz, 2H), 3.70(s, 3H), 2.86(s, 3H). |
| 56 | 3-acetyl-8-bromo-5-chloro-2-((4-((trifluoromethyl)thio)benzyl)sulfinyl)quinolin-4(1H)-one | 538.78 | 538 | $^1$H NMR (300 MHz, CDCl$_3$)δ10.27(s, 1H), 7.69-7.66(d, J = 8.40 Hz, 1H), 7.49-7.46(d, J = 8.01 Hz, 2H), 7.31-7.28(d, J = 8.40 Hz, 1H), 7.18-7.15(d, J = 8.16 Hz, 2H), 4.52-4.37(q, J = 12.7, 17.1 Hz, 2H), 2.84(s, 3H). |
| 57 | 3-acetyl-5,8-dichloro-2-((4-nitrobenzyl)sulfinyl)quinolin-4(1H)-one | 439.26 | 439 | $^1$H NMR (300 MHz, MeOD) δ9.95(s, 1H), 8.22-8.20(d, J = 8.6 Hz, 2H), 7.73-7.70(d, J = 8.31 Hz, 2H), 7.63-7.60(d, J = 8.22 Hz, 1H), 7.29-7.26(d, J = 8.13 Hz, 1H), 4.59-4.10(q, J = 12.3, 122 Hz, 2H), 2.72(s, 3H). |
| 58 | 2-(((3-acetyl-8-bromo-5-chloro-4-oxo-1,4-dihydroquinolin-2-yl)sulfinyl)methyl)benzonitrile | 463.73 | 463 | $^1$H NMR (300 MHz, CDCl$_3$)δ10.30(br, 1H), 7.69(d, J = 8.4 Hz, 1H), 7.47-7.61 (m, 2H), 7.34-7.45 (m, 2H), 7.31 (d, J = 8.4 Hz, 1H), 4.71 (q, J = 13.1 Hz, 2H), 2.85 (s, 3H). |
| 59 | 3-acetyl-8-bromo-5-chloro-2-((3,5-dimethoxybenzyl)sulfinyl)quinolin-4(1H)-one | 498.77 | 498 | $^1$H NMR (300 MHz, CDCl$_3$)δ10.36(s, 1H), 7.69(d, J = 8.4 Hz, 1H), 7.30 (d, J = 8.4 Hz, 1H), 6.23 (s, 3H), 4.25-4.39 (m, 2H), 3.62 (s, 6H), 2.83 (s, 3H). |
| 60 | 3-acetyl-8-bromo-2-((4-(tert-butyl)benzyl)sulfinyl)-5-chloroquinolin-4(1H)-one | 494.83 | 494 | $^1$H NMR (300 MHz, CDCl$_3$)δ10.15(br, 1H), 7.62(d, J = 8.4 Hz, 1H), 7.25 (d, J = 8.4 Hz, 1H), 7.13 (d, J = 8.3 Hz, 2H), 6.96 (d, J = 8.3 Hz, 2H), 4.40 (dd, J = 53.3, 12.7 Hz, 2H),, 2.83 (s, 3H), 1.11 (s, 9H). |
| 61 | 3-acetyl-8-bromo-5-chloro-2-((methoxymethyl)thio)quinolin-4(1H)-one | 376.65 | 376 | $^1$H NMR (300 MHz, CDCl$_3$)δ10.62(br, 1H), 7.69(d, J = 8.4 Hz, 1H), 7.24 (d, J = 8.4 Hz, 1H), 5.07 (s, 2H), 3.66 (s, 3H), 2.69 (s, 3H). |
| 62 | 3-acetyl-8-bromo-5-chloro-2-mercaptoquinolin-4(1H)-one | 332.60 | 332 | $^1$H NMR (300 MHz, CDCl$_3$)δ10.11(br, 1H), 7.74(d, J = 8.5 Hz, 1H), 7.21 (d, J = 8.5 Hz, 1H), 3.15 (s, 3H). |
| 63 | 3-acetyl-2-((4-benzoylbenzyl)sulfinyl)-8-bromo-5-chloroquinolin-4(1H)-one | 542.83 | 542 | $^1$H NMR (300 MHz, CDCl$_3$)δ10.29(br, 1H), 7.67(d, J = 8.4 Hz, 1H), 7.61 (d, J = 8.2 Hz, 2H), 7.37-7.59 (m, 5H), 7.31 (d, J = 8.4 Hz, 1H), 7.23 (d, J = 8.2 Hz, 1H), 4.51 (q, J = 12.6 Hz, 2H), 2.85 (s, 3H). |
| 64 | 3-acetyl-8-bromo-5-chloro-2-((4-((trifluoromethyl)sulfinyl)benzyl)sulfinyl)quinolin-4(1H)-one | 554.78 | 554 | $^1$H NMR (300 MHz, CDCl$_3$)δ10.30 (br s, 1H), 7.70-7.62(m, 3H), 7.41-7.26(m, 3H), 4.55-4.45(q, J = 16.3 Hz, 2H), 2.84 (s, 3H). |

TABLE 4-continued

| Compound No. | Formula Name | MW (molecular weight) | LC/MS data | ¹H NMR |
|---|---|---|---|---|
| 65 | 2-((3-acetyl-8-bromo-5-chloro-4-oxo-1,4-dihydroquinolin-2-yl)sulfinyl)acetonitrile | 387.63 | 387 | ¹H NMR (300 MHz, CDCl$_3$)δ10.97(br, 1H), 7.87(d, J = 8.4 Hz, 1H), 7.43 (d, J = 8.5 Hz, 1H), 4.27 (q, J = 16.3 Hz, 2H), 2.84 (s, 3H). |
| 66 | 2-((3-acetyl-8-bromo-5-chloro-4-oxo-1,4-dihydroquinolin-2-yl)thio)acetonitrile | 371.63 | 371 | ¹H NMR (300 MHz, CDCl$_3$)δ7.96(d, J = 8.3 Hz, 1H), 7.36 (d, J = 8.3 Hz, 1H), 4.30 (s, 2H), 2.94 (s, 3H). |
| 67 | (Z)-3-((3-acetyl-8-bromo-5-chloro-4-oxo-1,4-dihydroquinolin-2-yl)thio)acrylic acid | 402.64 | 402 | ¹H NMR (300 MHz, MeOD) δ9.03 (br, 0.5H), 8.84 (br, 1H), 7.97 (d, J = 8.2 Hz, 1H), 7.91 (d, J = 8.3 Hz, 0.5H), 7.37 (d, J = 8.4 Hz, 1H), 7.31 (d, J = 8.3 Hz, 0.5H), 6.34 (d, J = 10.8 Hz, 0.5H), 6.22 (d, J = 10.3 Hz, 1H), 2.78 (s, 3H), 2.72 (s, 1.5H). |
| 68 | 3-acetyl-8-bromo-5-chloro-2-((4-(pentafluoro-l6-sulfanyl)benzyl)sulfinyl)quinolin-4(1H)-one | 564.76 | 564 | ¹H NMR (300 MHz, CDCl$_3$)δ10.14 (s, 1H), 7.71 (d, J = 8.4 Hz, 1H), 7.57 (d, J = 8.7 Hz, 2H), 7.33 (d, J = 8.5 Hz, 1H), 7.20 (d, J = 8.3 Hz, 2H), 4.47 (dd, J = 30.2, 12.6 Hz, 2H), 2.87 (s, 3H). |
| 69 | 3-acetyl-8-bromo-5-chloro-2-((-fluoro-4-(pentafluoro-l6-sulfanyl)benzyl)sulfinyl)quinolin-4(1H)-one | 582.75 | 582 | ¹H NMR (300 MHz, CDCl$_3$)δ10.19(s, 1H), 7.71-7.68(d, J = 8.43 Hz, 1H), 7.33-7.30(d, J = 8.31 Hz, 1H), 4.73-4.40(q, J = 13.0, 72.1 Hz, 2H), 2.83(s, 3H). |
| 70 | 3-acetyl-8-bromo-5-chloro-2-((4-(trifluoromethyl)benzyl)sulfinyl)quinolin-4(1H)-one | 506.72 | 506 | ¹H NMR (300 MHz, CDCl$_3$)δ10.16 (s, 1H), 7.71 (d, J = 8.4 Hz, 1H), 7.46 (d, J = 8.1 Hz, 2H), 7.33 (d, J = 8.4 Hz, 1H), 7.25 (d, J = 8.0 Hz, 2H), 4.60-4.34 (m, 2H), 2.87 (s, 3H). |
| 71 | 3-acetyl-8-bromo-5-chloro-2-((4-(trifluoromethoxy)benzyl)sulfinyl)quinolin-4(1H)-one | 522.72 | 522 | ¹H NMR (300 MHz, CDCl$_3$)δ10.24(br, 1H), 7.69(d, J = 8.5 Hz, 1H), 7.30 (d, J = 8.4 Hz, 1H), 7.14 (d, J = 8.7 Hz, 2H), 7.04 (d, J = 8.1 Hz, 2H), 4.42 (q, J = 12.8 Hz, 2H), 2.84 (s, 3H). |
| 72 | 3-acetyl-8-bromo-5-chloro-2-(((5-(trifluoromethyl)furan-2-yl)methyl)sulfinyl)quinolin-4(1H)-one | 496.68 | 496 | ¹H NMR (300 MHz, CDCl$_3$)δ10.34 (s, 1H), 7.75 (d, J = 8.5 Hz, 1H), 7.36 (d, J = 8.4 Hz, 1H), 6.71 (s, 1H), 6.59 (d, J = 3.1 Hz, 1H), 4.58 (dd, J = 71.0, 14.1 Hz, 2H), 2.87 (s, 3H). |
| 73 | 4-(((3-acetyl-8-bromo-5-chloro-4-oxo-1,4-dihydroquinolin-2-yl)sulfinyl)methyl)benzonitrile | 463.73 | 463 | ¹H NMR (300 MHz, CDCl$_3$)δ10.21(s, 1H), 775-7.72(d, J = 8.4 Hz, 1H), 7.52-7.50(d, J = 8.04 Hz, 2H), 7.36-7.33(d, J = 8.43 Hz, 1H), 7.27-7.25(d, J = 8.1 Hz, 2H), 4.50-4.39(q, J = 12.4, 6.33 Hz, 2H), 2.84(s, 3H). |
| 74 | 3-acetyl-8-bromo-5-chloro-2-((2-chloro-6-fluorobenzyl)sulfinyl)quinolin-4(1H)-one | 491.15 | 491 | ¹H NMR (300 MHz, CDCl$_3$)δ10.6(s, 1H), 7.75-7.72(d, J = 8.4 Hz, 1H), 7.35-7.33(d, J = 8.4 Hz, 1H), 7.31-7.28(m, 1H), 7.24-7.18(t, J = 8.8 Hz, 1H), 7.01-6.96(t, J = 8.0 Hz, 1H), 5.08-5.05(q, J = 1.9, 11, 120 Hz, 2H), 2.82(s, 3H). |
| 75 | 3-acetyl-8-bromo-5-chloro-2-((2-methoxy-4-(pentafluoro-l6-sulfanyl)benzyl)sulfinyl)quinolin-4(1H)-one | 594.79 | 594 | ¹H NMR (300 MHz, CDCl$_3$)δ10.26(s, 1H), 7.69-7.67(d, J = 8.40 Hz, 1H), 7.31-7.28(d, J = 8.43 Hz, 1H), 4.80-4.40(q, J = 13.0, 95.7 Hz, 2H), 2.82(s, 3H). |
| 76 | 3-acetyl-8-bromo-5-chloro-2-((3-fluoro-5-(pentafluoro-l6-sulfanyl)benzyl)sulfinyl)quinolin-4(1H)-one | 582.75 | 582 | ¹H NMR (300 MHz, CDCl$_3$)δ10.13 (s, 1H), 7.70 (d, J = 8.5 Hz, 1H), 7.38 (s, 1H), 7.33 (d, J = 8.6 Hz, 1H), 7.21 (d, J = 8.1 Hz, 1H), 7.09 (s, 1H), 4.44 (s, 2H), 2.84 (s, 3H). |
| 77 | 3-acetyl-8-bromo-5-chloro-2-((3-(pentafluoro-l6-sulfanyl)benzyl)sulfinyl)quinolin-4(1H)-one | 564.76 | 564 | ¹H NMR (300 MHz, CDCl$_3$)δ10.06 (s, 1H), 7.59-7.68 (m, 2H), 7.29-7.38 (m, 4H), 4.47 (q, J = 12.8 Hz, 2H), 2.85 (s, 3H). |
| 78 | 3-acetyl-8-bromo-5-chloro-2-(((perfluorophenyl)methyl)sulfinyl)quinolin-4(1H)-one | 528.67 | 528 | ¹H NMR (300 MHz, CDCl$_3$)δ10.48(s, 1H), 7.79-7.77(d, J = 8.43 Hz, 1H), 7.38-7.36(d, J = 8.31 Hz, 1H), 4.49-4.40(q, J = 13.0, 128 Hz, 2H), 2.83(s, 3H). |

TABLE 4-continued

| Compound No. | Formula Name | MW (molecular weight) | LC/MS data | $^1$H NMR |
|---|---|---|---|---|
| 79 | 3-acetyl-5,8-dichloro-2-((4-((trifluoromethyl)thio)benzyl)sulfinyl)quinolin-4(1H)-one | 494.32 | 494 | $^1$H NMR (300 MHz, CDCl$_3$)δ10.24(br s, 1H), 7.56-7.49 (m, 4H), 7.39-7.37(d, J = 8.52 Hz, 2H), 7.21-7.18(d, J = 7.68 Hz, 2H), 4.52-4.40(q, J = 13.4 Hz, 2H), 2.87(s, 3H). |
| 80 | 3-acetyl-5,8-difluoro-2-((4-(pentafluoro-l6-sulfanyl)benzyl)sulfinyl)quinolin-4(1H)-one | 487.40 | 487 | $^1$H NMR (300 MHz, CDCl$_3$)δ9.78(br s, 1H), 7.59-7.58 (d, J = 8.49 Hz, 1H), 7.37-7.22(m, 3H), 7.06-6.98(m, 1H), 4.41(s, 2H), 2.84(s, 3H). |
| 81 | 3-acetyl-5,8-difluoro-2-(((5-(trifluoromethyl)furan-2-yl)methyl)sulfinyl)quinolin-4(1H)-one | 419.32 | 419 | $^1$H NMR (300 MHz, CDCl$_3$)δ9.93(br s, 1H), 7.41-7.33(m, 1H), 7.08-7.00 (m, 1H), 6.71-6.69(m, 1H), 6.56-6.55(m, 1H), 4.66(d, J = 14.1 Hz, 1H), 4.48-4.44(d, J = 14.07 Hz, 1H), 2.83(s, 3H). |
| 82 | 3-acetyl-5,8-difluoro-2-(((5-methylisoxazol-3-yl)methyl)sulfinyl)quinolin-4(1H)-one | 366.34 | 366 | $^1$H NMR (300 MHz, CDCl$_3$)δ 10.45(br s, 1H), 7.61-7.59(d, J = 8.49 Hz, 2H), 7.41-7.38 (d, J = 8.46 Hz, 1H), 6.16(s, 1H), 4.51-4.39(q, J = 13.5, 21.8 Hz, 2H), 2.81(s, 3H), 2.37(s, 3H). |
| 83 | 3-acetyl-5,8-dichloro-2-((4-iodobenzyl)sulfinyl)quinolin-4(1H)-one | 520.16 | 520 | $^1$H NMR (300 MHz, CDCl$_3$)δ10.11(br s, 1H), 7.60-7.57(d, J = 8.46 Hz, 1H), 7.51-7.49 (d, J = 8.22 Hz, 2H), 7.40-7.37(d, J = 8.43 Hz, 1H), 6.83-6.81(d, J = 8.22 Hz, 2H), 4.32(s, 2H), 2.83(s, 3H). |
| 84 | 3-acetyl-8-bromo-5-chloro-2-((pyridin-3-ylmethyl)sulfinyl)quinolin-4(1H)-one | 439.71 | 439 | $^1$H NMR (300 MHz, DMSO) δ8.41 (d, J = 4.6 Hz, 1H), 8.21 (s, 1H), 7.99 (d, J = 8.5 Hz, 1H), 7.52 (d, J = 7.9 Hz, 1H), 7.44 (d, J = 8.5 Hz, 1H), 7.25 (dd, J = 7.6, 4.6 Hz, 1H), 4.71 (d, J = 13.1 Hz, 1H), 4.37 (d, J = 13.0 Hz, 1H), 2.68 (s, 3H). |
| 85 | 5,8-difluoro-3-isobutyryl-2-((4-((trifluoromethyl)thio)benzyl)sulfinyl)quinolin-4(1H)-one | 489.48 | 489 | $^1$H NMR (300 MHz, CDCl$_3$ + MeOD)δ7.60-6.92(m, 6H), 4.45-4.41(m, 1H), 4.35-4.31(m, 1H), 4.09-4.00 (m, 1H), 1.19-1.17(d, J = 6 Hz, 3H), 1.11-1.08(d, J = 7.17 Hz, 3H). |
| 86 | 5,8-dichloro-3-isobutyryl-2-(((5-methylisoxazol-3-yl)methyl)sulfinyl)quinolin-4(1H)-one | 427.30 | 427 | $^1$H NMR (300 MHz, CDCl$_3$)δ10.43(br s, 1H), 7.59-7.56(d, J = 8.43 Hz, 1H), 7.38-7.35(d, J = 8.43 Hz, 1H), 6.13(s, 1H), 4.50-4.39(d, J = 8.54 Hz, 2H), 4.14-4.05(m, 1H), 2.34(s, 3H). 1.21-1.15(dd, J = 6.8, 11.6 Hz, 6H). |
| 87 | 3-benzoyl-5,8-difluoro-2-((4-(pentafluoro-l6-sulfanyl)benzyl)sulfinyl)quinolin-4(1H)-one | 549.48 | 549 | $^1$H NMR (300 MHz, CDCl$_3$)δ7.74-7.27(m, 10H), 7.00-6.92 (m, 1H), 4.80-4.76(d, J = 12.66 Hz, 1H), 4.53-4.49(d, J = 12.6 Hz, 1H). |
| 88 | 3-benzoyl-5,8-dichloro-2-(((5-methylisoxazol-3-yl)methyl)sulfinyl)quinolin-4(1H)-one | 461.31 | 461 | $^1$H NMR (300 MHz, CDCl$_3$)δ7.77-7.75(d, J = 6.75 Hz, 2H), 7.74-7.70 (d, J = 8.28 Hz, 1H), 7.59-7.31(m, 5H), 6.18(s, 1H), 4.68(s, 2H), 3.10(s, 3H). |
| 89 | methyl 5-(((3-acetyl-5,8-dichloro-4-oxo-1,4-dihydroquinolin-2-yl)sulfinyl)methyl)furan-2-carboxylate | 442.26 | 442 | $^1$H NMR (300 MHz, CDCl$_3$)δ10.24 (s, 1H), 7.56 (d, J = 8.5 Hz, 1H), 7.38 (d, J = 8.5 Hz, 1H), 7.05 (d, J = 3.4 Hz, 1H), 6.59 (d, J = 3.4 Hz, 1H), 4.65 (d, J = 13.9 Hz, 1H), 4.44 (d, J = 13.9 Hz, 1H), 3.60 (s, 3H), 2.85 (s, 3H). |
| 90 | 2-(((3-acetyl-5,8-dichloro-4-oxo-1,4-dihydroquinolin-2-yl)sulfinyl)methyl)isoindoline-1,3-dione | 463.29 | 463 | $^1$H NMR (300 MHz, CDCl$_3$)δ10.52 (s, 1H), 8.00 7.74 (m, 4H), 7.62 (d, J = 8.4 Hz, 1H), 7.43 (d, J = 8.5 Hz, 1H), 5.74 (d, J = 12.6 Hz, 1H), 4.86 (d, J = 12.6 Hz, 1H), 2.87 (s, 3H). |
| 91 | methyl 4-(((3-acetyl-5,8-dichloro-4-oxo-1,4-dihydroquinolin-2-yl)sulfinyl)methyl)benzoate | 452.30 | 452 | $^1$H NMR (300 MHz, CDCl$_3$)δ10.23 (s, 1H), 7.87 (d, J = 8.2 Hz, 2H), 7.52 (d, J = 8.4 Hz, 1H), 7.36 (d, J = 8.4 Hz, 1H), 7.23 (d, J = 8.2 Hz, 2H), 4.44 (q, J = 12.5 Hz, 2H), 3.89 (d, J = 5.4 Hz, 3H), 2.85 (s, 3H). |
| 92 | 3-acetyl-5-methoxy-2-((4-(pentafluoro-l6-sulfanyl)benzyl)thio)quinolin-4(1H)-one | 465.45 | 465 | $^1$H NMR (300 MHz, CDCl$_3$)δ8.18 (d, J = 9.0 Hz, 1H), 7.71 (d, J = 8.7 Hz, 2H), 7.60 (d, J = 8.4 Hz, 2H), 7.14 (d, J = 2.4 Hz, 1H), 7.08 (dd, J = 9.0, 2.5 Hz, 1H), 4.70 (s, 2H), 4.00 (s, 3H), 2.92 (s, 3H). |

TABLE 4-continued

| Compound No. | Formula Name | MW (molecular weight) | LC/MS data | $^1$H NMR |
|---|---|---|---|---|
| 93 | 3-acetyl-5-methoxy-2-((4-(pentafluoro-l6-sulfanyl)benzyl)sulfinyl)quinolin-4(1H)-one | 481.45 | 481 | $^1$H NMR (300 MHz, CDCl$_3$)δ9.63 (s, 1H), 8.28 (d, J = 9.0 Hz, 1H), 7.57 (d, J = 8.6 Hz, 2H), 7.23 (s, 1H), 7.04 (dd, J = 9.0, 2.2 Hz, 1H), 6.54 (d, J = 2.2 Hz, 1H), 4.39 (dd, J = 36.0, 12.5 Hz, 2H), 3.87 (d, J = 10.5 Hz, 3H), 2.87 (s, 3H). |
| 94 | 3-acetyl-5-methoxy-2-(((5-methylisoxazol-3-yl)methyl)sulfinyl)quinolin-4(1H)-one | 360.38 | 360 | $^1$H NMR (300 MHz, CDCl$_3$)δ10.43 (s, 1H), 8.34 (d, J = 9.0 Hz, 1H), 7.08 (d, J = 8.9 Hz, 1H), 6.93 (s, 1H), 6.08 (s, 1H), 4.45 (dd, J = 60.6, 13.3 Hz, 2H), 3.91 (s, 3H), 2.87 (s, 3H), 2.32 (s, 3H). |
| 95 | 8-bromo-5-chloro-3-isobutyryl-2-(((5-methylisoxazol-3-yl)methyl)sulfinyl)quinolin-4(1H)-one | 471.75 | 471 | $^1$H NMR (300 MHz, CDCl$_3$)δ10.49(br s, 1H), 7.75-7.72 (d, J = 8.43 Hz, 1H), 7.34-7.31(d, J = 8.37 Hz, 1H), 6.13(s, 1H), 4.47(s, 2H), 4.16-4.07(m, 1H), 2.35(s, 3H), 1.23-1.17(dd, J = 6.7, 12.0 Hz, 6H). |
| 96 | 8-bromo-5-chloro-3-(cyclopropanecarbonyl)-2-(((5-methylisoxazol-3-yl)methyl)sulfinyl)quinolin-4(1H)-one | 469.73 | 469 | $^1$H NMR (300 MHz, CDCl$_3$)δ10.44(br s, 1H), 7.75-7.72 (d, J = 8.43 Hz, 1H), 7.34-7.31(d, J = 8.4 Hz, 1H), 6.11(s, 1H), 4.48-4.37(q, J = 10.5 Hz, 2H), 3.70-3.62(m, 1H), 2.35(s, 3H), 1.28-1.05(m, 4H). |
| 97 | 5,8-dichloro-3-(cyclopropanecarbonyl)-2-(((5-methylisoxazol-3-yl)methyl)sulfinyl)quinolin-4(1H)-one | 425.28 | 425 | $^1$H NMR (300 MHz, CDCl$_3$)δ10.42(br s, 1H), 7.61-7.58 (d, J = 8.43 Hz, 1H), 7.41-7.38(d, J = 8.43 Hz, 1H), 6.12(s, 1H), 4.49-4.37(q, J = 11.7 Hz, 2H), 3.71-3.62(m, 1H), 2.36(s, 3H), 1.29-1.06(m, 4H). |
| 98 | 5-(((3-acetyl-8-bromo-5-chloro-4-oxo-1,4-dihydroquinolin-2-yl)sulfinyl)methyl)thiophene-2-carbonitrile | 469.75 | 469 | $^1$H NMR (300 MHz, CDCl$_3$)δ10.31(br s, 1H), 7.79-7.77 (d, J = 8.43 Hz, 1H), 7.42-7.36(m, 2H), 6.91-6.86(d, J = 3.84 Hz, 1H), 4.77-4.72(d, J = 13.74 , 1H), 4.63-4.59(d, J = 13.71 Hz, 1H), 2.86(s, 3H). |
| 99 | 2-(((6-(1H-pyrazol-1-yl)pyridin-3-yl)methyl)sulfinyl)-3-acetyl-8-bromo-5-chloroquinolin-4(1H)-one | 505.77 | 505 | $^1$H NMR (300 MHz, DMSO-d$_6$)δ10.00(br s, 1H), 8.46-8.45 (s, 1H), 8.11(s, 1H), 7.89-7.86(d, J = 8.46 Hz, 1H), 7.80(s, 1H), 7.79-7.71(m, 2H), 7.41-7.38(d, J = 8.37 Hz, 1H), 6.55(s, 1H), 4.79-4.75(d, J = 12.99 Hz, 1H), 4.43-4.38(d, J = 13.08 Hz, 1H), 2.70(s, 3H). |
| 100 | 3-acetyl-2-(((6-aminopyridin-3-yl)methyl)sulfinyl)-8-bromo-5-chloroquinolin-4(1H)-one | 454.72 | 454 | $^1$H NMR (300 MHz, DMSO-d$_6$)δ8.22-7.65 (m, 4H), 7.09-7.06(m, 1H), 4.36-4.32(m, 1H), 4.14-4.11(m, 1H), 2.88(s, 3H). |
| 101 | 8-bromo-5-chloro-3-(cyclopropanecarbonyl)-2-((4-((trifluoromethyl)thio)benzyl)sulfinyl)quinolin-4(1H)-one | 564.82 | 564 | $^1$H NMR (300 MHz, DMSO-d$_6$)δ10.11(br s, 1H), 8.08-8.06 (d, J = 8.43 Hz, 1H), 7.55-7.52(d, J = 7.71 Hz, 2H), 7.45-7.43(d, J = 8.37 Hz, 1H), 7.20-7.17(d, J = 7.71 Hz, 2H), 4.65-4.61(d, J = 12.66 Hz, 1H), 4.42-4.37(d, J = 12.87 Hz, 1H), 3.55-3.47(m, 1H), 1.28-1.02(m, 4H). |
| 102 | 3-acetyl-8-bromo-5-chloro-2-(((2-methyl-6-(trifluoromethyl)pyridin-3-yl)methyl)sulfinyl)quinolin-4(1H)-one | 521.73 | 521 | $^1$H NMR (300 MHz, DMSO-d$_6$)δ10.32(br s, 1H), 8.02-7.99(d, J = 8.46 Hz, 1H), 7.68-7.65(d, J = 7.98 Hz, 1H), 7.55-7.52(d, J = 7.89 Hz, 1H), 7.45-7.42(d, J = 8.49 Hz, 1H), 4.95-4.91(d, J = 13.41 Hz, 1H), 4.51-4.46(d, J = 13.08 Hz, 2H), 2.68(s, 3H), 2.61(s, 3H). |
| 103 | N-(4-(((3-acetyl-8-bromo-5-chloro-4-oxo-1,4-dihydroquinolin-2-yl)sulfinyl)methyl)phenyl)methanesulfonamide | 531.82 | 531 | $^1$H NMR (300 MHz, DMSO-d$_6$)δ10.25(br s, 1H), 8.01 (m, 1H), 7.67-7.64(m, 1H), 7.41-6.98(m, 6H), 4.79-4.50(m, 2H), 4.30-4.22(m, 2H), 2.81(s, 3H), 2.68(s, 3H). |
| 104 | 3-acetyl-8-bromo-5-chloro-2-(((6-chloropyridin-3-yl)methyl)sulfinyl)quinolin-4(1H)-one | 474.15 | 474 | $^1$H NMR (300 MHz, CDCl$_3$)δ10.20 (s, 1H), 8.10 (s, 1H), 7.76 (d, J = 8.4 Hz, 1H), 7.51 (d, J = 7.8 Hz, 1H), 7.36 (d, J = 8.4 Hz, 1H), 7.24 (d, J = 8.1 Hz, 1H), 4.41 (dd, J = 26.8, 13.0 Hz, 2H), 2.86 (s, 3H). |

TABLE 4-continued

| Compound No. | Formula Name | MW (molecular weight) | LC/MS data | $^1$H NMR |
|---|---|---|---|---|
| 105 | 3-acetyl-8-bromo-5-chloro-2-(((6-((2-methoxyethyl)amino)pyridin-3-yl)methyl)sulfinyl)quinolin-4(1H)-one | 512.80 | 512 | $^1$H NMR(300 MHz, CDCl$_3$) δ 12.59 (s, 1H), 7.75 (d, J = 8.2 Hz, 1H), 7.63 (d, J = 7.6 Hz, 1H), 7.04 (d, J = 8.2 Hz, 2H), 6.11 (d, J = 7.6 Hz, 1H), 4.61-4.53 (m, 1H), 3.90 3.84 (m, 1H), 3.71 3.65 (m, 2H), 3.64 3.55 (m, 2H), 3.41 (s, 3H), 3.33 (s, 3H). |
| 106 | 3-acetyl-8-bromo-5-chloro-2-(((4-methyl-1,2,5-oxadiazol-3-yl)methyl)sulfinyl)quinolin-4(1H)-one | 444.68 | 444 | $^1$H NMR (300 MHz, DMSO-d$_6$)δ 7.76-7.73(d, J = 8.5 Hz, 1H), 7.08-7.06(d, J = 8.5 Hz, 1H), 4.52-4.48(d, J = 12.0 Hz, 1H), 4.28-4.23 (d, J = 12.0 Hz, 1H), 2.50(s, 3H), 2.44(s, 3H). |
| 107 | 2-(((1H-pyrrolo[2,3-b]pyridin-5-yl)methyl)sulfinyl)-3-acetyl-8-bromo-5-chloroquinolin-4(1H)-one | 478.75 | 478 | $^1$H NMR (300 MHz, DMSO-d$_6$)δ11.62(br s, 1H), 8.00-7.32 (m, 5H), 6.38(s, 1H), 4.62-4.58(m, 1H), 4.20-4.10(m, 1H), 2.60(s, 3H). |

Example 3. Evaluation of the Active Ingredient of the Present Invention (Evaluation of Inhibitory Effect of the Active Ingredient of the Present Invention on DNA Binding of c-Myc/Max)

3-1. Protein Assay

1) Preparation of recombinant c-Myc and Max proteins
First, the recombinant c-Myc and Max proteins were prepared as in the method described in the documents: K. C. Jung et al., Fatty acids, inhibitors for the DNA binding of c-Myc/Max dimer, suppress proliferation and induce apoptosis of differentiated HL-60 human leukemia cell, Leukemia, 2006, 20(1), 122-7, or Kyung-Chae Jeong et al., Small-molecule inhibitors of c-Myc transcriptional factor suppress proliferation and induce apoptosis of promyelocytic leukemia cell via cell cycle arrest, Mol. BioSyst., 2010, 6, 1503-1509.

2) Electrophoretic Mobility Shift Assay (EMSA)
The inhibitory activity of each candidate compound against DNA binding of the recombinant c-Myc/Max was measured by electrophoretic mobility shift assay (EMSA). The ratio of protein-DNA complexes in each sample was evaluated by measuring the intensity of a band. The oligonucleotide (E-box, 5'-biotin-GGAAGCAGACCACGT-GGTCTGCTTCC-3'-biotin) corresponding to the Myc-Max binding site (consensus) was dimerized through an annealing process. After the protein mixture was incubated at room temperature for 5 minutes, a DMSO solution containing each candidate compound was added thereto. The mixture was further incubated for 5 minutes, and the biotinylated DNA was added thereto. To achieve a state of equilibrium, the final mixture was incubated at room temperature for 10 minutes. The protein-DNA complexes were separated from unbound free DNA by pre-electrophoresis using 8% polyacrylamide gel and a 01×TBE buffer. After pre-electrophoresis, electrophoresis was performed at 120 V for 1 hour in a 1×TBE buffer. Each band was visualized by using HRP-conjugated streptavidin and an ECL solution, and the intensity of the band was measured by using image analysis software.

3-2. Cell Based Assay

Commercially available bladder cancer, prostate cancer, lung cancer, breast cancer, blood cancer, pancreatic cancer, colorectal cancer, brain cancer, neuroblastoma, melanoma, liver cancer, cervical carcinoma, ovarian cancer, renal cancer, and papilloma cell lines were each treated with trypsin-EDTA and cultured, followed by being seeded in each well of a 96 well plate. After 24 hours of treatment at constant temperature, the respective cells were treated with the candidate compound so that a final concentration became 0 to 2 μM. The treated cells were additionally cultured for 72 hours, and cell viability was measured by using an ATP detection method (CellTiter-Glo® Luminescent Cell Viability Assay, Promega).

IC$_{50}$ values calculated through in vitro assay and proliferation assay results of the compounds according to the present invention are summarized and shown in the following Tables 5 to 13.

TABLE 5

| Compound | Bladder cancer cell line | | | | | | |
|---|---|---|---|---|---|---|---|
| No. | KU-19-19 | 253J | 5637 | J82 | T24 | MBT-2 | UM-UC-3 |
| 1 | 1.94 μM | 1.35 μM | 1.67 μM | >2 μM | 1.34 μM | 1.19 μM | 1.51 μM |
| 2 | >2 μM | >2 μM | >2 μM | >2 μM | >2 μM | >2 μM | >2 μM |
| 3 | >2 μM | >2 μM | >2 μM | >2 μM | >2 μM | >2 μM | >2 μM |
| 4 | 1.05 μM | 1.00 μM | 1.91 μM | >2 μM | 1.31 μM | 0.96 μM | 1.33 μM |
| 5 | >2 μM | >2 μM | >2 μM | >2 μM | >2 μM | >2 μM | >2 μM |
| 6 | >2 μM | 1.22 μM | 1.69 μM | >2 μM | 1.42 μM | 1.44 μM | 1.46 μM |
| 7 | >2 μM | >2 μM | >2 μM | >2 μM | >2 μM | >2 μM | >2 μM |
| 8 | >2 μM | >2 μM | >2 μM | >2 μM | >2 μM | >2 μM | >2 μM |
| 9 | 1.97 μM | 1.10 μM | 1.63 μM | >2 μM | 1.16 μM | 1.20 μM | 1.18 μM |
| 10 | >2 μM | >2 μM | >2 μM | >2 μM | >2 μM | >2 μM | >2 μM |
| 11 | >2 μM | 1.41 μM | >2 μM | >2 μM | 1.83 μM | >2 μM | 1.49 μM |
| 12 | >2 μM | >2 μM | >2 μM | >2 μM | >2 μM | >2 μM | >2 μM |
| 13 | >2 μM | >2 μM | >2 μM | >2 μM | >2 μM | >2 μM | >2 μM |

TABLE 5-continued

| Compound | Bladder cancer cell line | | | | | | |
|---|---|---|---|---|---|---|---|
| No. | KU-19-19 | 253J | 5637 | J82 | T24 | MBT-2 | UM-UC-3 |
| 14 | >2 μM | >2 μM | >2 μM | >2 μM | >2 μM | >2 μM | >2 μM |
| 15 | 1.91 μM | >2 μM | >2 μM | >2 μM | >2 μM | >2 μM | >2 μM |
| 16 | >2 μM | >2 μM | >2 μM | >2 μM | >2 μM | >2 μM | >2 μM |
| 17 | >2 μM | >2 μM | >2 μM | >2 μM | >2 μM | >2 μM | >2 μM |
| 18 | >2 μM | >2 μM | >2 μM | >2 μM | >2 μM | >2 μM | >2 μM |
| 19 | >2 μM | >2 μM | >2 μM | >2 μM | >2 μM | >2 μM | >2 μM |
| 20 | >2 μM | >2 μM | >2 μM | >2 μM | >2 μM | >2 μM | >2 μM |
| 21 | >2 μM | >2 μM | >2 μM | >2 μM | >2 μM | >2 μM | >2 μM |
| 22 | >2 μM | >2 μM | >2 μM | >2 μM | >2 μM | >2 μM | >2 μM |
| 23 | >2 μM | >2 μM | >2 μM | >2 μM | >2 μM | >2 μM | >2 μM |
| 24 | >2 μM | >2 μM | >2 μM | >2 μM | >2 μM | >2 μM | >2 μM |
| 25 | >2 μM | >2 μM | >2 μM | >2 μM | >2 μM | >2 μM | >2 μM |
| 26 | >2 μM | >2 μM | 1.60 μM | >2 μM | >2 μM | >2 μM | >2 μM |
| 27 | >2 μM | >2 μM | >2 μM | >2 μM | >2 μM | >2 μM | >2 μM |
| 28 | 1.46 μM | 0.74 μM | 1.03 μM | 1.33 μM | 0.82 μM | 0.79 μM | 0.79 μM |
| 29 | 1.68 μM | 0.96 μM | 1.33 μM | >2 μM | 1.09 μM | 1.20 μM | 1.13 μM |
| 30 | >2 μM | >2 μM | >2 μM | >2 μM | >2 μM | >2 μM | >2 μM |
| 31 | 1.45 μM | 0.89 μM | 1.23 μM | 1.38 μM | 1.12 μM | 1.28 μM | 1.02 μM |
| 32 | >2 μM | >2 μM | >2 μM | >2 μM | >2 μM | >2 μM | >2 μM |
| 33 | 1.42 μM | 1.39 μM | >2 μM | >2 μM | 1.03 μM | 0.90 μM | 1.11 μM |
| 34 | >2 μM | >2 μM | >2 μM | >2 μM | >2 μM | >2 μM | >2 μM |
| 35 | >2 μM | >2 μM | >2 μM | >2 μM | >2 μM | >2 μM | >2 μM |
| 36 | >2 μM | >2 μM | >2 μM | >2 μM | >2 μM | 1.28 μM | >2 μM |
| 37 | >2 μM | >2 μM | >2 μM | >2 μM | >2 μM | >2 μM | >2 μM |
| 38 | >2 μM | >2 μM | >2 μM | >2 μM | >2 μM | >2 μM | >2 μM |
| 39 | >2 μM | >2 μM | >2 μM | >2 μM | >2 μM | >2 μM | >2 μM |
| 40 | >2 μM | >2 μM | >2 μM | >2 μM | >2 μM | >2 μM | >2 μM |
| 41 | >2 μM | >2 μM | >2 μM | >2 μM | >2 μM | >2 μM | >2 μM |
| 42 | >2 μM | >2 μM | >2 μM | >2 μM | >2 μM | >2 μM | 1.89 μM |
| 43 | >2 μM | >2 μM | >2 μM | >2 μM | >2 μM | >2 μM | >2 μM |
| 44 | 1.27 μM | 1.24 μM | 1.35 μM | 2.07 μM | 0.92 μM | 1.15 μM | 0.97 μM |
| 45 | >2 μM | >2 μM | >2 μM | >2 μM | >2 μM | >2 μM | >2 μM |
| 46 | 1.80 μM | 1.96 μM | 1.77 μM | >2 μM | 1.57 μM | 1.84 μM | 1.22 μM |
| 47 | >2 μM | >2 μM | >2 μM | >2 μM | >2 μM | >2 μM | >2 μM |
| 48 | >2 μM | >2 μM | >2 μM | >2 μM | >2 μM | >2 μM | 1.82 μM |
| 49 | >2 μM | >2 μM | >2 μM | >2 μM | >2 μM | >2 μM | >2 μM |
| 50 | 1.69 μM | 1.43 μM | 1.47 μM | >2 μM | 1.43 μM | 1.58 μM | 1.26 μM |
| 51 | 1.26 μM | 1.13 μM | 1.07 μM | >2 μM | 0.89 μM | 0.76 μM | 0.63 μM |
| 52 | >2 μM | >2 μM | >2 μM | >2 μM | >2 μM | >2 μM | >2 μM |
| 53 | >2 μM | >2 μM | >2 μM | >2 μM | >2 μM | >2 μM | >2 μM |
| 54 | >2 μM | >2 μM | >2 μM | >2 μM | >2 μM | >2 μM | >2 μM |
| 55 | 1.38 μM | 1.33 μM | >2 μM | >2 μM | 1.54 μM | >2 μM | 1.58 μM |
| 56 | 0.90 μM | 1.11 μM | >2 μM | 1.46 μM | 0.98 μM | 1.18 μM | 1.25 μM |
| 57 | 1.83 μM | 1.92 μM | >2 μM | >2 μM | 1.79 μM | >2 μM | >2 μM |
| 58 | 0.92 μM | 0.92 μM | >2 μM | >2 μM | 0.82 μM | 0.86 μM | 1.22 μM |
| 59 | 1.23 μM | 1.14 μM | >2 μM | >2 μM | 1.11 μM | 1.30 μM | 1.37 μM |
| 60 | 1.56 μM | 1.71 μM | >2 μM | >2 μM | 1.72 μM | >2 μM | >2 μM |
| 61 | >2 μM | >2 μM | >2 μM | >2 μM | >2 μM | >2 μM | >2 μM |
| 62 | >2 μM | >2 μM | >2 μM | >2 μM | >2 μM | >2 μM | >2 μM |
| 63 | >2 μM | >2 μM | >2 μM | >2 μM | >2 μM | >2 μM | >2 μM |
| 64 | 1.41 μM | 0.95 μM | 1.52 μM | 1.96 μM | 1.04 μM | 0.84 μM | 1.06 μM |
| 65 | >2 μM | >2 μM | >2 μM | >2 μM | >2 μM | >2 μM | >2 μM |
| 66 | >2 μM | >2 μM | >2 μM | >2 μM | >2 μM | >2 μM | >2 μM |
| 67 | >2 μM | >2 μM | >2 μM | >2 μM | >2 μM | >2 μM | >2 μM |
| 68 | 1.25 μM | 0.97 μM | 1.46 μM | 1.49 μM | 1.47 μM | 1.07 μM | 1.11 μM |
| 69 | 1.50 μM | 1.08 μM | 1.62 μM | 1.89 μM | 1.50 μM | 1.26 μM | 1.20 μM |
| 70 | 1.75 μM | 1.04 μM | 1.73 μM | 1.94 μM | 1.69 μM | 1.33 μM | 1.26 μM |
| 71 | 1.60 μM | 1.11 μM | 1.51 μM | 1.98 μM | 1.39 μM | 1.47 μM | 1.61 μM |
| 72 | 1.37 μM | 0.83 μM | 1.64 μM | 1.63 μM | 1.25 μM | 1.01 μM | 0.82 μM |
| 73 | >2 μM | 1.34 μM | >2 μM | >2 μM | 1.34 μM | 1.00 μM | 1.62 μM |
| 74 | 1.64 μM | 0.81 μM | 1.60 μM | >2 μM | 1.07 μM | 1.15 μM | 1.54 μM |
| 75 | 1.21 μM | 0.86 μM | 1.57 μM | 1.48 μM | 1.33 μM | 1.05 μM | 1.01 μM |
| 76 | 1.86 μM | 1.24 μM | >2 μM | >2 μM | 1.79 μM | 1.86 μM | 1.39 μM |
| 77 | 1.38 μM | 0.90 μM | 1.68 μM | 1.62 μM | 1.51 μM | 1.45 μM | 1.18 μM |
| 78 | >2 μM | 1.29 μM | >2 μM | >2 μM | 1.80 μM | 1.53 μM | 1.39 μM |
| 79 | >2 μM | >2 μM | >2 μM | >2 μM | >2 μM | >2 μM | >2 μM |
| 80 | >2 μM | >2 μM | >2 μM | >2 μM | >2 μM | >2 μM | >2 μM |
| 81 | >2 μM | >2 μM | >2 μM | >2 μM | >2 μM | >2 μM | >2 μM |
| 82 | >2 μM | >2 μM | >2 μM | >2 μM | >2 μM | >2 μM | >2 μM |
| 83 | 1.60 μM | 1.42 μM | 1.37 μM | >2 μM | 1.50 μM | 1.35 μM | 1.31 μM |
| 84 | 1.50 μM | 0.87 μM | >2 μM | >2 μM | 1.03 μM | 0.67 μM | 0.76 μM |
| 85 | >2 μM | >2 μM | >2 μM | >2 μM | >2 μM | >2 μM | >2 μM |
| 86 | 1.41 μM | 1.06 μM | 1.36 μM | 1.61 μM | 1.02 μM | 0.81 μM | 1.26 μM |
| 87 | >2 μM | >2 μM | >2 μM | >2 μM | >2 μM | >2 μM | >2 μM |
| 88 | >2 μM | >2 μM | >2 μM | >2 μM | >2 μM | >2 μM | >2 μM |
| 89 | >2 μM | 1.84 μM | >2 μM | >2 μM | 1.75 μM | 1.27 μM | 1.47 μM |

TABLE 5-continued

| Compound No. | Bladder cancer cell line | | | | | | |
|---|---|---|---|---|---|---|---|
| | KU-19-19 | 253J | 5637 | J82 | T24 | MBT-2 | UM-UC-3 |
| 90 | >2 μM | >2 μM | >2 μM | >2 μM | >2 μM | >2 μM | >2 μM |
| 91 | >2 μM | >2 μM | >2 μM | >2 μM | >2 μM | 1.37 μM | 1.56 μM |
| 92 | >2 μM | >2 μM | >2 μM | >2 μM | >2 μM | >2 μM | >2 μM |
| 93 | >2 μM | >2 μM | >2 μM | >2 μM | >2 μM | >2 μM | >2 μM |
| 94 | >2 μM | >2 μM | >2 μM | >2 μM | >2 μM | 1.53 μM | >2 μM |
| 95 | 1.29 μM | 0.77 μM | 1.23 μM | 1.47 μM | 0.98 μM | 0.80 μM | 1.06 μM |
| 96 | >2 μM | 1.49 μM | >2 μM | >2 μM | 1.66 μM | 1.06 μM | 1.63 μM |
| 97 | 1.62 μM | 1.20 μM | 1.91 μM | >2 μM | 1.20 μM | 0.81 μM | 1.27 μM |
| 98 | 1.90 μM | 1.38 μM | >2 μM | >2 μM | 1.32 μM | 0.84 μM | 1.52 μM |
| 99 | 1.12 μM | 0.80 μM | 1.62 μM | 1.50 μM | 0.85 μM | 0.47 μM | 0.77 μM |
| 100 | >2 μM | >2 μM | >2 μM | >2 μM | >2 μM | >2 μM | >2 μM |
| 101 | >2 μM | 1.82 μM | >2 μM | >2 μM | >2 μM | >2 μM | 1.93 μM |
| 102 | 1.58 μM | 0.83 μM | >2 μM | >2 μM | 1.03 μM | 0.77 μM | 1.07 μM |
| 103 | >2 μM | >2 μM | >2 μM | >2 μM | >2 μM | >2 μM | >2 μM |
| 104 | 1.50 μM | 0.87 μM | >2 μM | >2 μM | 1.03 μM | 0.71 μM | 1.13 μM |
| 105 | >2 μM | >2 μM | >2 μM | >2 μM | >2 μM | >2 μM | >2 μM |
| 106 | >2 μM | >2 μM | >2 μM | >2 μM | >2 μM | >2 μM | >2 μM |
| 107 | >2 μM | >2 μM | >2 μM | >2 μM | >2 μM | >2 μM | >2 μM |

TABLE 6

| Compound No. | Prostate cancer cell line | | | | |
|---|---|---|---|---|---|
| | PC-3 | DU145 | DU145/TXR | LNcap | CWR22 |
| 1 | 1.64 μM | 1.90 μM | 1.65 μM | >2 μM | 1.83 μM |
| 2 | >2 μM | >2 μM | >2 μM | >2 μM | >2 μM |
| 3 | >2 μM | >2 μM | >2 μM | >2 μM | >2 μM |
| 4 | 1.52 μM | 1.41 μM | 1.19 μM | >2 μM | 1.67 μM |
| 5 | >2 μM | >2 μM | >2 μM | >2 μM | >2 μM |
| 6 | 1.68 μM | 1.80 μM | 1.54 μM | >2 μM | 1.99 μM |
| 7 | >2 μM | >2 μM | >2 μM | >2 μM | >2 μM |
| 8 | >2 μM | >2 μM | >2 μM | >2 μM | >2 μM |
| 9 | 1.47 μM | 1.59 μM | 1.35 μM | >2 μM | 1.60 μM |
| 10 | >2 μM | >2 μM | >2 μM | >2 μM | >2 μM |
| 11 | >2 μM | >2 μM | 1.81 μM | >2 μM | >2 μM |
| 12 | >2 μM | >2 μM | >2 μM | >2 μM | >2 μM |
| 13 | >2 μM | >2 μM | >2 μM | >2 μM | >2 μM |
| 14 | >2 μM | >2 μM | >2 μM | >2 μM | >2 μM |
| 15 | >2 μM | >2 μM | 1.88 μM | >2 μM | >2 μM |
| 16 | >2 μM | >2 μM | >2 μM | >2 μM | >2 μM |
| 17 | >2 μM | >2 μM | >2 μM | >2 μM | >2 μM |
| 18 | >2 μM | >2 μM | >2 μM | >2 μM | >2 μM |
| 19 | >2 μM | >2 μM | >2 μM | >2 μM | >2 μM |
| 20 | >2 μM | >2 μM | >2 μM | >2 μM | >2 μM |
| 21 | >2 μM | >2 μM | >2 μM | >2 μM | >2 μM |
| 22 | >2 μM | >2 μM | >2 μM | >2 μM | >2 μM |
| 23 | >2 μM | >2 μM | >2 μM | >2 μM | >2 μM |
| 24 | >2 μM | >2 μM | >2 μM | >2 μM | >2 μM |
| 25 | >2 μM | >2 μM | >2 μM | >2 μM | >2 μM |
| 26 | >2 μM | >2 μM | >2 μM | >2 μM | >2 μM |
| 27 | >2 μM | >2 μM | >2 μM | >2 μM | >2 μM |
| 28 | 1.16 μM | 1.28 μM | 1.01 μM | 1.34 μM | 1.07 μM |
| 29 | 1.46 μM | 1.73 μM | 0.96 μM | 1.55 μM | 1.77 μM |
| 30 | >2 μM | >2 μM | >2 μM | >2 μM | >2 μM |
| 31 | 1.41 μM | 1.44 μM | 0.93 μM | 1.64 μM | 1.59 μM |
| 32 | >2 μM | >2 μM | >2 μM | >2 μM | >2 μM |
| 33 | 1.58 μM | 1.63 μM | 1.34 μM | 1.84 μM | 1.34 μM |
| 34 | >2 μM | >2 μM | 1.59 μM | >2 μM | >2 μM |
| 35 | >2 μM | >2 μM | >2 μM | >2 μM | >2 μM |
| 36 | >2 μM | >2 μM | >2 μM | >2 μM | >2 μM |
| 37 | >2 μM | >2 μM | >2 μM | >2 μM | >2 μM |
| 38 | >2 μM | >2 μM | >2 μM | >2 μM | >2 μM |
| 39 | >2 μM | >2 μM | >2 μM | >2 μM | >2 μM |
| 40 | >2 μM | >2 μM | >2 μM | >2 μM | >2 μM |
| 41 | >2 μM | >2 μM | >2 μM | >2 μM | >2 μM |
| 42 | >2 μM | >2 μM | >2 μM | >2 μM | >2 μM |
| 43 | >2 μM | >2 μM | >2 μM | >2 μM | >2 μM |
| 44 | 1.49 μM | 1.60 μM | 1.00 μM | 1.98 μM | 1.58 μM |
| 45 | >2 μM | >2 μM | >2 μM | >2 μM | >2 μM |
| 46 | >2 μM | >2 μM | 1.56 μM | >2 μM | >2 μM |
| 47 | >2 μM | >2 μM | >2 μM | >2 μM | >2 μM |
| 48 | >2 μM | >2 μM | 1.57 μM | >2 μM | >2 μM |
| 49 | >2 μM | >2 μM | >2 μM | >2 μM | >2 μM |
| 50 | 1.60 μM | 1.77 μM | 1.28 μM | >2 μM | >2 μM |
| 51 | 1.36 μM | 1.24 μM | 1.12 μM | 1.24 μM | 1.03 μM |
| 52 | >2 μM | >2 μM | >2 μM | >2 μM | >2 μM |
| 53 | >2 μM | >2 μM | >2 μM | >2 μM | >2 μM |
| 54 | >2 μM | >2 μM | >2 μM | >2 μM | >2 μM |
| 55 | 1.93 μM | >2 μM | 1.39 μM | >2 μM | >2 μM |
| 56 | 1.30 μM | 1.42 μM | 0.86 μM | 1.82 μM | 1.55 μM |
| 57 | >2 μM | >2 μM | >2 μM | >2 μM | >2 μM |
| 58 | 1.30 μM | 1.23 μM | 1.21 μM | 1.44 μM | 1.20 μM |
| 59 | 1.64 μM | 1.49 μM | 1.14 μM | >2 μM | 1.56 μM |
| 60 | 1.82 μM | >2 μM | 1.26 μM | >2 μM | >2 μM |
| 61 | >2 μM | >2 μM | >2 μM | >2 μM | >2 μM |
| 62 | >2 μM | >2 μM | >2 μM | >2 μM | >2 μM |
| 63 | >2 μM | >2 μM | >2 μM | >2 μM | >2 μM |
| 64 | 1.43 μM | 1.57 μM | 1.16 μM | 1.71 μM | 1.49 μM |
| 65 | >2 μM | >2 μM | >2 μM | >2 μM | >2 μM |
| 66 | >2 μM | >2 μM | >2 μM | >2 μM | >2 μM |
| 67 | >2 μM | >2 μM | >2 μM | >2 μM | >2 μM |
| 68 | 1.24 μM | 0.83 μM | 0.94 μM | >2 μM | 1.62 μM |
| 69 | 1.30 μM | 1.00 μM | 1.11 μM | >2 μM | 1.87 μM |
| 70 | 1.25 μM | 1.09 μM | 1.19 μM | >2 μM | 1.89 μM |
| 71 | 1.70 μM | 1.74 μM | 1.23 μM | >2 μM | >2 μM |
| 72 | 1.28 μM | 0.71 μM | 0.89 μM | 1.91 μM | 1.52 μM |
| 73 | 1.87 μM | >2 μM | 1.77 μM | >2 μM | >2 μM |
| 74 | 1.47 μM | >2 μM | 1.46 μM | 1.76 μM | 1.72 μM |
| 75 | 1.44 μM | 1.02 μM | 1.03 μM | >2 μM | 1.88 μM |
| 76 | 1.70 μM | 1.14 μM | 1.17 μM | >2 μM | >2 μM |
| 77 | 1.48 μM | 0.93 μM | 0.93 μM | >2 μM | >2 μM |
| 78 | 1.53 μM | 1.15 μM | 1.38 μM | >2 μM | >2 μM |
| 79 | >2 μM | >2 μM | >2 μM | >2 μM | >2 μM |
| 80 | >2 μM | >2 μM | >2 μM | >2 μM | >2 μM |
| 81 | >2 μM | >2 μM | >2 μM | >2 μM | >2 μM |
| 82 | >2 μM | >2 μM | >2 μM | >2 μM | >2 μM |
| 83 | >2 μM | 1.34 μM | 1.05 μM | >2 μM | 1.94 μM |
| 84 | >2 μM | 1.39 μM | 1.23 μM | >2 μM | 1.42 μM |
| 85 | >2 μM | >2 μM | >2 μM | >2 μM | >2 μM |
| 86 | 1.67 μM | 1.31 μM | 1.11 μM | >2 μM | 1.26 μM |
| 87 | >2 μM | >2 μM | >2 μM | >2 μM | >2 μM |
| 88 | >2 μM | >2 μM | >2 μM | >2 μM | >2 μM |
| 89 | >2 μM | >2 μM | 1.96 μM | >2 μM | >2 μM |
| 90 | >2 μM | >2 μM | >2 μM | >2 μM | >2 μM |
| 91 | >2 μM | >2 μM | 1.98 μM | >2 μM | >2 μM |
| 92 | >2 μM | >2 μM | >2 μM | >2 μM | >2 μM |
| 93 | >2 μM | >2 μM | >2 μM | >2 μM | >2 μM |
| 94 | >2 μM | >2 μM | >2 μM | >2 μM | >2 μM |

TABLE 6-continued

| Compound No. | Prostate cancer cell line | | | | |
|---|---|---|---|---|---|
| | PC-3 | DU145 | DU145/TXR | LNcap | CWR22 |
| 95 | 1.70 μM | 0.84 μM | 0.94 μM | 1.98 μM | 1.08 μM |
| 96 | >2 μM | 1.74 μM | 1.77 μM | >2 μM | 1.90 μM |
| 97 | 1.70 μM | 1.28 μM | 1.50 μM | >2 μM | 1.48 μM |
| 98 | >2 μM | 1.92 μM | 1.91 μM | >2 μM | 1.55 μM |
| 99 | 1.51 μM | 0.97 μM | 1.06 μM | >2 μM | 1.24 μM |
| 100 | >2 μM | >2 μM | >2 μM | >2 μM | >2 μM |
| 101 | >2 μM | 1.34 μM | 1.42 μM | >2 μM | >2 μM |
| 102 | 1.83 μM | 1.65 μM | 1.12 μM | >2 μM | 1.49 μM |
| 103 | >2 μM | >2 μM | >2 μM | >2 μM | >2 μM |
| 104 | >2 μM | 1.64 μM | 1.23 μM | >2 μM | 1.55 μM |
| 105 | >2 μM | >2 μM | >2 μM | >2 μM | >2 μM |
| 106 | >2 μM | >2 μM | >2 μM | >2 μM | >2 μM |
| 107 | >2 μM | >2 μM | >2 μM | >2 μM | >2 μM |

TABLE 7

| Compound No. | Lung cancer cell line | | | | | | | |
|---|---|---|---|---|---|---|---|---|
| | NCI-H522 | NCI-H1437 | A549 | NCI-H460 | MRC-5 | DMS 114 | NCI-H23 | NCI-H1299 |
| 1 | >2 μM | >10 μM | >2 μM | >2 μM | 1.34 μM | >2 μM | 1.34 μM | 1.88 μM |
| 2 | >2 μM | >10 μM | >2 μM | >2 μM | >2 μM | >2 μM | >2 μM | >2 μM |
| 3 | >2 μM | >10 μM | >2 μM | >2 μM | >2 μM | >2 μM | >2 μM | >2 μM |
| 4 | >2 μM | >2 μM | 1.97 μM | 1.65 μM | 0.91 μM | >2 μM | 0.92 μM | 1.40 μM |
| 5 | >2 μM | >10 μM | >2 μM | >2 μM | >2 μM | >2 μM | >2 μM | >2 μM |
| 6 | >2 μM | >10 μM | >2 μM | >2 μM | >2 μM | >2 μM | 1.31 μM | 1.84 μM |
| 7 | >2 μM | >10 μM | >2 μM | >2 μM | >2 μM | >2 μM | >2 μM | >2 μM |
| 8 | >2 μM | >10 μM | >2 μM | >2 μM | >2 μM | >2 μM | >2 μM | >2 μM |
| 9 | >2 μM | >10 μM | >2 μM | >2 μM | >2 μM | >2 μM | 0.90 μM | 1.26 μM |
| 10 | >2 μM | >10 μM | >2 μM | >2 μM | >2 μM | >2 μM | >2 μM | >2 μM |
| 11 | >2 μM | >10 μM | >2 μM | >2 μM | >2 μM | >2 μM | 1.55 μM | >2 μM |
| 12 | >2 μM | >10 μM | >2 μM | >2 μM | >2 μM | >2 μM | >2 μM | >2 μM |
| 13 | >2 μM | >10 μM | >2 μM | >2 μM | >2 μM | >2 μM | >2 μM | >2 μM |
| 14 | >2 μM | >10 μM | >2 μM | >2 μM | >2 μM | >2 μM | >2 μM | >2 μM |
| 15 | >2 μM | >10 μM | >2 μM | >2 μM | >2 μM | >2 μM | 1.56 μM | >2 μM |
| 16 | >2 μM | >10 μM | >2 μM | >2 μM | >2 μM | >2 μM | >2 μM | >2 μM |
| 17 | >2 μM | >10 μM | >2 μM | >2 μM | >2 μM | >2 μM | >2 μM | >2 μM |
| 18 | >2 μM | >10 μM | >2 μM | >2 μM | >2 μM | >2 μM | >2 μM | >2 μM |
| 19 | >2 μM | >10 μM | >2 μM | >2 μM | >2 μM | >2 μM | >2 μM | >2 μM |
| 20 | >2 μM | >2 μM | >2 μM | 1.58 μM | >2 μM | >2 μM | 1.39 μM | 1.58 μM |
| 21 | >2 μM | >10 μM | >2 μM | >2 μM | >2 μM | >2 μM | >2 μM | >2 μM |
| 22 | >2 μM | >10 μM | >2 μM | >2 μM | >2 μM | >2 μM | >2 μM | >2 μM |
| 23 | >2 μM | >10 μM | >2 μM | >2 μM | >2 μM | >2 μM | >2 μM | >2 μM |
| 24 | >2 μM | >10 μM | >2 μM | >2 μM | >2 μM | >2 μM | >2 μM | >2 μM |
| 25 | >2 μM | >10 μM | >2 μM | >2 μM | >2 μM | >2 μM | >2 μM | >2 μM |
| 26 | >2 μM | >10 μM | >2 μM | >2 μM | >2 μM | >2 μM | >2 μM | >2 μM |
| 27 | >2 μM | >10 μM | >2 μM | >2 μM | >2 μM | >2 μM | >2 μM | >2 μM |
| 28 | 1.88 μM | >10 μM | >2 μM | 1.60 μM | 0.70 μM | >2 μM | 0.75 μM | 1.11 μM |
| 29 | >2 μM | >10 μM | >2 μM | 1.77 μM | >2 μM | >2 μM | 0.91 μM | 1.42 μM |
| 30 | >2 μM | >10 μM | >2 μM | >2 μM | >2 μM | >2 μM | >2 μM | >2 μM |
| 31 | >2 μM | >10 μM | 1.72 μM | 1.42 μM | >2 μM | >2 μM | 0.81 μM | 1.22 μM |
| 32 | >2 μM | >10 μM | >2 μM | >2 μM | >2 μM | >2 μM | >2 μM | >2 μM |
| 33 | >2 μM | >10 μM | >2 μM | 1.78 μM | 0.82 μM | >2 μM | 0.86 μM | 1.38 μM |
| 34 | >2 μM | >10 μM | >2 μM | >2 μM | >2 μM | >2 μM | 1.39 μM | 2.00 μM |
| 35 | >2 μM | >10 μM | >2 μM | >2 μM | >2 μM | >2 μM | >2 μM | >2 μM |
| 36 | >2 μM | >10 μM | >2 μM | >2 μM | >2 μM | >2 μM | >2 μM | >2 μM |
| 37 | >2 μM | >10 μM | >2 μM | >2 μM | >2 μM | >2 μM | >2 μM | >2 μM |
| 38 | >2 μM | >10 μM | >2 μM | >2 μM | >2 μM | >2 μM | >2 μM | >2 μM |
| 39 | >2 μM | >10 μM | >2 μM | >2 μM | >2 μM | >2 μM | >2 μM | >2 μM |
| 40 | >2 μM | >10 μM | >2 μM | >2 μM | >2 μM | >2 μM | >2 μM | >2 μM |
| 41 | >2 μM | >10 μM | >2 μM | >2 μM | >2 μM | >2 μM | >2 μM | >2 μM |
| 42 | >2 μM | >10 μM | >2 μM | >2 μM | >2 μM | >2 μM | 1.84 μM | >2 μM |
| 43 | >2 μM | >10 μM | >2 μM | >2 μM | >2 μM | >2 μM | >2 μM | >2 μM |
| 44 | >2 μM | >10 μM | 1.87 μM | 1.75 μM | 0.96 μM | >2 μM | 0.96 μM | 1.28 μM |
| 45 | >2 μM | >10 μM | >2 μM | >2 μM | >2 μM | >2 μM | >2 μM | >2 μM |
| 46 | >2 μM | >10 μM | >2 μM | >2 μM | >2 μM | >2 μM | 1.27 μM | 1.87 μM |
| 47 | >2 μM | >10 μM | >2 μM | >2 μM | >2 μM | >2 μM | >2 μM | >2 μM |
| 48 | >2 μM | >10 μM | >2 μM | >2 μM | >2 μM | >2 μM | 1.51 μM | >2 μM |
| 49 | >2 μM | >10 μM | >2 μM | >2 μM | >2 μM | >2 μM | >2 μM | >2 μM |
| 50 | >2 μM | >10 μM | >2 μM | >2 μM | >2 μM | >2 μM | 1.14 μM | 1.94 μM |
| 51 | 1.73 μM | >10 μM | >2 μM | 1.62 μM | 0.58 μM | >2 μM | 0.77 μM | 1.13 μM |
| 52 | >2 μM | >10 μM | >2 μM | >2 μM | >2 μM | >2 μM | >2 μM | >2 μM |
| 53 | >2 μM | >10 μM | >2 μM | >2 μM | >2 μM | >2 μM | >2 μM | >2 μM |
| 54 | >2 μM | >10 μM | >2 μM | >2 μM | >2 μM | >2 μM | >2 μM | >2 μM |
| 55 | >2 μM | >10 μM | >2 μM | >2 μM | >2 μM | >2 μM | 1.28 μM | >2 μM |
| 56 | >2 μM | >10 μM | 1.70 μM | 1.90 μM | 1.24 μM | >2 μM | 1.04 μM | >2 μM |
| 57 | >2 μM | >10 μM | >2 μM | >2 μM | >2 μM | >2 μM | 1.83 μM | >2 μM |
| 58 | 1.94 μM | >10 μM | >2 μM | >2 μM | 0.76 μM | >2 μM | 0.80 μM | 1.15 μM |

TABLE 7-continued

| | Lung cancer cell line | | | | | | | |
|---|---|---|---|---|---|---|---|---|
| Compound No. | NCI-H522 | NCI-H1437 | A549 | NCI-H460 | MRC-5 | DMS 114 | NCI-H23 | NCI-H1299 |
| 59 | >2 μM | >10 μM | >2 μM | 1.81 μM | 1.03 μM | >2 μM | 0.92 μM | 1.45 μM |
| 60 | >2 μM | >10 μM | >2 μM | >2 μM | >2 μM | >2 μM | 1.37 μM | >2 μM |
| 61 | >2 μM | >10 μM | >2 μM | >2 μM | >2 μM | >2 μM | >2 μM | >2 μM |
| 62 | >2 μM | >10 μM | >2 μM | >2 μM | >2 μM | >2 μM | >2 μM | >2 μM |
| 63 | >2 μM | >10 μM | >2 μM | >2 μM | >2 μM | >2 μM | 1.70 μM | >2 μM |
| 64 | >2 μM | >10 μM | >2 μM | >2 μM | >2 μM | >2 μM | 0.98 μM | 1.35 μM |
| 65 | >2 μM | >10 μM | >2 μM | >2 μM | >2 μM | >2 μM | >2 μM | >2 μM |
| 66 | >2 μM | >10 μM | >2 μM | >2 μM | >2 μM | >2 μM | >2 μM | >2 μM |
| 67 | >2 μM | >10 μM | >2 μM | >2 μM | >2 μM | >2 μM | >2 μM | >2 μM |
| 68 | >2 μM | >10 μM | 1.38 μM | 1.41 μM | 0.95 μM | >2 μM | 0.77 μM | 1.24 μM |
| 69 | >2 μM | >10 μM | 1.78 μM | 1.62 μM | 1.05 μM | >2 μM | 1.13 μM | 1.31 μM |
| 70 | >2 μM | >10 μM | 1.99 μM | 1.61 μM | 1.01 μM | >2 μM | 1.03 μM | 1.47 μM |
| 71 | >2 μM | >10 μM | 1.79 μM | >2 μM | >2 μM | >2 μM | 1.46 μM | 1.64 μM |
| 72 | >2 μM | >10 μM | 1.79 μM | 1.54 μM | 0.72 μM | 1.94 μM | 0.71 μM | 1.21 μM |
| 73 | >2 μM | >10 μM | >2 μM | >2 μM | >2 μM | >2 μM | 1.52 μM | >2 μM |
| 74 | >2 μM | >10 μM | >2 μM | >2 μM | >2 μM | >2 μM | 1.08 μM | 1.42 μM |
| 75 | >2 μM | >10 μM | 1.70 μM | 1.73 μM | 1.09 μM | >2 μM | 1.19 μM | 1.06 μM |
| 76 | >2 μM | >10 μM | >2 μM | >2 μM | 1.57 μM | >2 μM | 1.22 μM | 1.67 μM |
| 77 | >2 μM | >10 μM | 1.84 μM | 1.51 μM | 1.06 μM | >2 μM | 0.96 μM | 1.32 μM |
| 78 | >2 μM | >10 μM | >2 μM | >2 μM | 1.50 μM | >2 μM | 1.34 μM | 1.81 μM |
| 79 | >2 μM | >10 μM | >2 μM | >2 μM | >2 μM | >2 μM | >2 μM | >2 μM |
| 80 | >2 μM | >10 μM | >2 μM | >2 μM | >2 μM | >2 μM | >2 μM | >2 μM |
| 81 | >2 μM | >10 μM | >2 μM | >2 μM | >2 μM | >2 μM | >2 μM | >2 μM |
| 82 | >2 μM | >10 μM | >2 μM | >2 μM | >2 μM | >2 μM | >2 μM | >2 μM |
| 83 | >2 μM | >10 μM | >2 μM | 1.54 μM | 1.75 μM | >2 μM | 1.25 μM | 1.45 μM |
| 84 | 1.35 μM | >10 μM | >2 μM | 1.48 μM | 1.29 μM | >2 μM | 0.86 μM | 1.05 μM |
| 85 | >2 μM | >10 μM | >2 μM | >2 μM | >2 μM | >2 μM | >2 μM | >2 μM |
| 86 | 1.09 μM | <2 μM | 1.19 μM | 1.49 μM | 1.13 μM | >2 μM | 0.71 μM | 1.23 μM |
| 87 | >2 μM | >10 μM | >2 μM | >2 μM | >2 μM | >2 μM | >2 μM | >2 μM |
| 88 | >2 μM | >10 μM | >2 μM | >2 μM | >2 μM | >2 μM | >2 μM | >2 μM |
| 89 | >2 μM | >10 μM | >2 μM | >2 μM | >2 μM | >2 μM | 1.47 μM | >2 μM |
| 90 | >2 μM | >10 μM | >2 μM | >2 μM | >2 μM | >2 μM | >2 μM | >2 μM |
| 91 | >2 μM | >10 μM | >2 μM | >2 μM | >2 μM | >2 μM | 1.80 μM | >2 μM |
| 92 | >2 μM | >10 μM | >2 μM | >2 μM | >2 μM | >2 μM | >2 μM | >2 μM |
| 93 | >2 μM | >10 μM | >2 μM | >2 μM | >2 μM | >2 μM | >2 μM | >2 μM |
| 94 | >2 μM | >10 μM | >2 μM | >2 μM | >2 μM | >2 μM | 2.07 μM | >2 μM |
| 95 | 1.01 μM | <2 μM | 0.94 μM | 1.40 μM | 0.97 μM | >2 μM | 0.72 μM | 1.06 μM |
| 96 | 1.82 μM | >10 μM | >2 μM | >2 μM | 1.81 μM | >2 μM | 1.34 μM | 1.80 μM |
| 97 | 1.32 μM | >10 μM | >2 μM | 1.46 μM | 1.43 μM | >2 μM | 1.09 μM | 1.48 μM |
| 98 | >2 μM | >10 μM | >2 μM | 1.68 μM | >2 μM | >2 μM | 1.64 μM | 1.81 μM |
| 99 | 1.13 μM | >10 μM | 1.29 μM | 1.18 μM | 1.13 μM | >2 μM | 0.92 μM | 1.06 μM |
| 100 | >2 μM | >10 μM | >2 μM | >2 μM | >2 μM | >2 μM | >2 μM | >2 μM |
| 101 | >2 μM | >10 μM | >2 μM | >2 μM | >2 μM | >2 μM | 1.33 μM | >2 μM |
| 102 | 1.49 μM | >10 μM | 1.64 μM | 1.44 μM | 1.43 μM | >2 μM | 1.26 μM | 1.11 μM |
| 103 | >2 μM | >10 μM | >2 μM | >2 μM | >2 μM | >2 μM | >2 μM | >2 μM |
| 104 | 1.41 μM | >10 μM | 1.68 μM | 1.51 μM | 1.62 μM | >2 μM | 1.27 μM | 1.17 μM |
| 105 | >2 μM | >10 μM | >2 μM | >2 μM | >2 μM | >2 μM | >2 μM | >2 μM |
| 106 | >2 μM | >10 μM | >2 μM | >2 μM | >2 μM | >2 μM | >2 μM | >2 μM |
| 107 | >2 μM | >10 μM | >2 μM | >2 μM | >2 μM | >2 μM | >2 μM | >2 μM |

TABLE 8

| | Breast cancer cell line | | | | | | | | |
|---|---|---|---|---|---|---|---|---|---|
| Compound No. | MCF7 | MDA-MB-231 | MDA-MB-231-L/DOX | SK-BR-3 | BT-20 | HCC1395 | HCC1954 | JIMT-1 | MDA-MB-468 |
| 1 | >2 μM | >2 μM | >2 μM | 1.09 μM | >2 μM | >10 μM | >2 μM | >10 μM | >2 μM |
| 2 | >2 μM | >2 μM | >2 μM | >2 μM | >2 μM | >10 μM | >2 μM | >10 μM | >2 μM |
| 3 | >2 μM | >2 μM | >2 μM | >2 μM | >2 μM | >10 μM | >2 μM | >10 μM | >2 μM |
| 4 | >2 μM | >2 μM | >2 μM | 0.91 μM | >2 μM | >10 μM | >2 μM | >10 μM | >2 μM |
| 5 | >2 μM | >2 μM | >2 μM | >2 μM | >2 μM | >10 μM | >2 μM | >10 μM | >2 μM |
| 6 | >2 μM | >2 μM | >2 μM | 1.12 μM | >2 μM | >10 μM | >2 μM | >10 μM | >2 μM |
| 7 | >2 μM | >2 μM | >2 μM | >2 μM | >2 μM | >10 μM | >2 μM | >10 μM | >2 μM |
| 8 | >2 μM | >2 μM | >2 μM | >2 μM | >2 μM | >10 μM | >2 μM | >10 μM | >2 μM |
| 9 | >2 μM | >2 μM | >2 μM | 0.85 μM | >2 μM | >10 μM | >2 μM | >10 μM | >2 μM |
| 10 | >2 μM | >2 μM | >2 μM | >2 μM | >2 μM | >10 μM | >2 μM | >10 μM | >2 μM |
| 11 | >2 μM | >2 μM | >2 μM | >2 μM | >2 μM | >10 μM | >2 μM | >10 μM | >2 μM |
| 12 | >2 μM | >2 μM | >2 μM | >2 μM | >2 μM | >10 μM | >2 μM | >10 μM | >2 μM |
| 13 | >2 μM | >2 μM | >2 μM | >2 μM | >2 μM | >10 μM | >2 μM | >10 μM | >2 μM |
| 14 | >2 μM | >2 μM | >2 μM | >2 μM | >2 μM | >10 μM | >2 μM | >10 μM | >2 μM |

TABLE 8-continued

| | Breast cancer cell line | | | | | | | | |
|---|---|---|---|---|---|---|---|---|---|
| Compound No. | MCF7 | MDA-MB-231 | MDA-MB-231-L/DOX | SK-BR-3 | BT-20 | HCC1395 | HCC1954 | JIMT-1 | MDA-MB-468 |
| 15 | >2 µM | >2 µM | >2 µM | 1.68 µM | >2 µM | >10 µM | >2 µM | >10 µM | >2 µM |
| 16 | >2 µM | >2 µM | >2 µM | >2 µM | >2 µM | >10 µM | >2 µM | >10 µM | >2 µM |
| 17 | >2 µM | >2 µM | >2 µM | >2 µM | >2 µM | >10 µM | >2 µM | >10 µM | >2 µM |
| 18 | >2 µM | >2 µM | >2 µM | >2 µM | >2 µM | >10 µM | >2 µM | >10 µM | >2 µM |
| 19 | >2 µM | >2 µM | >2 µM | >2 µM | >2 µM | >10 µM | >2 µM | >10 µM | >2 µM |
| 20 | >2 µM | >2 µM | >2 µM | >2 µM | >2 µM | >10 µM | >2 µM | >10 µM | >2 µM |
| 21 | >2 µM | >2 µM | >2 µM | >2 µM | >2 µM | >10 µM | >2 µM | >10 µM | >2 µM |
| 22 | >2 µM | >2 µM | >2 µM | >2 µM | >2 µM | >10 µM | >2 µM | >10 µM | >2 µM |
| 23 | >2 µM | >2 µM | >2 µM | >2 µM | >2 µM | >10 µM | >2 µM | >10 µM | >2 µM |
| 24 | >2 µM | >2 µM | >2 µM | >2 µM | >2 µM | >10 µM | >2 µM | >10 µM | >2 µM |
| 25 | >2 µM | >2 µM | >2 µM | 1.72 µM | >2 µM | >10 µM | >2 µM | >10 µM | >2 µM |
| 26 | >2 µM | >2 µM | >2 µM | >2 µM | >2 µM | >10 µM | >2 µM | >10 µM | >2 µM |
| 27 | >2 µM | >2 µM | >2 µM | >2 µM | >2 µM | >10 µM | >2 µM | >10 µM | >2 µM |
| 28 | >2 µM | 1.41 µM | >2 µM | 0.66 µM | >2 µM | >10 µM | >2 µM | >10 µM | >2 µM |
| 29 | >2 µM | >2 µM | >2 µM | 0.85 µM | >2 µM | >10 µM | >2 µM | >10 µM | >2 µM |
| 30 | >2 µM | >2 µM | >2 µM | >2 µM | >2 µM | >10 µM | >2 µM | >10 µM | >2 µM |
| 31 | >2 µM | 1.33 µM | >2 µM | 0.95 µM | >2 µM | >10 µM | >2 µM | >10 µM | >2 µM |
| 32 | >2 µM | >2 µM | >2 µM | >2 µM | >2 µM | >10 µM | >2 µM | >10 µM | >2 µM |
| 33 | >2 µM | >2 µM | >2 µM | 1.00 µM | >2 µM | >10 µM | >2 µM | >10 µM | >2 µM |
| 34 | >2 µM | >2 µM | >2 µM | 1.27 µM | >2 µM | >10 µM | >2 µM | >10 µM | >2 µM |
| 35 | >2 µM | >2 µM | >2 µM | >2 µM | >2 µM | >10 µM | >2 µM | >10 µM | >2 µM |
| 36 | >2 µM | >2 µM | >2 µM | >2 µM | >2 µM | >10 µM | >2 µM | >10 µM | >2 µM |
| 37 | >2 µM | >2 µM | >2 µM | >2 µM | >2 µM | >10 µM | >2 µM | >10 µM | >2 µM |
| 38 | >2 µM | >2 µM | >2 µM | >2 µM | >2 µM | >10 µM | >2 µM | >10 µM | >2 µM |
| 39 | >2 µM | >2 µM | >2 µM | >2 µM | >2 µM | >10 µM | >2 µM | >10 µM | >2 µM |
| 40 | >2 µM | >2 µM | >2 µM | >2 µM | >2 µM | >10 µM | >2 µM | >10 µM | >2 µM |
| 41 | >2 µM | >2 µM | >2 µM | >2 µM | >2 µM | >10 µM | >2 µM | >10 µM | >2 µM |
| 42 | >2 µM | >2 µM | >2 µM | 1.57 µM | >2 µM | >10 µM | >2 µM | >10 µM | >2 µM |
| 43 | >2 µM | >2 µM | >2 µM | >2 µM | >2 µM | >10 µM | >2 µM | >10 µM | >2 µM |
| 44 | >2 µM | >2 µM | >2 µM | 1.06 µM | >2 µM | >10 µM | >2 µM | >10 µM | >2 µM |
| 45 | >2 µM | >2 µM | >2 µM | >2 µM | >2 µM | >10 µM | >2 µM | >10 µM | >2 µM |
| 46 | >2 µM | >2 µM | >2 µM | 1.16 µM | >2 µM | >10 µM | >2 µM | >10 µM | >2 µM |
| 47 | >2 µM | >2 µM | >2 µM | >2 µM | >2 µM | >10 µM | >2 µM | >10 µM | >2 µM |
| 48 | >2 µM | >2 µM | >2 µM | >2 µM | >2 µM | >10 µM | >2 µM | >10 µM | >2 µM |
| 49 | >2 µM | >2 µM | >2 µM | >2 µM | >2 µM | >10 µM | >2 µM | >10 µM | >2 µM |
| 50 | >2 µM | >2 µM | >2 µM | 1.01 µM | >2 µM | >10 µM | >2 µM | >10 µM | >2 µM |
| 51 | >2 µM | 1.55 µM | >2 µM | 0.54 µM | >2 µM | >10 µM | >2 µM | >10 µM | >2 µM |
| 52 | >2 µM | >2 µM | >2 µM | >2 µM | >2 µM | >10 µM | >2 µM | >10 µM | >2 µM |
| 53 | >2 µM | >2 µM | >2 µM | >2 µM | >2 µM | >10 µM | >2 µM | >10 µM | >2 µM |
| 54 | >2 µM | >2 µM | >2 µM | >2 µM | >2 µM | >10 µM | >2 µM | >10 µM | >2 µM |
| 55 | >2 µM | >2 µM | >2 µM | 1.10 µM | >2 µM | >10 µM | >2 µM | >10 µM | >2 µM |
| 56 | >2 µM | 1.45 µM | >2 µM | 1.38 µM | >2 µM | >10 µM | 1.47 µM | >10 µM | 1.64 µM |
| 57 | >2 µM | >2 µM | >2 µM | 1.34 µM | >2 µM | >10 µM | >2 µM | >10 µM | >2 µM |
| 58 | >2 µM | >2 µM | >2 µM | 0.62 µM | >2 µM | >10 µM | >2 µM | >10 µM | >2 µM |
| 59 | >2 µM | >2 µM | >2 µM | 1.08 µM | >2 µM | >10 µM | >2 µM | >10 µM | >2 µM |
| 60 | >2 µM | >2 µM | >2 µM | 1.88 µM | >2 µM | >10 µM | >2 µM | >10 µM | >2 µM |
| 61 | >2 µM | >2 µM | >2 µM | >2 µM | >2 µM | >10 µM | >2 µM | >10 µM | >2 µM |
| 62 | >2 µM | >2 µM | >2 µM | >2 µM | >2 µM | >10 µM | >2 µM | >10 µM | >2 µM |
| 63 | >2 µM | >2 µM | >2 µM | >2 µM | >2 µM | >10 µM | >2 µM | >10 µM | >2 µM |
| 64 | >2 µM | >2 µM | >2 µM | 1.03 µM | >2 µM | >10 µM | >2 µM | >10 µM | >2 µM |
| 65 | >2 µM | >2 µM | >2 µM | >2 µM | >2 µM | >10 µM | >2 µM | >10 µM | >2 µM |
| 66 | >2 µM | >2 µM | >2 µM | >2 µM | >2 µM | >10 µM | >2 µM | >10 µM | >2 µM |
| 67 | >2 µM | >2 µM | >2 µM | >2 µM | >2 µM | >10 µM | >2 µM | >10 µM | >2 µM |
| 68 | >2 µM | 1.22 µM | >2 µM | 1.23 µM | >2 µM | >10 µM | >2 µM | >10 µM | >2 µM |
| 69 | >2 µM | 1.37 µM | >2 µM | 1.45 µM | >2 µM | >10 µM | >2 µM | >10 µM | >2 µM |
| 70 | >2 µM | >2 µM | >2 µM | 1.21 µM | >2 µM | >10 µM | >2 µM | >10 µM | >2 µM |
| 71 | >2 µM | >2 µM | >2 µM | 1.55 µM | >2 µM | >10 µM | >2 µM | >10 µM | >2 µM |
| 72 | >2 µM | 1.38 µM | >2 µM | 0.85 µM | >2 µM | >2 µM | >2 µM | >2 µM | >2 µM |
| 73 | >2 µM | >2 µM | >2 µM | 1.20 µM | >2 µM | >10 µM | >2 µM | >10 µM | >2 µM |
| 74 | >2 µM | >2 µM | >2 µM | 1.06 µM | >2 µM | >10 µM | >2 µM | >10 µM | >2 µM |
| 75 | >2 µM | 1.16 µM | >2 µM | 1.70 µM | >2 µM | >2 µM | >2 µM | >2 µM | >2 µM |
| 76 | >2 µM | >2 µM | >2 µM | 1.72 µM | >2 µM | >10 µM | >2 µM | >10 µM | >2 µM |
| 77 | >2 µM | >2 µM | >2 µM | 1.44 µM | >2 µM | >10 µM | >2 µM | >10 µM | >2 µM |
| 78 | >2 µM | >2 µM | >2 µM | 1.20 µM | >2 µM | >10 µM | >2 µM | >10 µM | >2 µM |
| 79 | >2 µM | >2 µM | >2 µM | >2 µM | >2 µM | >10 µM | >2 µM | >10 µM | >2 µM |
| 80 | >2 µM | >2 µM | >2 µM | >2 µM | >2 µM | >10 µM | >2 µM | >10 µM | >2 µM |
| 81 | >2 µM | >2 µM | >2 µM | >2 µM | >2 µM | >10 µM | >2 µM | >10 µM | >2 µM |
| 82 | >2 µM | >2 µM | >2 µM | 1.77 µM | >2 µM | >10 µM | >2 µM | >10 µM | >2 µM |
| 83 | >2 µM | 1.95 µM | >2 µM | 1.21 µM | >2 µM | >10 µM | 1.45 µM | >10 µM | 1.76 µM |
| 84 | >2 µM | 1.60 µM | >2 µM | 0.76 µM | >2 µM | >10 µM | 1.12 µM | >10 µM | 1.04 µM |
| 85 | >2 µM | >2 µM | >2 µM | >2 µM | >2 µM | >10 µM | >2 µM | >10 µM | >2 µM |
| 86 | 1.47 µM | 1.58 µM | 1.11 µM | 0.58 µM | >2 µM | >10 µM | 0.50 µM | >10 µM | 0.58 µM |
| 87 | >2 µM | >2 µM | >2 µM | >2 µM | >2 µM | >10 µM | >2 µM | >10 µM | >2 µM |
| 88 | >2 µM | >2 µM | >2 µM | >2 µM | >2 µM | >10 µM | >2 µM | >10 µM | >2 µM |

TABLE 8-continued

| | Breast cancer cell line | | | | | | | | |
|---|---|---|---|---|---|---|---|---|---|
| Compound No. | MCF7 | MDA-MB-231 | MDA-MB-231-L/DOX | SK-BR-3 | BT-20 | HCC1395 | HCC1954 | JIMT-1 | MDA-MB-468 |
| 89 | >2 μM | >2 μM | >2 μM | 1.36 μM | >2 μM | >10 μM | 1.34 μM | >10 μM | 1.36 μM |
| 90 | >2 μM | >2 μM | >2 μM | >2 μM | >2 μM | >10 μM | >2 μM | >10 μM | >2 μM |
| 91 | >2 μM | >2 μM | >2 μM | 1.32 μM | >2 μM | >10 μM | 1.82 μM | >10 μM | 1.32 μM |
| 92 | >2 μM | >2 μM | >2 μM | >2 μM | >2 μM | >10 μM | >2 μM | >10 μM | >2 μM |
| 93 | >2 μM | >2 μM | >2 μM | >2 μM | >2 μM | >10 μM | >2 μM | >10 μM | >2 μM |
| 94 | >2 μM | >2 μM | >2 μM | 1.85 μM | >2 μM | >10 μM | >2 μM | >10 μM | 1.85 μM |
| 95 | 1.29 μM | 1.41 μM | 1.03 μM | 0.47 μM | 1.87 μM | >10 μM | 0.48 μM | >2 μM | 0.47 μM |
| 96 | >2 μM | >2 μM | >2 μM | 0.98 μM | >2 μM | >10 μM | 1.04 μM | >10 μM | 0.98 μM |
| 97 | >2 μM | 1.78 μM | 1.13 μM | 0.76 μM | >2 μM | >10 μM | 0.78 μM | >10 μM | 0.76 μM |
| 98 | >2 μM | 1.86 μM | >2 μM | 1.00 μM | >2 μM | >10 μM | 1.31 μM | >10 μM | 1.00 μM |
| 99 | >2 μM | 1.17 μM | >2 μM | 0.67 μM | >2 μM | >2 μM | 0.78 μM | >10 μM | 0.67 μM |
| 100 | >2 μM | >2 μM | >2 μM | >2 μM | >2 μM | >10 μM | >2 μM | >10 μM | >2 μM |
| 101 | >2 μM | >2 μM | >2 μM | 1.67 μM | >2 μM | >10 μM | 1.22 μM | >10 μM | 1.67 μM |
| 102 | >2 μM | 1.72 μM | >2 μM | 0.85 μM | >2 μM | >10 μM | 1.02 μM | >10 μM | 1.35 μM |
| 103 | >2 μM | >2 μM | >2 μM | 1.74 μM | >2 μM | >10 μM | >2 μM | >10 μM | >2 μM |
| 104 | >2 μM | 1.54 μM | >2 μM | 0.93 μM | >2 μM | >10 μM | 1.05 μM | >10 μM | 1.46 μM |
| 105 | >2 μM | >2 μM | >2 μM | >2 μM | >2 μM | >10 μM | >2 μM | >10 μM | >2 μM |
| 106 | >2 μM | >2 μM | >2 μM | >2 μM | >2 μM | >10 μM | >2 μM | >10 μM | >2 μM |
| 107 | >2 μM | >2 μM | >2 μM | >2 μM | >2 μM | >10 μM | >2 μM | >10 μM | >2 μM |

TABLE 9

| | Blood cancer cell line | | | | | | | |
|---|---|---|---|---|---|---|---|---|
| Compound No. | HL-60 | U-937 | Raji | Ramos (RA 1) | Daudi | Jurkat | MV-4-11 | MOLT-4 |
| 1 | 1.72 μM | >2 μM | >2 μM | >2 μM | >2 μM | >2 μM | 1.39 μM | 1.85 μM |
| 2 | >2 μM | >2 μM | >2 μM | >2 μM | >2 μM | >2 μM | >2 μM | >2 μM |
| 3 | >2 μM | >2 μM | >2 μM | >2 μM | >2 μM | >2 μM | >2 μM | >2 μM |
| 4 | 1.98 μM | 1.24 μM | 1.15 μM | 1.76 μM | >2 μM | 1.07 μM | 1.61 μM | 1.37 μM |
| 5 | >2 μM | >2 μM | >2 μM | >2 μM | >2 μM | >2 μM | >2 μM | >2 μM |
| 6 | 1.65 μM | >2 μM | >2 μM | >2 μM | >2 μM | >2 μM | 1.26 μM | 1.69 μM |
| 7 | >2 μM | >2 μM | >2 μM | >2 μM | >2 μM | >2 μM | >2 μM | >2 μM |
| 8 | >2 μM | >2 μM | >2 μM | >2 μM | >2 μM | >2 μM | >2 μM | >2 μM |
| 9 | 1.20 μM | 1.06 μM | 1.14 μM | 1.55 μM | 1.99 μM | 1.05 μM | 1.09 μM | 1.25 μM |
| 10 | >2 μM | >2 μM | >2 μM | >2 μM | >2 μM | >2 μM | >2 μM | >2 μM |
| 11 | >2 μM | >2 μM | >2 μM | >2 μM | >2 μM | >2 μM | >2 μM | >2 μM |
| 12 | >2 μM | >2 μM | >2 μM | >2 μM | >2 μM | >2 μM | >2 μM | >2 μM |
| 13 | >2 μM | >2 μM | >2 μM | >2 μM | >2 μM | >2 μM | >2 μM | >2 μM |
| 14 | >2 μM | >2 μM | >2 μM | >2 μM | >2 μM | >2 μM | >2 μM | >2 μM |
| 15 | >2 μM | >2 μM | >2 μM | >2 μM | >2 μM | >2 μM | >2 μM | >2 μM |
| 16 | >2 μM | >2 μM | >2 μM | >2 μM | >2 μM | >2 μM | >2 μM | >2 μM |
| 17 | >2 μM | >2 μM | >2 μM | >2 μM | >2 μM | >2 μM | >2 μM | >2 μM |
| 18 | >2 μM | >2 μM | >2 μM | >2 μM | >2 μM | >2 μM | >2 μM | >2 μM |
| 19 | >2 μM | >2 μM | >2 μM | >2 μM | >2 μM | >2 μM | >2 μM | >2 μM |
| 20 | >2 μM | >2 μM | 1.18 μM | 1.51 μM | >2 μM | >2 μM | >2 μM | >2 μM |
| 21 | >2 μM | >2 μM | >2 μM | >2 μM | >2 μM | >2 μM | >2 μM | >2 μM |
| 22 | >2 μM | >2 μM | >2 μM | >2 μM | >2 μM | >2 μM | >2 μM | >2 μM |
| 23 | >2 μM | >2 μM | >2 μM | >2 μM | >2 μM | >2 μM | >2 μM | >2 μM |
| 24 | >2 μM | >2 μM | >2 μM | >2 μM | >2 μM | >2 μM | >2 μM | >2 μM |
| 25 | >2 μM | >2 μM | >2 μM | >2 μM | >2 μM | >2 μM | >2 μM | >2 μM |
| 26 | >2 μM | >2 μM | >2 μM | >2 μM | >2 μM | 1.79 μM | >2 μM | 1.74 μM |
| 27 | >2 μM | >2 μM | >2 μM | >2 μM | >2 μM | >2 μM | >2 μM | >2 μM |
| 28 | 1.06 μM | 0.87 μM | 0.87 μM | 1.49 μM | 1.94 μM | 0.88 μM | 1.07 μM | 1.18 μM |
| 29 | 1.72 μM | 1.05 μM | 1.18 μM | 1.67 μM | >2 μM | 1.08 μM | 1.40 μM | 1.44 μM |
| 30 | >2 μM | >2 μM | >2 μM | >2 μM | >2 μM | >2 μM | >2 μM | >2 μM |
| 31 | 1.93 μM | >2 μM | 1.10 μM | 1.83 μM | 1.65 μM | 0.94 μM | >2 μM | 1.35 μM |
| 32 | >2 μM | >2 μM | >2 μM | >2 μM | >2 μM | >2 μM | >2 μM | >2 μM |
| 33 | 1.77 μM | >2 μM | 0.97 μM | >2 μM | >2 μM | 1.03 μM | 1.28 μM | 1.44 μM |
| 34 | >2 μM | >2 μM | >2 μM | >2 μM | >2 μM | >2 μM | >2 μM | >2 μM |
| 35 | >2 μM | >2 μM | >2 μM | >2 μM | >2 μM | >2 μM | >2 μM | >2 μM |
| 36 | >2 μM | >2 μM | >2 μM | >2 μM | >2 μM | >2 μM | >2 μM | >2 μM |
| 37 | >2 μM | >2 μM | >2 μM | >2 μM | >2 μM | >2 μM | >2 μM | >2 μM |
| 38 | >2 μM | >2 μM | >2 μM | >2 μM | >2 μM | >2 μM | >2 μM | >2 μM |
| 39 | >2 μM | >2 μM | >2 μM | >2 μM | >2 μM | >2 μM | >2 μM | >2 μM |
| 40 | >2 μM | >2 μM | >2 μM | >2 μM | >2 μM | >2 μM | >2 μM | >2 μM |
| 41 | >2 μM | >2 μM | >2 μM | >2 μM | >2 μM | >2 μM | >2 μM | >2 μM |

TABLE 9-continued

| | Blood cancer cell line | | | | | | | |
|---|---|---|---|---|---|---|---|---|
| Compound No. | HL-60 | U-937 | Raji | Ramos (RA 1) | Daudi | Jurkat | MV-4-11 | MOLT-4 |
| 42 | >2 μM | >2 μM | >2 μM | >2 μM | >2 μM | >2 μM | >2 μM | >2 μM |
| 43 | >2 μM | >2 μM | >2 μM | >2 μM | >2 μM | >2 μM | >2 μM | >2 μM |
| 44 | 1.73 μM | >2 μM | 1.16 μM | 1.93 μM | 1.80 μM | 1.13 μM | 1.98 μM | 1.47 μM |
| 45 | >2 μM | >2 μM | >2 μM | >2 μM | >2 μM | >2 μM | >2 μM | >2 μM |
| 46 | >2 μM | >2 μM | >2 μM | >2 μM | >2 μM | >2 μM | >2 μM | >2 μM |
| 47 | >2 μM | >2 μM | >2 μM | >2 μM | >2 μM | >2 μM | >2 μM | >2 μM |
| 48 | >2 μM | >2 μM | >2 μM | >2 μM | >2 μM | >2 μM | >2 μM | >2 μM |
| 49 | >2 μM | >2 μM | >2 μM | >2 μM | >2 μM | >2 μM | >2 μM | >2 μM |
| 50 | >2 μM | >2 μM | 1.41 μM | >2 μM | >2 μM | 1.20 μM | >2 μM | 1.66 μM |
| 51 | 0.95 μM | 0.63 μM | 0.76 μM | 1.07 μM | 1.66 μM | 0.85 μM | 0.68 μM | 1.44 μM |
| 52 | >2 μM | >2 μM | >2 μM | >2 μM | >2 μM | >2 μM | >2 μM | >2 μM |
| 53 | >2 μM | >2 μM | >2 μM | >2 μM | >2 μM | >2 μM | >2 μM | >2 μM |
| 54 | >2 μM | >2 μM | >2 μM | >2 μM | >2 μM | >2 μM | >2 μM | >2 μM |
| 55 | >2 μM | >2 μM | >2 μM | >2 μM | >2 μM | 1.30 μM | >2 μM | 1.47 μM |
| 56 | 1.95 μM | 1.75 μM | 1.12 μM | 1.86 μM | 1.25 μM | 1.06 μM | 1.50 μM | 1.66 μM |
| 57 | >2 μM | >2 μM | >2 μM | >2 μM | >2 μM | >2 μM | >2 μM | >2 μM |
| 58 | 0.87 μM | 0.73 μM | 0.94 μM | 1.25 μM | 1.98 μM | 0.99 μM | 0.97 μM | 1.24 μM |
| 59 | 1.99 μM | >2 μM | 1.15 μM | >2 μM | >2 μM | 1.01 μM | 1.56 μM | 1.38 μM |
| 60 | >2 μM | >2 μM | >2 μM | >2 μM | >2 μM | 1.27 μM | >2 μM | 1.63 μM |
| 61 | >2 μM | >2 μM | >2 μM | >2 μM | >2 μM | >2 μM | >2 μM | >2 μM |
| 62 | >2 μM | >2 μM | >2 μM | >2 μM | >2 μM | >2 μM | >2 μM | >2 μM |
| 63 | >2 μM | >2 μM | >2 μM | >2 μM | >2 μM | >2 μM | >2 μM | >2 μM |
| 64 | 1.50 μM | >2 μM | 1.09 μM | 1.85 μM | >2 μM | 1.07 μM | 1.12 μM | 1.46 μM |
| 65 | >2 μM | >2 μM | >2 μM | >2 μM | >2 μM | >2 μM | >2 μM | >2 μM |
| 66 | >2 μM | >2 μM | >2 μM | >2 μM | >2 μM | >2 μM | >2 μM | >2 μM |
| 67 | >2 μM | >2 μM | >2 μM | >2 μM | >2 μM | >2 μM | >2 μM | >2 μM |
| 68 | 1.71 μM | >2 μM | 1.02 μM | 1.66 μM | 1.21 μM | 1.00 μM | 1.30 μM | 1.07 μM |
| 69 | 1.88 μM | >2 μM | 1.11 μM | 1.87 μM | 1.43 μM | 1.13 μM | 1.47 μM | 1.30 μM |
| 70 | >2 μM | >2 μM | 1.32 μM | 1.90 μM | 1.60 μM | 1.09 μM | 1.52 μM | 1.31 μM |
| 71 | >2 μM | >2 μM | 1.65 μM | >2 μM | >2 μM | 1.25 μM | >2 μM | 1.51 μM |
| 72 | 1.30 μM | 0.97 μM | 0.94 μM | 1.37 μM | 1.60 μM | 0.78 μM | 1.12 μM | 1.05 μM |
| 73 | 1.60 μM | >2 μM | >2 μM | >2 μM | >2 μM | >2 μM | 1.31 μM | >2 μM |
| 74 | 1.98 μM | >2 μM | >2 μM | >2 μM | >2 μM | >2 μM | 1.34 μM | 1.71 μM |
| 75 | >2 μM | >2 μM | 1.16 μM | >2 μM | 1.26 μM | 1.09 μM | >2 μM | 1.28 μM |
| 76 | >2 μM | >2 μM | 1.35 μM | >2 μM | 1.66 μM | 1.20 μM | >2 μM | 1.62 μM |
| 77 | >2 μM | >2 μM | 1.33 μM | >2 μM | 1.42 μM | 1.12 μM | >2 μM | 1.35 μM |
| 78 | >2 μM | >2 μM | >2 μM | 1.98 μM | >2 μM | >2 μM | >2 μM | >2 μM |
| 79 | >2 μM | >2 μM | >2 μM | >2 μM | >2 μM | >2 μM | >2 μM | >2 μM |
| 80 | >2 μM | >2 μM | >2 μM | >2 μM | >2 μM | >2 μM | >2 μM | >2 μM |
| 81 | >2 μM | >2 μM | >2 μM | >2 μM | >2 μM | >2 μM | >2 μM | >2 μM |
| 82 | >2 μM | >2 μM | >2 μM | >2 μM | >2 μM | >2 μM | >2 μM | >2 μM |
| 83 | >2 μM | >2 μM | 1.75 μM | 1.17 μM | 1.22 μM | 1.31 μM | >2 μM | 1.25 μM |
| 84 | 1.48 μM | 1.48 μM | 1.50 μM | 1.00 μM | 1.12 μM | 0.98 μM | 0.82 μM | 0.97 μM |
| 85 | >2 μM | >2 μM | >2 μM | >2 μM | >2 μM | >2 μM | >2 μM | >2 μM |
| 86 | 1.38 μM | 1.23 μM | 0.82 μM | 0.46 μM | 0.65 μM | 0.55 μM | 0.71 μM | 1.01 μM |
| 87 | >2 μM | >2 μM | >2 μM | >2 μM | >2 μM | >2 μM | >2 μM | >2 μM |
| 88 | >2 μM | >2 μM | >2 μM | >2 μM | >2 μM | >2 μM | >2 μM | >2 μM |
| 89 | >2 μM | >2 μM | >2 μM | 1.71 μM | >2 μM | 1.38 μM | 1.75 μM | >2 μM |
| 90 | >2 μM | >2 μM | >2 μM | >2 μM | >2 μM | >2 μM | >2 μM | >2 μM |
| 91 | >2 μM | >2 μM | >2 μM | >2 μM | >2 μM | 1.73 μM | >2 μM | >2 μM |
| 92 | >2 μM | >2 μM | >2 μM | >2 μM | >2 μM | >2 μM | >2 μM | >2 μM |
| 93 | >2 μM | >2 μM | >2 μM | >2 μM | >2 μM | >2 μM | >2 μM | >2 μM |
| 94 | >2 μM | >2 μM | >2 μM | >2 μM | >2 μM | >2 μM | 1.38 μM | >2 μM |
| 95 | 0.98 μM | 1.06 μM | 1.00 μM | 0.52 μM | 0.64 μM | 0.29 μM | 0.70 μM | 1.01 μM |
| 96 | 1.65 μM | >2 μM | 1.66 μM | 1.06 μM | 1.37 μM | 0.59 μM | 1.16 μM | >2 μM |
| 97 | >2 μM | 1.35 μM | 1.29 μM | 0.70 μM | 1.04 μM | 0.51 μM | 0.80 μM | 0.77 μM |
| 98 | >2 μM | >2 μM | >2 μM | 1.23 μM | 1.47 μM | 0.73 μM | 1.24 μM | >2 μM |
| 99 | >2 μM | 1.36 μM | 1.25 μM | 0.84 μM | 1.00 μM | 0.44 μM | 0.95 μM | 0.73 μM |
| 100 | >2 μM | >2 μM | >2 μM | >2 μM | >2 μM | >2 μM | >2 μM | >2 μM |
| 101 | >2 μM | >2 μM | 1.79 μM | 1.48 μM | 1.04 μM | 1.01 μM | >2 μM | 1.16 μM |
| 102 | 1.87 μM | >2 μM | 1.40 μM | 0.98 μM | 1.02 μM | >2 μM | 1.01 μM | 0.94 μM |
| 103 | >2 μM | >2 μM | >2 μM | >2 μM | >2 μM | >2 μM | >2 μM | >2 μM |
| 104 | >2 μM | >2 μM | 1.44 μM | 1.06 μM | 1.15 μM | >2 μM | 0.95 μM | 0.93 μM |
| 105 | >2 μM | >2 μM | >2 μM | >2 μM | >2 μM | >2 μM | >2 μM | >2 μM |
| 106 | >2 μM | >2 μM | >2 μM | >2 μM | >2 μM | >2 μM | >2 μM | >2 μM |
| 107 | >2 μM | >2 μM | >2 μM | >2 μM | >2 μM | >2 μM | >2 μM | >2 μM |

TABLE 10

| Compound No. | Pancreatic cancer cell line | | | | | | |
|---|---|---|---|---|---|---|---|
| | PANC-1 | AsPC-1 | Capan-1 | MIA PaCa-2 | BxPC-3 | CFPAC-1 | Capan-2 |
| 1 | >2 μM | >2 μM | >2 μM | 1.59 μM | >2 μM | >10 μM | >2 μM |
| 2 | >2 μM | >2 μM | >2 μM | >2 μM | >2 μM | >10 μM | >2 μM |
| 3 | >2 μM | >2 μM | >2 μM | >2 μM | >2 μM | >10 μM | >2 μM |
| 4 | >2 μM | >2 μM | >2 μM | 1.34 μM | >2 μM | >10 μM | >2 μM |
| 5 | >2 μM | >2 μM | >2 μM | >2 μM | >2 μM | >10 μM | >2 μM |
| 6 | >2 μM | >2 μM | >2 μM | 1.35 μM | >2 μM | >10 μM | >2 μM |
| 7 | >2 μM | >2 μM | >2 μM | >2 μM | >2 μM | >10 μM | >2 μM |
| 8 | >2 μM | >2 μM | >2 μM | >2 μM | >2 μM | >10 μM | >2 μM |
| 9 | >2 μM | >2 μM | >2 μM | 1.03 μM | >2 μM | >10 μM | >2 μM |
| 10 | >2 μM | >2 μM | >2 μM | >2 μM | >2 μM | >10 μM | >2 μM |
| 11 | >2 μM | >2 μM | >2 μM | >2 μM | >2 μM | >10 μM | >2 μM |
| 12 | >2 μM | >2 μM | >2 μM | >2 μM | >2 μM | >10 μM | >2 μM |
| 13 | >2 μM | >2 μM | >2 μM | >2 μM | >2 μM | >10 μM | >2 μM |
| 14 | >2 μM | >2 μM | >2 μM | >2 μM | >2 μM | >10 μM | >2 μM |
| 15 | >2 μM | >2 μM | >2 μM | 1.63 μM | >2 μM | >10 μM | >2 μM |
| 16 | >2 μM | >2 μM | >2 μM | >2 μM | >2 μM | >10 μM | >2 μM |
| 17 | >2 μM | >2 μM | >2 μM | >2 μM | >2 μM | >10 μM | >2 μM |
| 18 | >2 μM | >2 μM | >2 μM | >2 μM | >2 μM | >10 μM | >2 μM |
| 19 | >2 μM | >2 μM | >2 μM | >2 μM | >2 μM | >10 μM | >2 μM |
| 20 | >2 μM | >2 μM | >2 μM | >2 μM | >2 μM | >10 μM | >2 μM |
| 21 | >2 μM | >2 μM | >2 μM | >2 μM | >2 μM | >10 μM | >2 μM |
| 22 | >2 μM | >2 μM | >2 μM | >2 μM | >2 μM | >10 μM | >2 μM |
| 23 | >2 μM | >2 μM | >2 μM | >2 μM | >2 μM | >10 μM | >2 μM |
| 24 | >2 μM | >2 μM | >2 μM | >2 μM | >2 μM | >10 μM | >2 μM |
| 25 | >2 μM | >2 μM | >2 μM | >2 μM | >2 μM | >10 μM | >2 μM |
| 26 | >2 μM | >2 μM | >2 μM | >2 μM | >2 μM | >10 μM | >2 μM |
| 27 | >2 μM | >2 μM | >2 μM | >2 μM | >2 μM | >10 μM | >2 μM |
| 28 | >2 μM | >2 μM | >2 μM | 0.88 μM | >2 μM | >10 μM | >2 μM |
| 29 | >2 μM | >2 μM | >2 μM | 1.19 μM | >2 μM | >10 μM | >2 μM |
| 30 | >2 μM | >2 μM | >2 μM | >2 μM | >2 μM | >10 μM | >2 μM |
| 31 | >2 μM | >2 μM | >2 μM | 1.18 μM | >2 μM | >10 μM | >2 μM |
| 32 | >2 μM | >2 μM | >2 μM | >2 μM | >2 μM | >10 μM | >2 μM |
| 33 | >2 μM | >2 μM | >2 μM | 1.04 μM | >2 μM | >10 μM | >2 μM |
| 34 | >2 μM | >2 μM | >2 μM | 1.99 μM | >2 μM | >10 μM | >2 μM |
| 35 | >2 μM | >2 μM | >2 μM | >2 μM | >2 μM | >10 μM | >2 μM |
| 36 | >2 μM | >2 μM | >2 μM | >2 μM | >2 μM | >10 μM | >2 μM |
| 37 | >2 μM | >2 μM | >2 μM | >2 μM | >2 μM | >10 μM | >2 μM |
| 38 | >2 μM | >2 μM | >2 μM | >2 μM | >2 μM | >10 μM | >2 μM |
| 39 | >2 μM | >2 μM | >2 μM | >2 μM | >2 μM | >10 μM | >2 μM |
| 40 | >2 μM | >2 μM | >2 μM | >2 μM | >2 μM | >10 μM | >2 μM |
| 41 | >2 μM | >2 μM | >2 μM | >2 μM | >2 μM | >10 μM | >2 μM |
| 42 | >2 μM | >2 μM | >2 μM | >2 μM | >2 μM | >10 μM | >2 μM |
| 43 | >2 μM | >2 μM | >2 μM | >2 μM | >2 μM | >10 μM | >2 μM |
| 44 | >2 μM | >2 μM | >2 μM | 1.23 μM | >2 μM | >10 μM | >2 μM |
| 45 | >2 μM | >2 μM | >2 μM | >2 μM | >2 μM | >10 μM | >2 μM |
| 46 | >2 μM | >2 μM | >2 μM | 1.57 μM | >2 μM | >10 μM | >2 μM |
| 47 | >2 μM | >2 μM | >2 μM | >2 μM | >2 μM | >10 μM | >2 μM |
| 48 | >2 μM | >2 μM | >2 μM | >2 μM | >2 μM | >10 μM | >2 μM |
| 49 | >2 μM | >2 μM | >2 μM | >2 μM | >2 μM | >10 μM | >2 μM |
| 50 | >2 μM | >2 μM | >2 μM | 1.45 μM | >2 μM | >10 μM | >2 μM |
| 51 | >2 μM | >2 μM | >2 μM | 0.76 μM | >2 μM | >10 μM | >2 μM |
| 52 | >2 μM | >2 μM | >2 μM | >2 μM | >2 μM | >10 μM | >2 μM |
| 53 | >2 μM | >2 μM | >2 μM | >2 μM | >2 μM | >10 μM | >2 μM |
| 54 | >2 μM | >2 μM | >2 μM | >2 μM | >2 μM | >10 μM | >2 μM |
| 55 | >2 μM | >2 μM | >2 μM | 1.69 μM | >2 μM | >10 μM | >2 μM |
| 56 | >2 μM | >2 μM | >2 μM | 1.37 μM | >2 μM | >10 μM | >2 μM |
| 57 | >2 μM | >2 μM | >2 μM | >2 μM | >2 μM | >10 μM | >2 μM |
| 58 | >2 μM | >2 μM | >2 μM | 0.81 μM | >2 μM | >10 μM | >2 μM |
| 59 | >2 μM | >2 μM | >2 μM | 1.38 μM | >2 μM | >10 μM | >2 μM |
| 60 | >2 μM | >2 μM | >2 μM | >2 μM | >2 μM | >10 μM | >2 μM |
| 61 | >2 μM | >2 μM | >2 μM | >2 μM | >2 μM | >10 μM | >2 μM |
| 62 | >2 μM | >2 μM | >2 μM | >2 μM | >2 μM | >10 μM | >2 μM |
| 63 | >2 μM | >2 μM | >2 μM | >2 μM | >2 μM | >10 μM | >2 μM |
| 64 | >2 μM | >2 μM | >2 μM | 1.22 μM | >2 μM | >10 μM | >2 μM |
| 65 | >2 μM | >2 μM | >2 μM | >2 μM | >2 μM | >10 μM | >2 μM |
| 66 | >2 μM | >2 μM | >2 μM | >2 μM | >2 μM | >10 μM | >2 μM |
| 67 | >2 μM | >2 μM | >2 μM | >2 μM | >2 μM | >10 μM | >2 μM |
| 68 | >2 μM | >2 μM | >2 μM | 1.12 μM | >2 μM | >10 μM | >2 μM |
| 69 | >2 μM | >2 μM | >2 μM | 1.37 μM | >2 μM | >10 μM | >2 μM |
| 70 | >2 μM | >2 μM | >2 μM | 1.44 μM | >2 μM | >10 μM | >2 μM |
| 71 | >2 μM | >2 μM | >2 μM | 1.65 μM | >2 μM | >10 μM | >2 μM |
| 72 | >2 μM | 2.01 μM | >2 μM | 1.00 μM | >2 μM | >10 μM | >2 μM |
| 73 | >2 μM | >2 μM | >2 μM | 1.65 μM | >2 μM | >10 μM | >2 μM |
| 74 | >2 μM | >2 μM | >2 μM | 1.18 μM | >2 μM | >10 μM | >2 μM |
| 75 | >2 μM | >2 μM | >2 μM | 1.32 μM | >2 μM | >10 μM | >2 μM |

TABLE 10-continued

| Compound No. | Pancreatic cancer cell line | | | | | | |
|---|---|---|---|---|---|---|---|
| | PANC-1 | AsPC-1 | Capan-1 | MIA PaCa-2 | BxPC-3 | CFPAC-1 | Capan-2 |
| 76 | >2 μM | >2 μM | >2 μM | 1.55 μM | >2 μM | >10 μM | >2 μM |
| 77 | >2 μM | >2 μM | >2 μM | 1.39 μM | >2 μM | >10 μM | >2 μM |
| 78 | >2 μM | >2 μM | >2 μM | 1.40 μM | >2 μM | >10 μM | >2 μM |
| 79 | >2 μM | >2 μM | >2 μM | >2 μM | >2 μM | >10 μM | >2 μM |
| 80 | >2 μM | >2 μM | >2 μM | >2 μM | >2 μM | >10 μM | >2 μM |
| 81 | >2 μM | >2 μM | >2 μM | >2 μM | >2 μM | >10 μM | >2 μM |
| 82 | >2 μM | >2 μM | >2 μM | >2 μM | >2 μM | >10 μM | >2 μM |
| 83 | >2 μM | >2 μM | >2 μM | 1.44 μM | >2 μM | >10 μM | >2 μM |
| 84 | >2 μM | 1.80 μM | 1.50 μM | 0.92 μM | >2 μM | >10 μM | >2 μM |
| 85 | >2 μM | >2 μM | >2 μM | >2 μM | >2 μM | >10 μM | >2 μM |
| 86 | >2 μM | 1.28 μM | 1.26 μM | 0.64 μM | >2 μM | >10 μM | >2 μM |
| 87 | >2 μM | >2 μM | >2 μM | >2 μM | >2 μM | >10 μM | >2 μM |
| 88 | >2 μM | >2 μM | >2 μM | >2 μM | >2 μM | >10 μM | >2 μM |
| 89 | >2 μM | >2 μM | >2 μM | 1.41 μM | >2 μM | >10 μM | >2 μM |
| 90 | >2 μM | >2 μM | >2 μM | >2 μM | >2 μM | >10 μM | >2 μM |
| 91 | >2 μM | >2 μM | >2 μM | 1.42 μM | >2 μM | >10 μM | >2 μM |
| 92 | >2 μM | >2 μM | >2 μM | >2 μM | >2 μM | >10 μM | >2 μM |
| 93 | >2 μM | >2 μM | >2 μM | >2 μM | >2 μM | >10 μM | >2 μM |
| 94 | >2 μM | >2 μM | >2 μM | 1.65 μM | >2 μM | >10 μM | >2 μM |
| 95 | >2 μM | 1.06 μM | 1.25 μM | 0.59 μM | >2 μM | >10 μM | >2 μM |
| 96 | >2 μM | >2 μM | >2 μM | 1.14 μM | >2 μM | >10 μM | >2 μM |
| 97 | >2 μM | 1.74 μM | 1.52 μM | 0.86 μM | >2 μM | >10 μM | >2 μM |
| 98 | >2 μM | >2 μM | >2 μM | 1.27 μM | >2 μM | >10 μM | >2 μM |
| 99 | >2 μM | 1.49 μM | 1.99 μM | 0.72 μM | >2 μM | >10 μM | >2 μM |
| 100 | >2 μM | >2 μM | >2 μM | >2 μM | >2 μM | >10 μM | >2 μM |
| 101 | >2 μM | >2 μM | >2 μM | 1.83 μM | >2 μM | >10 μM | >2 μM |
| 102 | >2 μM | 1.54 μM | 1.66 μM | 0.69 μM | >2 μM | >10 μM | >2 μM |
| 103 | >2 μM | >2 μM | >2 μM | >2 μM | >2 μM | >10 μM | >2 μM |
| 104 | >2 μM | >2 μM | 1.59 μM | 0.79 μM | >2 μM | >10 μM | >2 μM |
| 105 | >2 μM | >2 μM | >2 μM | >2 μM | >2 μM | >10 μM | >2 μM |
| 106 | >2 μM | >2 μM | >2 μM | >2 μM | >2 μM | >10 μM | >2 μM |
| 107 | >2 μM | >2 μM | >2 μM | >2 μM | >2 μM | >10 μM | >2 μM |

TABLE 11

| Compound No. | Colorectal cancer cell line | | | | | | | | |
|---|---|---|---|---|---|---|---|---|---|
| | HT-29 | HCT 116 | SW620 | LoVo | HCT-15 | RKO | HCT-8 | DLD-1 | SW480 |
| 1 | >10 μM | 1.67 μM | >2 μM | >2 μM | >2 μM | >2 μM | >2 μM | 0.81 μM | >2 μM |
| 2 | >10 μM | >2 μM | >2 μM | >2 μM | >2 μM | >2 μM | >2 μM | >2 μM | >2 μM |
| 3 | >10 μM | >2 μM | >2 μM | >2 μM | >2 μM | >2 μM | >2 μM | >2 μM | >2 μM |
| 4 | >10 μM | 1.15 μM | 1.33 μM | 1.80 μM | 1.33 μM | 1.55 μM | 1.58 μM | 1.84 μM | >2 μM |
| 5 | >10 μM | >2 μM | >2 μM | >2 μM | >2 μM | >2 μM | >2 μM | >2 μM | >2 μM |
| 6 | >10 μM | 1.48 μM | 1.55 μM | >2 μM | 1.70 μM | 1.84 μM | >2 μM | 0.70 μM | >2 μM |
| 7 | >10 μM | >2 μM | >2 μM | >2 μM | >2 μM | >2 μM | >2 μM | >2 μM | >2 μM |
| 8 | >10 μM | >2 μM | >2 μM | >2 μM | >2 μM | >2 μM | >2 μM | >2 μM | >2 μM |
| 9 | >10 μM | 1.05 μM | 1.36 μM | >2 μM | 1.24 μM | 1.93 μM | 1.75 μM | 0.87 μM | 1.28 μM |
| 10 | >10 μM | >2 μM | >2 μM | >2 μM | >2 μM | >2 μM | >2 μM | >2 μM | >2 μM |
| 11 | >10 μM | >2 μM | >2 μM | >2 μM | >2 μM | >2 μM | >2 μM | 0.82 μM | >2 μM |
| 12 | >10 μM | >2 μM | >2 μM | >2 μM | >2 μM | >2 μM | >2 μM | >2 μM | >2 μM |
| 13 | >10 μM | >2 μM | >2 μM | >2 μM | >2 μM | >2 μM | >2 μM | >2 μM | >2 μM |
| 14 | >10 μM | >2 μM | >2 μM | >2 μM | >2 μM | >2 μM | >2 μM | >2 μM | >2 μM |
| 15 | >10 μM | >2 μM | >2 μM | >2 μM | >2 μM | >2 μM | >2 μM | >2 μM | >2 μM |
| 16 | >10 μM | >2 μM | >2 μM | >2 μM | >2 μM | >2 μM | >2 μM | >2 μM | >2 μM |
| 17 | >10 μM | >2 μM | >2 μM | >2 μM | >2 μM | >2 μM | >2 μM | >2 μM | >2 μM |
| 18 | >10 μM | >2 μM | >2 μM | >2 μM | >2 μM | >2 μM | >2 μM | >2 μM | >2 μM |
| 19 | >10 μM | >2 μM | >2 μM | >2 μM | >2 μM | >2 μM | >2 μM | >2 μM | >2 μM |
| 20 | >10 μM | >2 μM | >2 μM | >2 μM | >2 μM | >2 μM | >2 μM | >2 μM | >2 μM |
| 21 | >10 μM | >2 μM | >2 μM | >2 μM | >2 μM | >2 μM | >2 μM | >2 μM | >2 μM |
| 22 | >10 μM | >2 μM | >2 μM | >2 μM | >2 μM | >2 μM | >2 μM | >2 μM | >2 μM |
| 23 | >10 μM | >2 μM | >2 μM | >2 μM | >2 μM | >2 μM | >2 μM | >2 μM | >2 μM |
| 24 | >10 μM | >2 μM | >2 μM | >2 μM | >2 μM | >2 μM | >2 μM | >2 μM | >2 μM |
| 25 | >10 μM | >2 μM | >2 μM | >2 μM | >2 μM | >2 μM | >2 μM | >2 μM | >2 μM |
| 26 | >10 μM | >2 μM | >2 μM | >2 μM | >2 μM | >2 μM | 1.79 μM | >2 μM | >2 μM |
| 27 | >10 μM | >2 μM | >2 μM | >2 μM | >2 μM | >2 μM | >2 μM | >2 μM | >2 μM |
| 28 | >10 μM | 0.96 μM | 1.09 μM | 1.90 μM | 1.06 μM | 1.09 μM | 1.30 μM | 0.94 μM | 1.22 μM |
| 29 | >10 μM | 1.21 μM | 1.38 μM | >2 μM | 1.40 μM | 1.57 μM | 1.71 μM | 0.87 μM | >2 μM |
| 30 | >10 μM | >2 μM | >2 μM | >2 μM | >2 μM | >2 μM | >2 μM | >2 μM | >2 μM |
| 31 | >10 μM | 1.18 μM | 1.35 μM | >2 μM | 1.25 μM | 1.42 μM | 1.42 μM | 0.82 μM | 1.66 μM |
| 32 | >10 μM | >2 μM | >2 μM | >2 μM | >2 μM | >2 μM | >2 μM | >2 μM | >2 μM |
| 33 | >10 μM | 1.33 μM | 1.51 μM | >2 μM | 1.53 μM | 1.50 μM | 1.65 μM | 0.94 μM | >2 μM |

TABLE 11-continued

| Compound No. | Colorectal cancer cell line | | | | | | | | |
|---|---|---|---|---|---|---|---|---|---|
| | HT-29 | HCT 116 | SW620 | LoVo | HCT-15 | RKO | HCT-8 | DLD-1 | SW480 |
| 34 | >10 μM | 1.84 μM | 1.87 μM | >2 μM | 1.95 μM | >2 μM | >2 μM | 1.32 μM | >2 μM |
| 35 | >10 μM | >2 μM | >2 μM | >2 μM | >2 μM | >2 μM | >2 μM | >2 μM | >2 μM |
| 36 | >10 μM | >2 μM | >2 μM | >2 μM | >2 μM | >2 μM | >2 μM | >2 μM | >2 μM |
| 37 | >10 μM | >2 μM | >2 μM | >2 μM | >2 μM | >2 μM | >2 μM | >2 μM | >2 μM |
| 38 | >10 μM | >2 μM | >2 μM | >2 μM | >2 μM | >2 μM | >2 μM | >2 μM | >2 μM |
| 39 | >10 μM | >2 μM | >2 μM | >2 μM | >2 μM | >2 μM | >2 μM | >2 μM | >2 μM |
| 40 | >10 μM | >2 μM | >2 μM | >2 μM | >2 μM | >2 μM | >2 μM | >2 μM | >2 μM |
| 41 | >10 μM | >2 μM | >2 μM | >2 μM | >2 μM | >2 μM | >2 μM | >2 μM | >2 μM |
| 42 | >10 μM | >2 μM | >2 μM | >2 μM | >2 μM | >2 μM | >2 μM | 1.96 μM | >2 μM |
| 43 | >10 μM | >2 μM | >2 μM | >2 μM | >2 μM | >2 μM | >2 μM | >2 μM | >2 μM |
| 44 | >10 μM | 1.20 μM | 1.45 μM | >2 μM | 1.48 μM | 1.15 μM | 1.66 μM | 0.89 μM | 1.34 μM |
| 45 | >10 μM | >2 μM | >2 μM | >2 μM | >2 μM | >2 μM | >2 μM | >2 μM | >2 μM |
| 46 | >10 μM | 1.82 μM | 1.75 μM | >2 μM | 1.94 μM | 1.83 μM | >2 μM | 1.26 μM | >2 μM |
| 47 | >10 μM | >2 μM | >2 μM | >2 μM | >2 μM | >2 μM | >2 μM | >2 μM | >2 μM |
| 48 | >10 μM | >2 μM | >2 μM | >2 μM | >2 μM | >2 μM | >2 μM | 1.60 μM | >2 μM |
| 49 | >10 μM | >2 μM | >2 μM | >2 μM | >2 μM | >2 μM | >2 μM | >2 μM | >2 μM |
| 50 | >10 μM | 1.39 μM | 1.58 μM | >2 μM | 1.59 μM | 1.77 μM | 1.99 μM | 0.99 μM | >2 μM |
| 51 | >10 μM | 0.84 μM | 1.00 μM | 1.64 μM | 1.01 μM | 1.10 μM | 1.21 μM | 0.66 μM | 0.95 μM |
| 52 | >10 μM | >2 μM | >2 μM | >2 μM | >2 μM | >2 μM | >2 μM | >2 μM | >2 μM |
| 53 | >10 μM | >2 μM | >2 μM | >2 μM | >2 μM | >2 μM | >2 μM | >2 μM | >2 μM |
| 54 | >10 μM | >2 μM | >2 μM | >2 μM | >2 μM | >2 μM | >2 μM | >2 μM | >2 μM |
| 55 | >10 μM | 1.81 μM | 1.91 μM | >2 μM | 1.81 μM | >2 μM | >2 μM | 1.15 μM | >2 μM |
| 56 | >10 μM | 1.19 μM | 1.91 μM | >2 μM | 1.32 μM | 1.53 μM | 1.69 μM | 0.80 μM | >2 μM |
| 57 | >10 μM | >2 μM | >2 μM | >2 μM | >2 μM | >2 μM | >2 μM | >2 μM | >2 μM |
| 58 | >10 μM | 1.09 μM | 1.16 μM | 2.02 μM | 1.10 μM | 1.12 μM | 1.35 μM | 0.77 μM | 1.22 μM |
| 59 | >10 μM | 1.11 μM | 1.35 μM | >2 μM | 1.27 μM | 1.56 μM | 1.50 μM | 0.89 μM | >2 μM |
| 60 | >10 μM | 1.94 μM | >2 μM | >2 μM | 1.80 μM | >2 μM | >2 μM | 1.48 μM | >2 μM |
| 61 | >10 μM | >2 μM | >2 μM | >2 μM | >2 μM | >2 μM | >2 μM | >2 μM | >2 μM |
| 62 | >10 μM | >2 μM | >2 μM | >2 μM | >2 μM | >2 μM | >2 μM | >2 μM | >2 μM |
| 63 | >10 μM | >2 μM | >2 μM | >2 μM | >2 μM | >2 μM | >2 μM | >2 μM | >2 μM |
| 64 | >10 μM | 1.37 μM | 1.65 μM | >2 μM | 1.36 μM | 1.69 μM | 1.63 μM | 0.95 μM | >2 μM |
| 65 | >10 μM | >2 μM | >2 μM | >2 μM | >2 μM | >2 μM | >2 μM | >2 μM | >2 μM |
| 66 | >10 μM | >2 μM | >2 μM | >2 μM | >2 μM | >2 μM | >2 μM | >2 μM | >2 μM |
| 67 | >10 μM | >2 μM | >2 μM | >2 μM | >2 μM | >2 μM | >2 μM | >2 μM | >2 μM |
| 68 | >2 μM | 1.09 μM | 1.66 μM | >2 μM | 0.98 μM | 1.33 μM | 1.30 μM | 0.78 μM | 1.75 μM |
| 69 | >10 μM | 1.52 μM | 1.77 μM | >2 μM | 1.42 μM | 1.54 μM | 1.91 μM | 0.92 μM | >2 μM |
| 70 | >10 μM | 1.32 μM | 1.71 μM | >2 μM | 1.19 μM | 1.63 μM | 1.54 μM | 0.92 μM | >2 μM |
| 71 | >10 μM | 1.73 μM | >2 μM | >2 μM | 1.62 μM | >2 μM | >2 μM | 1.15 μM | >2 μM |
| 72 | >2 μM | 0.94 μM | 1.24 μM | 1.92 μM | 0.99 μM | 1.35 μM | 1.24 μM | 0.74 μM | 1.41 μM |
| 73 | >10 μM | 1.86 μM | >2 μM | >2 μM | >2 μM | >2 μM | >2 μM | 1.33 μM | >2 μM |
| 74 | >10 μM | 1.61 μM | 1.77 μM | >2 μM | 1.53 μM | >2 μM | 2.01 μM | 1.02 μM | >2 μM |
| 75 | >10 μM | 1.25 μM | 1.76 μM | >2 μM | 1.39 μM | 1.32 μM | 1.78 μM | 0.88 μM | 1.66 μM |
| 76 | >10 μM | 1.57 μM | >2 μM | >2 μM | 1.64 μM | 1.52 μM | >2 μM | 1.09 μM | >2 μM |
| 77 | >10 μM | 1.45 μM | 1.68 μM | >2 μM | 1.24 μM | 1.29 μM | 1.70 μM | 0.92 μM | 1.80 μM |
| 78 | >10 μM | 1.93 μM | 1.76 μM | >2 μM | 1.59 μM | 1.50 μM | >2 μM | 1.28 μM | >2 μM |
| 79 | >10 μM | >2 μM | >2 μM | >2 μM | >2 μM | >2 μM | >2 μM | >2 μM | >2 μM |
| 80 | >10 μM | >2 μM | >2 μM | >2 μM | >2 μM | >2 μM | >2 μM | >2 μM | >2 μM |
| 81 | >10 μM | >2 μM | >2 μM | >2 μM | >2 μM | >2 μM | >2 μM | >2 μM | >2 μM |
| 82 | >10 μM | >2 μM | >2 μM | >2 μM | >2 μM | >2 μM | >2 μM | >2 μM | >2 μM |
| 83 | >10 μM | 1.80 μM | >2 μM | >2 μM | 1.62 μM | 1.03 μM | 1.88 μM | 1.38 μM | >2 μM |
| 84 | >10 μM | 1.16 μM | 1.23 μM | 1.96 μM | 1.51 μM | 1.27 μM | 1.30 μM | 0.93 μM | 1.55 μM |
| 85 | >10 μM | >2 μM | >2 μM | >2 μM | >2 μM | >2 μM | >2 μM | >2 μM | >2 μM |
| 86 | >10 μM | 0.86 μM | 0.74 μM | 1.15 μM | 1.26 μM | 0.89 μM | 1.11 μM | 1.09 μM | 1.27 μM |
| 87 | >10 μM | >2 μM | >2 μM | >2 μM | >2 μM | >2 μM | >2 μM | >2 μM | >2 μM |
| 88 | >10 μM | >2 μM | >2 μM | >2 μM | >2 μM | >2 μM | >2 μM | >2 μM | >2 μM |
| 89 | >10 μM | 1.59 μM | 1.70 μM | >2 μM | >2 μM | 1.72 μM | >2 μM | 1.64 μM | >2 μM |
| 90 | >10 μM | >2 μM | >2 μM | >2 μM | >2 μM | >2 μM | >2 μM | >2 μM | >2 μM |
| 91 | >10 μM | >2 μM | >2 μM | >2 μM | >2 μM | 1.41 μM | >2 μM | 1.82 μM | >2 μM |
| 92 | >10 μM | >2 μM | >2 μM | >2 μM | >2 μM | >2 μM | >2 μM | >2 μM | >2 μM |
| 93 | >10 μM | >2 μM | >2 μM | >2 μM | >2 μM | >2 μM | >2 μM | >2 μM | >2 μM |
| 94 | >10 μM | >2 μM | >2 μM | >2 μM | >2 μM | >2 μM | >2 μM | >2 μM | >2 μM |
| 95 | >10 μM | 0.76 μM | 0.64 μM | 0.91 μM | 1.06 μM | 0.92 μM | 0.81 μM | 1.13 μM | 1.19 μM |
| 96 | >10 μM | 1.53 μM | 1.66 μM | >2 μM | 1.87 μM | 1.58 μM | >2 μM | 1.82 μM | >2 μM |
| 97 | >10 μM | 1.25 μM | 1.10 μM | 1.52 μM | 1.42 μM | 1.27 μM | 1.35 μM | 1.36 μM | 1.69 μM |
| 98 | >10 μM | 1.48 μM | 1.76 μM | >2 μM | 1.73 μM | 1.34 μM | 1.66 μM | 1.52 μM | >2 μM |
| 99 | >10 μM | 0.82 μM | 0.92 μM | 1.45 μM | 0.97 μM | 0.95 μM | 0.98 μM | 0.87 μM | 1.30 μM |
| 100 | >10 μM | >2 μM | >2 μM | >2 μM | >2 μM | >2 μM | >2 μM | >2 μM | >2 μM |
| 101 | >10 μM | 1.74 μM | >2 μM | >2 μM | >2 μM | 1.91 μM | 1.61 μM | >2 μM | >2 μM |
| 102 | >10 μM | 1.22 μM | 1.22 μM | 1.94 μM | 1.33 μM | 1.19 μM | 1.24 μM | 1.16 μM | 1.60 μM |
| 103 | >10 μM | >2 μM | >2 μM | >2 μM | >2 μM | >2 μM | >2 μM | >2 μM | >2 μM |
| 104 | >10 μM | 1.32 μM | 1.36 μM | >2 μM | 1.49 μM | 1.15 μM | 1.29 μM | 1.24 μM | 1.58 μM |
| 105 | >10 μM | >2 μM | >2 μM | >2 μM | >2 μM | >2 μM | >2 μM | >2 μM | >2 μM |
| 106 | >10 μM | >2 μM | >2 μM | >2 μM | >2 μM | >2 μM | >2 μM | >2 μM | >2 μM |
| 107 | >10 μM | >2 μM | >2 μM | >2 μM | >2 μM | >2 μM | >2 μM | >2 μM | >2 μM |

TABLE 12

| Compound No. | Brain cancer cell line | | | Neuroblastoma | Melanoma | Liver cancer cell line |
|---|---|---|---|---|---|---|
| | U-251 MG | T98G | U-138 MG | SH-SY5Y | LOX-IMVI | SK-HEP-1 |
| 1 | >2 μM | >10 μM | >2 μM | >2 μM | 1.50 μM | 1.23 μM |
| 2 | >2 μM | >10 μM | >10 μM | >2 μM | >2 μM | >2 μM |
| 3 | >2 μM | >10 μM | >10 μM | >2 μM | >2 μM | >2 μM |
| 4 | 1.22 μM | >10 μM | 1.81 μM | >2 μM | 1.09 μM | 1.13 μM |
| 5 | >2 μM | >10 μM | >10 μM | >2 μM | >2 μM | >2 μM |
| 6 | >2 μM | >10 μM | >2 μM | >2 μM | 1.35 μM | 1.38 μM |
| 7 | >2 μM | >10 μM | >10 μM | >2 μM | >2 μM | >2 μM |
| 8 | >2 μM | >10 μM | >10 μM | >2 μM | >2 μM | >2 μM |
| 9 | >2 μM | >10 μM | 1.26 μM | >2 μM | 1.05 μM | 0.99 μM |
| 10 | >2 μM | >10 μM | >10 μM | >2 μM | >2 μM | >2 μM |
| 11 | >2 μM | >10 μM | >2 μM | >2 μM | >2 μM | >2 μM |
| 12 | >2 μM | >10 μM | >10 μM | >2 μM | >2 μM | >2 μM |
| 13 | >2 μM | >10 μM | >10 μM | >2 μM | >2 μM | >2 μM |
| 14 | >2 μM | >10 μM | >10 μM | >2 μM | >2 μM | >2 μM |
| 15 | >2 μM | >10 μM | >2 μM | >2 μM | >2 μM | >2 μM |
| 16 | >2 μM | >10 μM | >10 μM | >2 μM | >2 μM | >2 μM |
| 17 | >2 μM | >10 μM | >10 μM | >2 μM | >2 μM | >2 μM |
| 18 | >2 μM | >10 μM | >10 μM | >2 μM | >2 μM | >2 μM |
| 19 | >2 μM | >10 μM | >10 μM | >2 μM | >2 μM | >2 μM |
| 20 | >2 μM | >10 μM | >10 μM | >2 μM | >2 μM | >2 μM |
| 21 | >2 μM | >10 μM | >10 μM | >2 μM | >2 μM | >2 μM |
| 22 | >2 μM | >10 μM | >10 μM | >2 μM | >2 μM | >2 μM |
| 23 | >2 μM | >10 μM | >10 μM | >2 μM | >2 μM | >2 μM |
| 24 | >2 μM | >10 μM | >10 μM | >2 μM | >2 μM | >2 μM |
| 25 | >2 μM | >10 μM | >10 μM | >2 μM | >2 μM | >2 μM |
| 26 | >2 μM | >2 μM | >2 μM | >2 μM | >2 μM | >2 μM |
| 27 | >2 μM | >10 μM | >10 μM | >2 μM | >2 μM | >2 μM |
| 28 | 0.88 μM | >10 μM | 1.26 μM | >2 μM | 0.88 μM | 0.76 μM |
| 29 | 1.14 μM | >10 μM | 1.38 μM | >2 μM | 1.24 μM | 1.03 μM |
| 30 | >2 μM | >10 μM | >10 μM | >2 μM | >2 μM | >2 μM |
| 31 | 1.09 μM | >10 μM | 1.79 μM | >2 μM | 1.11 μM | 0.89 μM |
| 32 | >2 μM | >10 μM | >10 μM | >2 μM | >2 μM | >2 μM |
| 33 | 1.11 μM | >10 μM | >2 μM | >2 μM | 1.13 μM | 1.08 μM |
| 34 | >2 μM | >10 μM | >2 μM | >2 μM | 1.63 μM | 1.72 μM |
| 35 | >2 μM | >10 μM | >10 μM | >2 μM | >2 μM | >2 μM |
| 36 | >2 μM | >10 μM | >2 μM | >2 μM | >2 μM | >2 μM |
| 37 | >2 μM | >10 μM | >10 μM | >2 μM | >2 μM | >2 μM |
| 38 | >2 μM | >10 μM | >10 μM | >2 μM | >2 μM | >2 μM |
| 39 | >2 μM | >10 μM | >10 μM | >2 μM | >2 μM | >2 μM |
| 40 | >2 μM | >10 μM | >10 μM | >2 μM | >2 μM | >2 μM |
| 41 | >2 μM | >10 μM | >10 μM | >2 μM | >2 μM | >2 μM |
| 42 | >2 μM | >10 μM | >2 μM | >2 μM | >2 μM | >2 μM |
| 43 | >2 μM | >10 μM | >10 μM | >2 μM | >2 μM | >2 μM |
| 44 | 1.05 μM | >10 μM | >2 μM | >2 μM | 1.64 μM | 0.94 μM |
| 45 | >2 μM | >10 μM | >10 μM | >2 μM | >2 μM | >2 μM |
| 46 | >2 μM | >10 μM | >2 μM | >2 μM | 1.57 μM | 1.31 μM |
| 47 | >2 μM | >10 μM | >10 μM | >2 μM | >2 μM | >2 μM |
| 48 | >2 μM | >10 μM | >2 μM | >2 μM | >2 μM | >2 μM |
| 49 | >2 μM | >10 μM | >10 μM | >2 μM | >2 μM | >2 μM |
| 50 | 1.28 μM | >10 μM | >2 μM | >2 μM | 1.51 μM | 1.35 μM |
| 51 | >2 μM | >10 μM | 1.92 μM | >2 μM | 1.46 μM | 1.31 μM |
| 52 | >2 μM | >10 μM | >10 μM | >2 μM | >2 μM | >2 μM |
| 53 | >2 μM | >10 μM | >10 μM | >2 μM | >2 μM | >2 μM |
| 54 | >2 μM | >10 μM | >10 μM | >2 μM | >2 μM | >2 μM |
| 55 | >2 μM | >10 μM | >2 μM | >2 μM | 1.62 μM | 1.43 μM |
| 56 | 1.17 μM | >10 μM | 1.34 μM | >2 μM | 1.09 μM | 1.02 μM |
| 57 | >2 μM | >10 μM | >10 μM | >2 μM | >2 μM | >2 μM |
| 58 | 0.84 μM | >10 μM | 1.46 μM | >2 μM | 0.88 μM | 0.78 μM |
| 59 | 1.28 μM | >10 μM | 1.50 μM | >2 μM | 1.06 μM | 0.91 μM |
| 60 | >2 μM | >10 μM | >2 μM | >2 μM | 1.67 μM | >2 μM |
| 61 | >2 μM | >10 μM | >10 μM | >2 μM | >2 μM | >2 μM |
| 62 | >2 μM | >10 μM | >10 μM | >2 μM | >2 μM | >2 μM |
| 63 | >2 μM | >10 μM | >2 μM | >2 μM | >2 μM | >2 μM |
| 64 | >2 μM | >10 μM | 1.43 μM | >2 μM | 1.05 μM | 0.87 μM |
| 65 | >2 μM | >10 μM | >10 μM | >2 μM | >2 μM | >2 μM |
| 66 | >2 μM | >10 μM | >10 μM | >2 μM | >2 μM | >2 μM |
| 67 | >2 μM | >10 μM | >10 μM | >2 μM | >2 μM | >2 μM |
| 68 | 0.93 μM | >2 μM | 1.14 μM | >2 μM | 0.96 μM | 0.86 μM |
| 69 | 1.16 μM | >10 μM | 1.54 μM | >2 μM | 1.12 μM | 1.04 μM |
| 70 | 1.14 μM | >10 μM | 1.52 μM | >2 μM | 1.19 μM | 1.03 μM |
| 71 | >2 μM | >10 μM | >2 μM | >2 μM | 1.41 μM | 1.18 μM |
| 72 | 1.07 μM | >10 μM | 1.18 μM | >2 μM | 0.92 μM | 0.73 μM |
| 73 | >2 μM | >10 μM | >2 μM | >2 μM | 1.67 μM | 1.42 μM |
| 74 | >2 μM | >10 μM | 1.44 μM | >2 μM | 1.26 μM | 0.88 μM |
| 75 | 1.09 μM | >10 μM | 1.37 μM | >2 μM | 1.04 μM | 1.03 μM |

TABLE 12-continued

| Compound No. | Brain cancer cell line | | | Neuroblastoma | Melanoma | Liver cancer cell line |
| --- | --- | --- | --- | --- | --- | --- |
| | U-251 MG | T98G | U-138 MG | SH-SY5Y | LOX-IMVI | SK-HEP-1 |
| 76 | >2 μM | >10 μM | >2 μM | >2 μM | 1.37 μM | 1.23 μM |
| 77 | 1.29 μM | >2 μM | 1.55 μM | >2 μM | 1.16 μM | 1.09 μM |
| 78 | >2 μM | >10 μM | >2 μM | >2 μM | 1.37 μM | 1.29 μM |
| 79 | >2 μM | >10 μM | >10 μM | >2 μM | >2 μM | >2 μM |
| 80 | >2 μM | >10 μM | >10 μM | >2 μM | >2 μM | >2 μM |
| 81 | >2 μM | >10 μM | >2 μM | >2 μM | >2 μM | >2 μM |
| 82 | >2 μM | >10 μM | >2 μM | 1.55 μM | >2 μM | >2 μM |
| 83 | 1.35 μM | >2 μM | >2 μM | 1.24 μM | 1.57 μM | 1.51 μM |
| 84 | >2 μM | >10 μM | >2 μM | 0.60 μM | 1.45 μM | 1.07 μM |
| 85 | >2 μM | >10 μM | >10 μM | >2 μM | >2 μM | >2 μM |
| 86 | 0.74 μM | >10 μM | 1.29 μM | 0.50 μM | 0.71 μM | 1.00 μM |
| 87 | >2 μM | >10 μM | >10 μM | >2 μM | >2 μM | >2 μM |
| 88 | >2 μM | >10 μM | >10 μM | 1.51 μM | >2 μM | >2 μM |
| 89 | >2 μM | >10 μM | >2 μM | 1.04 μM | 1.65 μM | 1.59 μM |
| 90 | >2 μM | >10 μM | >10 μM | >2 μM | >2 μM | >2 μM |
| 91 | >2 μM | >10 μM | >2 μM | 1.22 μM | >2 μM | 1.72 μM |
| 92 | >2 μM | >10 μM | >10 μM | >2 μM | >2 μM | >2 μM |
| 93 | >2 μM | >10 μM | >10 μM | >2 μM | >2 μM | >2 μM |
| 94 | >2 μM | >10 μM | >2 μM | 1.76 μM | >2 μM | >2 μM |
| 95 | 0.61 μM | >10 μM | 1.01 μM | 0.48 μM | 0.54 μM | 0.94 μM |
| 96 | 1.31 μM | >10 μM | >2 μM | 0.77 μM | >2 μM | 1.96 μM |
| 97 | 1.12 μM | >10 μM | 1.69 μM | 0.60 μM | 1.03 μM | 1.07 μM |
| 98 | 1.25 μM | >10 μM | >2 μM | 0.83 μM | 1.34 μM | 1.20 μM |
| 99 | 0.79 μM | >10 μM | 1.16 μM | 0.45 μM | 0.87 μM | 1.06 μM |
| 100 | >2 μM | >10 μM | >10 μM | >2 μM | >2 μM | >2 μM |
| 101 | >2 μM | >10 μM | >2 μM | 1.40 μM | >2 μM | >2 μM |
| 102 | >2 μM | >10 μM | 1.24 μM | 0.52 μM | 0.86 μM | >2 μM |
| 103 | >2 μM | >10 μM | >2 μM | 1.01 μM | >2 μM | >2 μM |
| 104 | >2 μM | >10 μM | 1.47 μM | 0.60 μM | 0.88 μM | 1.50 μM |
| 105 | >2 μM | >10 μM | >10 μM | >2 μM | >2 μM | >2 μM |
| 106 | >2 μM | >10 μM | >10 μM | 1.29 μM | >2 μM | >2 μM |
| 107 | >2 μM | >10 μM | >10 μM | >2 μM | >2 μM | >2 μM |

TABLE 13

| Compound No. | Cervical carcinoma HeLa | Ovarian cancer OVCAR-3 | Renal cancer ACHN | Papilloma RT4 |
| --- | --- | --- | --- | --- |
| 1 | >10 μM | 0.70 μM | >2 μM | >10 μM |
| 2 | >10 μM | >2 μM | >2 μM | >10 μM |
| 3 | >10 μM | >2 μM | >2 μM | >10 μM |
| 4 | >10 μM | 0.81 μM | >2 μM | >10 μM |
| 5 | >10 μM | >2 μM | >2 μM | >10 μM |
| 6 | >10 μM | 0.73 μM | >2 μM | >10 μM |
| 7 | >10 μM | >2 μM | >2 μM | >10 μM |
| 8 | >10 μM | >2 μM | >2 μM | >10 μM |
| 9 | >10 μM | 0.58 μM | >2 μM | >10 μM |
| 10 | >10 μM | >2 μM | >2 μM | >10 μM |
| 11 | >10 μM | >2 μM | >2 μM | >10 μM |
| 12 | >10 μM | >2 μM | >2 μM | >10 μM |
| 13 | >10 μM | >2 μM | >2 μM | >10 μM |
| 14 | >10 μM | >2 μM | >2 μM | >10 μM |
| 15 | >10 μM | >2 μM | >2 μM | >10 μM |
| 16 | >10 μM | >2 μM | >2 μM | >10 μM |
| 17 | >10 μM | >2 μM | >2 μM | >10 μM |
| 18 | >10 μM | >2 μM | >2 μM | >10 μM |
| 19 | >10 μM | >2 μM | >2 μM | >10 μM |
| 20 | >10 μM | >2 μM | >2 μM | >10 μM |
| 21 | >10 μM | >2 μM | >2 μM | >10 μM |
| 22 | >10 μM | >2 μM | >2 μM | >10 μM |
| 23 | >10 μM | >2 μM | >2 μM | >10 μM |
| 24 | >10 μM | >2 μM | >2 μM | >10 μM |
| 25 | >10 μM | >2 μM | >2 μM | >10 μM |
| 26 | >10 μM | >2 μM | >2 μM | >10 μM |
| 27 | >10 μM | >2 μM | >2 μM | >10 μM |
| 28 | >10 μM | 0.69 μM | >2 μM | >10 μM |
| 29 | >10 μM | 0.80 μM | >2 μM | >10 μM |
| 30 | >10 μM | >2 μM | >2 μM | >10 μM |
| 31 | >10 μM | 0.71 μM | >2 μM | >10 μM |
| 32 | >10 μM | >2 μM | >2 μM | >10 μM |
| 33 | >10 μM | 1.18 μM | >2 μM | >10 μM |
| 34 | >10 μM | 0.99 μM | >2 μM | >10 μM |
| 35 | >10 μM | >2 μM | >2 μM | >10 μM |
| 36 | >10 μM | >2 μM | >2 μM | >10 μM |
| 37 | >10 μM | >2 μM | >2 μM | >10 μM |
| 38 | >10 μM | >2 μM | >2 μM | >10 μM |
| 39 | >10 μM | >2 μM | >2 μM | >10 μM |
| 40 | >10 μM | >2 μM | >2 μM | >10 μM |
| 41 | >10 μM | >2 μM | >2 μM | >10 μM |
| 42 | >10 μM | >2 μM | >2 μM | >10 μM |
| 43 | >10 μM | >2 μM | >2 μM | >10 μM |
| 44 | >10 μM | 0.84 μM | >2 μM | >10 μM |
| 45 | >10 μM | >2 μM | >2 μM | >10 μM |
| 46 | >10 μM | 1.02 μM | >2 μM | >10 μM |
| 47 | >10 μM | >2 μM | >2 μM | >10 μM |
| 48 | >10 μM | >2 μM | >2 μM | >10 μM |
| 49 | >10 μM | >2 μM | >2 μM | >10 μM |
| 50 | >10 μM | 0.89 μM | >2 μM | >10 μM |
| 51 | >10 μM | 0.85 μM | >2 μM | >10 μM |
| 52 | >10 μM | >2 μM | >2 μM | >10 μM |
| 53 | >10 μM | >2 μM | >2 μM | >10 μM |
| 54 | >10 μM | >2 μM | >2 μM | >10 μM |
| 55 | >10 μM | 0.92 μM | >2 μM | >10 μM |
| 56 | >2 μM | 1.09 μM | >2 μM | >10 μM |
| 57 | >10 μM | >2 μM | >2 μM | >10 μM |
| 58 | >10 μM | 0.70 μM | >2 μM | >10 μM |
| 59 | >10 μM | 0.84 μM | >2 μM | >10 μM |
| 60 | >10 μM | >2 μM | >2 μM | >10 μM |
| 61 | >10 μM | >2 μM | >2 μM | >10 μM |
| 62 | >10 μM | >2 μM | >2 μM | >10 μM |
| 63 | >10 μM | >2 μM | >2 μM | >10 μM |
| 64 | >10 μM | 0.90 μM | >2 μM | >10 μM |
| 65 | >10 μM | >2 μM | >2 μM | >10 μM |
| 66 | >10 μM | >2 μM | >2 μM | >10 μM |

TABLE 13-continued

| Compound No. | Cervical carcinoma HeLa | Ovarian cancer OVCAR-3 | Renal cancer ACHN | Papilloma RT4 |
|---|---|---|---|---|
| 67 | >10 μM | >2 μM | >2 μM | >10 μM |
| 68 | >2 μM | 1.16 μM | >2 μM | >10 μM |
| 69 | >10 μM | 1.13 μM | >2 μM | >10 μM |
| 70 | >10 μM | 1.18 μM | >2 μM | >10 μM |
| 71 | >10 μM | 1.31 μM | >2 μM | >10 μM |
| 72 | >2 μM | 0.73 μM | >2 μM | >10 μM |
| 73 | >10 μM | 1.11 μM | >2 μM | >10 μM |
| 74 | >10 μM | 0.98 μM | >2 μM | >10 μM |
| 75 | >10 μM | 1.36 μM | >2 μM | >10 μM |
| 76 | >10 μM | 1.46 μM | >2 μM | >10 μM |
| 77 | >10 μM | 1.13 μM | >2 μM | >10 μM |
| 78 | >10 μM | 1.01 μM | >2 μM | >10 μM |
| 79 | >10 μM | >2 μM | >2 μM | >10 μM |
| 80 | >10 μM | >2 μM | >2 μM | >10 μM |
| 81 | >10 μM | >2 μM | >2 μM | >10 μM |
| 82 | >10 μM | >2 μM | >2 μM | >10 μM |
| 83 | >10 μM | 0.82 μM | >2 μM | >10 μM |
| 84 | >10 μM | 0.59 μM | 1.3765 | >10 μM |
| 85 | >10 μM | >2 μM | >2 μM | >10 μM |
| 86 | >2 μM | 0.38 μM | 1.3337 | >10 μM |
| 87 | >10 μM | >2 μM | >2 μM | >10 μM |
| 88 | >10 μM | >2 μM | >2 μM | >10 μM |
| 89 | >10 μM | 0.86 μM | >2 μM | >10 μM |
| 90 | >10 μM | >2 μM | >2 μM | >10 μM |
| 91 | >10 μM | 1.74 μM | >2 μM | >10 μM |
| 92 | >10 μM | >2 μM | >2 μM | >10 μM |
| 93 | >10 μM | >2 μM | >2 μM | >10 μM |
| 94 | >10 μM | 1.10 μM | >2 μM | >10 μM |
| 95 | >2 μM | 0.38 μM | 1.1911 | >10 μM |
| 96 | >2 μM | 0.75 μM | 1.6698 | >10 μM |
| 97 | >2 μM | 0.59 μM | 1.3287 | >10 μM |
| 98 | >2 μM | 1.23 μM | 1.8121 | >10 μM |
| 99 | >2 μM | 0.63 μM | 1.206 | >10 μM |
| 100 | >2 μM | >2 μM | >2 μM | >10 μM |
| 101 | >2 μM | 1.99 μM | >2 μM | >10 μM |
| 102 | >2 μM | 0.93 μM | 1.6277 | >10 μM |
| 103 | >2 μM | >2 μM | >2 μM | >10 μM |
| 104 | >2 μM | 0.84 μM | 1.1984 | >10 μM |
| 105 | >2 μM | >2 μM | >2 μM | >10 μM |
| 106 | >2 μM | >2 μM | >2 μM | >10 μM |
| 107 | >2 μM | >2 μM | >2 μM | >10 μM |

As shown in the results of Tables 5 to 13, the compounds according to the present invention were very effective for inhibiting the formation of a c-Myc/Max/DNA complex, and were very effective for suppressing bladder cancer cell lines.

Moreover, the compounds were very effective for suppressing survival of prostate cancer cells. More specifically, it was confirmed that the effect of inhibiting survival of cells was shown to be the highest in DU145/TXR which is a hormone-independent docetaxel-resistant prostate cancer cell line.

Further, the compounds were very effective for suppressing survival of lung cancer cells. More specifically, it was confirmed that the effect of inhibiting survival of cells was shown to be high in lung cancer cells NCI-H23 and NCI-H1229 cells which are very highly dependent on c-Myc.

Moreover, the compounds were very effective for suppressing survival of breast cancer cells. More specifically, it was confirmed that the anti-hormone therapy could not be applied, and the effect of inhibiting survival of cells was shown to be high in breast cancer cell lines MDA-MB-231, SK-BR-3, MDA-MB-468, and HCC1954 which are very highly dependent on c-Myc.

Further, the compounds were very effective for suppressing survival of blood cancer cells. More specifically, it was confirmed that the effect of inhibiting survival of cells was shown to be high in blood cancer cells HL-60, Jurkat, Raji, Ramos, Daudi, and MOLT-4 which are very highly dependent on c-Myc.

Furthermore, the compounds were very effective for suppressing survival of pancreatic cancer cells. More specifically, it was confirmed that the effect of inhibiting survival of cells was shown to be high in pancreatic cancer cells MIA PaCa-2 which are very highly dependent on c-Myc.

Moreover, the compounds were very effective for suppressing survival of colorectal cancer cells. More specifically, it was confirmed that the effect of inhibiting survival of cells was shown to be high in colorectal cell lines DLD-1, HCT 116, SW620, HCT-15, HCT-8, and RKO which are very highly dependent on c-Myc.

Moreover, the compounds were very effective for suppressing survival of brain cancer, neuroblastoma, melanoma, liver cancer, cervical carcinoma, ovarian cancer, and renal cancer cells.

Moreover, the compounds exhibited high selectivity which does not affect survival of RT4 cells which are papilloma cells.

Example 4. Evaluation of Selectivity of Compounds of the Present Invention

The selectivity of the compounds of the present invention for cancer cells was evaluated in the same manner as performed in Cell based assay in Example 3-2. As a comparative example, KSI-3716, the compound of Formula 4, which is a conventionally known compound, was used. The measurement results are shown in the following Table 14.

TABLE 14

| | Cytotoxicity (uM) | | | | |
|---|---|---|---|---|---|
| Compd. | MBT-2 | KU19-19 | UM-UC-3 | 253J | RT4 |
| KSI-3716 | 1.18 | 0.82 | 0.82 | 0.98 | 1.25 |
| Compound 56 | 1.18 | 0.90 | 1.25 | 1.11 | >10 |
| Compound 99 | 0.47 | 1.12 | 0.77 | 0.80 | >10 |

MBT-2: Mouse bladder transitional cell carcinoma
KU-19-19: Bladder carcinoma
253J: human urinary tract transitional cell carcinoma
UM-UC-3: human urinary bladder transitional cell carcinoma
RT4: human urinary bladder transitional cell papilloma As shown in Table 14, compound KSI-3716 caused nonselective apoptosis in both benign (RT4) and malignant (MBT-2, KU19-19, UM-UC-3 and 253J) bladder cancer cell lines, but the compounds of the present invention killed only malignant cancer cells with high selectivity.

All documents mentioned herein are incorporated herein by reference as the contents thereof are described herein. When introducing elements of the present invention or the preferred embodiment(s) thereof, the articles "a", "an", "the" and "said" are intended to mean that there are one or more of the elements. The terms "comprising", "including", and "having" are intended to be inclusive and mean that there may be additional elements other than the listed elements. Although the present invention is described with respect to particular aspects or embodiments, it should not be construed as limiting the details of these aspects.

INDUSTRIAL APPLICABILITY

The present invention provides a pharmaceutical composition containing, as an active ingredient, a compound capable of exhibiting various pharmacological activities by inhibiting the formation of a c-Myc/Max/DNA complex, a medical use (particularly, an anticancer use) thereof, and a treatment method including administering the same to a subject in need of treatment or prevention. The compound according to the present invention or a pharmaceutically acceptable salt thereof can exhibit an excellent medical effect due to excellent safety and high selectivity in terms of inhibiting the formation of the c-Myc/Max/DNA complex.

The invention claimed is:

1. A method of treating a cancer in a subject in need thereof, comprising administering to the subject a pharmaceutical composition comprising a compound of the following Formula 1a or 1b or a pharmaceutically acceptable salt thereof as an active ingredient:

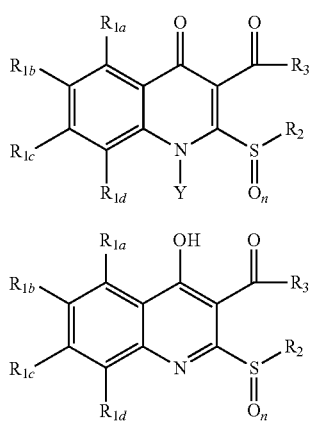

[Formula 1a]

[Formula 1b]

wherein:
- $R_{1a}$ to $R_{1d}$ are each independently selected from the group consisting of hydrogen, a halogen, a $C_{1-6}$ alkyl, a $C_{1-6}$ haloalkyl, a $C_{1-6}$ hydroxyalkyl, a $C_{1-6}$ alkoxy, a $C_{1-6}$ haloalkoxy, a $C_{2-10}$ alkenyl, a $C_{2-10}$ haloalkenyl, a $C_{2-10}$ alkynyl, a $C_{2-10}$ haloalkynyl, a hydroxyl group, nitro, cyano, a $C_{1-6}$ alkoxycarbonyl, amino, a $C_{1-6}$ alkylamino, a di($C_{1-6}$ alkyl)amino, an amino($C_{1-6}$)alkyl, a ($C_{1-6}$)alkylamino($C_{1-6}$)alkyl, a $C_{1-6}$ alkanoyl, a $C_{3-7}$ cycloalkyl, an aryl, a heterocycle, and a heteroaryl, wherein $R_{1a}$ to $R_{1d}$ are each optionally substituted, $R_2$ is selected from the group consisting of hydrogen, a $C_{1-6}$ alkyl, a ($C_{1-6}$)alkoxy($C_{1-6}$)alkyl, a $C_{1-6}$ haloalkyl, a $C_{1-6}$ hydroxyalkyl, a $C_{1-6}$ alkoxy, a $C_{1-6}$ haloalkoxy, a $C_{2-10}$ alkenyl, a $C_{2-10}$ alkenyl carboxy, a $C_{2-10}$ l haloalkenyl, a $C_{2-10}$ alkynyl, a $C_{2-10}$ haloalkynyl, a hydroxyl group, nitro, cyano, a $C_{1-6}$ alkoxycarbonyl, amino, a $C_{1-6}$ alkylamino, a $C_{1-6}$ cyanoalkyl, a di($C_{1-6}$ alkyl)amino, an amino($C_{1-6}$)alkyl, a ($C_{1-6}$)alkylamino($C_{1-6}$)alkyl, a $C_{1-6}$ alkanoyl, a $C_{3-7}$ cycloalkyl, a ($C_{1-6}$)alkyl($C_{3-7}$)cycloalkyl, an aryl, a ($C_{1-6}$)alkylaryl, a ($C_{1-6}$)haloalkylaryl, a ($C_{2-6}$)alkenylamide($C_{1-6}$)alkylalkoxy, a heterocycle, a ($C_{1-6}$)alkylheterocycle, a heteroaryl, and a ($C_{1-6}$)alkylheteroaryl, wherein $R_2$ is optionally substituted,
- $R_3$ is selected from the group consisting of a $C_{1-4}$ alkyl, an isoalkyl, a cycloalkyl, phenyl, and a $C_{1-4}$ haloalkyl,
- n is an integer of 0 to 2, and
- Y is selected from the group consisting of hydrogen, an alkyl, a haloalkyl, —C(O)alkyl, —C(O)aryl, a sulfonylalkyl, a sulfonylaryl, an aryl, and an alkylaryl, wherein the alkyl has 1 to 10 carbon atoms, preferably 1 to 4 carbon atoms, and the aryl is optionally substituted, and wherein the cancer is selected from the group consisting of bladder cancer, prostate cancer, lung cancer, breast cancer, blood cancer, pancreatic cancer, colorectal cancer, brain cancer, neuroblastoma, melanoma, liver cancer, cervical carcinoma, ovarian cancer, renal cancer, and papilloma.

2. The method of claim 1, wherein the active ingredient has a structure of Formula 2a or 2b, or a pharmaceutically acceptable salt thereof:

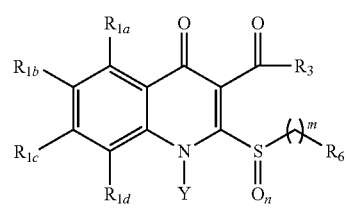

[Formula 2a]

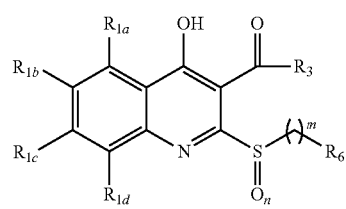

[Formula 2b]

wherein:
- $R_{1a}$ to $R_{1d}$, $R_3$, n, and Y are the same as defined in claim 1,
- m is an integer of 0 to 4, and
- $R_6$ is selected from the group consisting of phenyl, oxazole, pyrazole, pyrrole, imidazole, thiazole, thiophene, pyridine, pyrimidine, furan, indole, benzopyrazole, benzothiazole, benzooxazole, isoxazole, benzoimidazole, 1,2,5-oxadiazole, pyrrolo[2,3-b]pyridine, or benzothiophene, which are unsubstituted or are optionally substituted with one or more of hydrogen, a $C_{1-6}$ alkyl, a $C_{1-6}$ haloalkyl, a $C_{1-6}$ alkoxy, a halogen or one or more of hydrogen, phenyl, oxazole, pyrazole, pyrrole, imidazole, thiazole, thiophene, pyridine, pyrimidine, furan, indole, benzopyrazole, benzothiazole, benzooxazole, isoxazole, benzoimidazole, and benzothiophene, and optionally substituted with unsubstituted phenyl.

3. The method of claim 2, wherein one or more of $R_{1a}$ to $R_{1d}$ is a halogen, $R_3$ is a $C_{1-4}$ alkyl, a $C_{1-4}$ alkoxy, a $C_{1-4}$ haloalkyl, or a $C_{1-4}$ haloalkoxy, and m is 1 or 2.

4. The method of claim 1, wherein the active ingredient is a compound of Formula 3a or 3b, or is a pharmaceutically acceptable salt thereof:

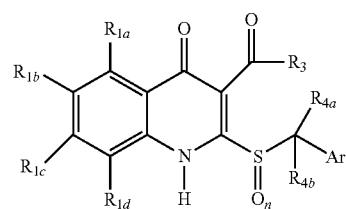

[Formula 3a]

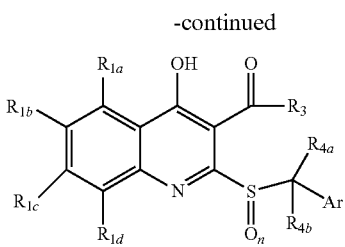

[Formula 3b]

wherein:
R$_{1a}$ to R$_{1d}$, R$_3$, and n are the same as defined in claim 1,
R$_{4a}$ and R$_{4b}$ are each independently selected from the group consisting of hydrogen, a halogen, a C$_{1-4}$ alkyl, a C$_{1-4}$ haloalkyl, and a C$_{1-4}$ alkyl, wherein one or more hydrogen(s) is substituted with a substituent other than a halogen,
Ar is phenyl, a 5 to 6-membered heteroaryl, or an 8 to 12-membered biheteroaryl, wherein the heteroaryl comprises one or more of N, S, and O in the ring, and wherein Ar is optionally substituted with one or more of a halogen, a C$_{1-6}$ alkyl, a C$_{1-6}$ alkylthio, a C$_{1-6}$ haloalkyl, a C$_{1-6}$ haloalkylthio, a C$_{1-6}$ alkoxy, a C$_{1-6}$ haloalkoxy, a C$_{2-10}$ alkenyl, a C$_{2-10}$ haloalkenyl, a C$_{2-10}$ alkynyl, a C$_{2-10}$ haloalkynyl, a hydroxyl group, COOH, nitro, cyano, a C$_{1-6}$ alkoxycarbonyl, amino, a C$_{1-6}$ alkylamino, a di(C$_{1-6}$ alkyl)amino, an amino (C$_{1-6}$)alkyl, a (C$_{1-6}$)alkylamino$_{(C1-6)}$alkyl, a (C$_{1-6}$) alkoxy$_{(C1-6)}$alkylamino, a (C$_{1-6}$)alkylamino(C$_{1-6}$) alkylamino, a C$_{1-6}$ alkanoyl, SF$_5$, S(O)CF$_3$, SCF$_3$, NHC(=O)CH$_3$, C(=O)NHCH$_3$, NHSO$_2$CH$_3$, a C$_{3-7}$ cycloalkyl, an aryl, benzoyl, a heterocycle, a heteroaryl, phenyl, oxazole, pyrazole, pyrrole, imidazole, thiazole, thiophene, pyridine, pyrimidine, furan, indole, benzopyrazole, benzothiazole, benzooxazole, isoxazole, benzoimidazole, and benzothiophene, and the substituent(s) of Ar is unsubstituted or is substituted with one or more selected from the group consisting of CF$_3$, a halogen, a C$_{1-3}$ alkyl, a C$_{1-3}$ haloalkyl, a hydroxyl group, COOH, nitro, cyano, amino, a di(C$_{1-3}$ alkyl)amino, NHC(=O)CH$_3$ and C(=O)NHCH$_3$.

5. The method of claim 4, wherein one or more of R$_{1a}$ to R$_{1d}$ is a halogen, R$_3$ is a C$_{1-4}$ alkyl, a C$_{1-4}$ alkoxy, a C$_{1-4}$ haloalkyl, or a C$_{1-4}$ haloalkoxy, and R$_5$ is a C$_{1-4}$ alkyl, a halogen, or a C$_{1-4}$ cycloalkyl.

6. The method of claim 1, wherein the active ingredient is selected from the group consisting of:
3-acetyl-8-bromo-5-chloro-2-(methylsulfinyl)quinolin-4 (1H)-one,
3-acetyl-8-bromo-5-chloro-2-(methylthio)quinolin-4 (1H)-one,
3-acetyl-2-(benzylthio)-8-bromo-5-chloroquinolin-4 (1H)-one,
3-acetyl-2-(benzylsulfinyl)-8-bromo-5-chloroquinolin-4 (1H)-one,
3-acetyl-8-bromo-5-chloro-1-methyl-2-(methylthio)quinolin-4(1H)-one,
3-acetyl-5,8-dichloro-2-(methylsulfinyl)quinolin-4(1H)-one,
3-acetyl-6-fluoro-1-methyl-2-(methylthio)quinolin-4 (1H)-one,
1-(6-fluoro-4-hydroxy-2-(methylthio)quinolin-3-yl) ethan-1-one,
3-acetyl-8-bromo-1-(4-bromobenzoyl)-5-chloro-2-(methylsulfinyl)quinolin-4(1H)-one,
3-acetyl-8-bromo-5-chloro-2-((4-chlorobenzyl)thio)quinolin-4(1H)-one,
3-acetyl-8-bromo-5-chloro-2-((4-chlorobenzyl)sulfinyl) quinolin-4(1 H)-one,
3-acetyl-8-bromo-5-chloro-2-(phenylthio)quinolin-4(1 H)-one,
3-acetyl-8-bromo-5-chloro-2-(phenylsulfinyl)quinolin-4 (1 H)-one,
3-acetyl-8-bromo-5-chloro-2-((2-methoxyphenyl)thio) quinolin-4(1 H)-one,
3-acetyl-8-bromo-5-chloro-2-((2-methoxyphenyl)sulfinyl)quinolin-4(1 H)-one,
3-acetyl-8-bromo-2-((4-bromophenyl)thio)-5-chloroquinolin-4(1 H)-one,
3-acetyl-8-bromo-2-((4-bromophenyl)sulfinyl)-5-chloroquinolin-4(1 H)-one,
1,1'-(8-bromo-5-chloro-2-(methylthio)-4-oxoquinoline-1, 3(4H)-diyl)bis(ethan-1-one),
1,1'-(8-bromo-5-chloro-2-(methylsulfinyl)-4-oxoquinoline-1,3(4H)-diyl)bis(ethan-1-one),
3-acetyl-2-(benzylsulfinyl)-8-bromo-1-(4-bromobenzoyl)-5-chloroquinolin-4(1 H)-one,
3-acetyl-8-bromo-1-(4-bromobenzoyl)-5-chloro-2-(methylsulfonyl)quinolin-4(1 H)-one,
3-acetyl-8-bromo-5-chloro-1-(3-chloro-4-fluorobenzyl)-2-(methylsulfinyl)quinolin-4(1 H)-one,
3-acetyl-2-(benzylthio)-8-bromo-1-(4-bromobenzoyl)-5-chloroquinolin-4(1 H)-one,
3-acetyl-8-bromo-5-chloro-2-(isopropylthio)quinolin-4(1 H)-one,
3-acetyl-8-bromo-5-chloro-2-(isopropylsulfinyl)quinolin-4(1 H)-one,
3-acetyl-8-bromo-5-chloro-2-((1-phenylethyl)sulfinyl) quinolin-4(1 H)-one,
3-(((3-acetyl-8-bromo-5-chloro-4-oxo-1,4-dihydroquinolin-2-yl)thio)methyl)benzonitrile,
3-(((3-acetyl-8-bromo-5-chloro-4-oxo-1,4-dihydroquinolin-2-yl)sulfinyl)methyl)benzonitrile,
3-acetyl-8-bromo-5-chloro-2-((2,4-difluorobenzyl)sulfinyl)quinolin-4(1 H)-one,
3-acetyl-8-bromo-5-chloro-2-((3-chloro-4-fluorobenzyl) thio)quinolin-4(1 H)-one,
3-acetyl-8-bromo-5-chloro-2-((3-chloro-4-fluorobenzyl) sulfinyl)quinolin-4(1 H)-one,
3-acetyl-8-bromo-5-chloro-2-((4-nitrobenzyl)thio)quinolin-4(1 H)-one,
3-acetyl-8-bromo-5-chloro-2-((4-nitrobenzyl)sulfinyl) quinolin-4(1 H)-one,
3-acetyl-2-(benzylsulfonyl)-8-bromo-5-chloroquinolin-4(1 H)-one,
3-acetyl-8-bromo-5-chloro-1-(methylsulfonyl)-2-(methylthio)quinolin-4(1 H)-one,
3-acetyl-8-bromo-5-chloro-2-(methylsulfinyl)-1-((trifluoromethyl)sulfonyl)quinolin-4(1 H)-one,
3-acetyl-8-bromo-5-chloro-1-((4-chlorophenyl)sulfonyl)-2-(methylthio)quinolin-4(1 H)-one,
3-acetyl-8-bromo-5-chloro-2-(methylthio)-1-((4-nitrophenyl)sulfonyl)quinolin-4(1 H)-one,
3-acetyl-8-bromo-5-chloro-1-(ethylsulfonyl)-2-(methylsulfinyl)quinolin-4(1 H)-one,
3-acetyl-8-bromo-1-((4-(tert-butyl)phenyl)sulfonyl)-5-chloro-2-(methylthio)quinolin-4(1 H)-one,
3-acetyl-8-bromo-1-((4-(tert-butyl)phenyl)sulfonyl)-5-chloro-2-(methylsulfonyl)quinolin-4(1 H)-one, 3-acetyl-8-bromo-1-((4-(tert-butyl)phenyl)sulfonyl)-5-chloro-2-(methylsulfinyl)quinolin-4(1H)-one,
3-acetyl-8-bromo-5-chloro-2-((2,5-dichlorobenzyl)thio)quinolin-4(1H)-one,
3-acetyl-8-bromo-5-chloro-2-((2,5-dichlorobenzyl)sulfinyl)quinolin-4(1H)-one,
3-acetyl-8-bromo-5-chloro-2-((3,5-difluorobenzyl)thio)quinolin-4(1H)-one,
3-acetyl-8-bromo-5-chloro-2-((3,5-difluorobenzyl)sulfinyl)quinolin-4(1H)-one,
3-acetyl-8-bromo-5-chloro-2-((3-iodobenzyl)thio)quinolin-4(1H)-one,
3-acetyl-8-bromo-5-chloro-2-((3-iodobenzyl)sulfinyl)quinolin-4(1H)-one,
3-acetyl-8-bromo-5-chloro-2-((3-fluorobenzyl)thio)quinolin-4(1H)-one,
3-acetyl-8-bromo-5-chloro-2-((3-fluorobenzyl)sulfinyl)quinolin-4(1H)-one,
3-acetyl-8-bromo-5-chloro-2-(((5-methylisoxazol-3-yl)methyl)sulfinyl)quinolin-4(1H)-one,
1-(2-(benzylthio)-8-bromo-5-chloro-4-hydroxyquinolin-3-yl)ethan-1-one,
1-(2-(benzylsulfinyl)-8-bromo-5-chloro-4-hydroxyquinolin-3-yl)ethan-1-one,
1-(2-(benzylsulfonyl)-8-bromo-5-chloro-4-hydroxyquinolin-3-yl)ethan-1-one,
3-acetyl-8-bromo-5-chloro-2-((3-methoxybenzyl)sulfinyl)quinolin-4(1H)-one,
3-acetyl-8-bromo-5-chloro-2-((4-((trifluoromethyl)thio)benzyl)sulfinyl)quinolin-4(1H)-one,
3-acetyl-5,8-dichloro-2-((4-nitrobenzyl)sulfinyl)quinolin-4(1H)-one,
2-(((3-acetyl-8-bromo-5-chloro-4-oxo-1,4-dihydroquinolin-2-yl)sulfinyl)methyl)benzonitrile,
3-acetyl-8-bromo-5-chloro-2-((3,5-dimethoxybenzyl)sulfinyl)quinolin-4(1H)-one,
3-acetyl-8-bromo-2-((4-(tert-butyl)benzyl)sulfinyl)-5-chloroquinolin-4(1H)-one,
3-acetyl-8-bromo-5-chloro-2-((methoxymethyl)thio)quinolin-4(1H)-one,
3-acetyl-8-bromo-5-chloro-2-mercaptoquinolin-4(1H)-one,
3-acetyl-2-((4-benzoylbenzyl)sulfinyl)-8-bromo-5-chloroquinolin-4(1H)-one,
3-acetyl-8-bromo-5-chloro-2-((4-((trifluoromethyl)sulfinyl)benzyl)sulfinyl)quinolin-4(1H)-one,
2-(((3-acetyl-8-bromo-5-chloro-4-oxo-1,4-dihydroquinolin-2-yl)sulfinyl)acetonitrile,
2(((3-acetyl-8-bromo-5-chloro-4-oxo-1,4-dihydroquinolin-2-yl)thio)acetonitrile,
(Z)-3-((3-acetyl-8-bromo-5-chloro-4-oxo-1,4-dihydroquinolin-2-yl)thio)acrylic acid,
3-acetyl-8-bromo-5-chloro-24(4-(pentafluoro-16-sulfanyl)benzyl)sulfinyl)quinolin-4(1H)-one,
3-acetyl-8-bromo-5-chloro-2-((2-fluoro-4-(pentafluoro-16-sulfanyl)benzyl)sulfinyl)quinolin-4(1H)-one,
3-acetyl-8-bromo-5-chloro-2-((4-(trifluoromethyl)benzyl)sulfinyl)quinolin-4(1H)-one,
3-acetyl-8-bromo-5-chloro-2-((4-(trifluoromethoxy)benzyl)sulfinyl)quinolin-4(1H)-one,
3-acetyl-8-bromo-5-chloro-2-(((5-(trifluoromethyl)furan-2-yl)methyl)sulfinyl)quinolin-4(1H)-one,
4-(((3-acetyl-8-bromo-5-chloro-4-oxo-1,4-dihydroquinolin-2-yl)sulfinyl)methyl)benzonitrile,
3-acetyl-8-bromo-5-chloro-2-((2-chloro-6-fluorobenzyl)sulfinyl)quinolin-4(1H)-one,
3-acetyl-8-bromo-5-chloro-2-((2-methoxy-4-(pentafluoro-16-sulfanyl)benzyl)sulfinyl)quinolin-4(1H)-one,
3-acetyl-8-bromo-5-chloro-2-((3-fluoro-5-(pentafluoro-16-sulfanyl)benzyl)sulfinyl)quinolin-4(1H)-one,
3-acetyl-8-bromo-5-chloro-24(3-(pentafluoro-16-sulfanyl)benzyl)sulfinyl)quinolin-4(1H)-one,
3-acetyl-8-bromo-5-chloro-2-(((perfluorophenyl)methyl)sulfinyl)quinolin-4(1H)-one,
3-acetyl-5,8-dichloro-2-((4-((trifluoromethyl)thio)benzyl)sulfinyl)quinolin-4(1H)-one,
3-acetyl-5,8-difluoro-24(4-(pentafluoro-16-sulfanyl)benzyl)sulfinyl)quinolin-4(1H)-one,
3-acetyl-5,8-difluoro-2-(((5-(trifluoromethyl)furan-2-yl)methyl)sulfinyl)quinolin-4(1H)-one,
3-acetyl-5,8-difluoro-2-(((5-methylisoxazol-3-yl)methyl)sulfinyl)quinolin-4(1H)-one,
3-acetyl-5,8-dichloro-2-((4-iodobenzyl)sulfinyl)quinolin-4(1H)-one,
3-acetyl-8-bromo-5-chloro-2-((pyridin-3-ylmethyl)sulfinyl)quinolin-4(1H)-one,
5,8-difluoro-3-isobutyryl-2-((4-((trifluoromethyl)thio)benzyl)sulfinyl)quinolin-4(1H)-one,
5,8-dichloro-3-isobutyryl-2-(((5-methylisoxazol-3-yl)methyl)sulfinyl)quinolin-4(1H)-one,
3-benzoyl-5,8-difluoro-24(4-(pentafluoro-16-sulfanyl)benzyl)sulfinyl)quinolin-4(1H)-one,
3-benzoyl-5,8-dichloro-2-(((5-methylisoxazol-3-yl)methyl)sulfinyl)quinolin-4(1H)-one,
methyl 5-(((3-acetyl-5,8-dichloro-4-oxo-1,4-dihydroquinolin-2-yl)sulfinyl)methyl)furan-2-carboxylate,
2-(((3-acetyl-5,8-dichloro-4-oxo-1,4-dihydroquinolin-2-yl)sulfinyl)methyl)isoindoline-1,3-dione,
methyl 4-(((3-acetyl-5,8-dichloro-4-oxo-1,4-dihydroquinolin-2-yl)sulfinyl)methyl)benzoate,
3-acetyl-5-methoxy-24(4-(pentafluoro-16-sulfanyl)benzyl)thio)quinolin-4(1H)-one,
3-acetyl-5-methoxy-24(4-(pentafluoro-16-sulfanyl)benzyl)sulfinyl)quinolin-4(1H)-one,
3-acetyl-5-methoxy-2-(((5-methylisoxazol-3-yl)methyl)sulfinyl)quinolin-4(1H)-one,
8-bromo-5-chloro-3-isobutyryl-2-(((5-methylisoxazol-3-yl)methyl)sulfinyl)quinolin-4(1H)-one,
8-bromo-5-chloro-3-(cyclopropanecarbonyl)-2-(((5-methylisoxazol-3-yl)methyl)sulfinyl)quinolin-4(1H)-one,
5,8-dichloro-3-(cyclopropanecarbonyl)-2-(((5-methylisoxazol-3-yl)methyl)sulfinyl)quinolin-4(1H)-one,
5-(((3-acetyl-8-bromo-5-chloro-4-oxo-1,4-dihydroquinolin-2-yl)sulfinyl)methyl)thiophene-2-carbonitrile,
2-(((6-(1H-pyrazol-1-yl)pyridin-3-yl)methyl)sulfinyl)-3-acetyl-8-bromo-5-chloroquinolin-4(1H)-one,
3-acetyl-2-(((6-aminopyridin-3-yl)methyl)sulfinyl)-8-bromo-5-chloroquinolin-4(1H)-one,
8-bromo-5-chloro-3-(cyclopropanecarbonyl)-2-((4-((trifluoromethyl)thio)benzyl)sulfinyl)quinolin-4(1H)-one,
3-acetyl-8-bromo-5-chloro-2-(((2-methyl-6-(trifluoromethyl)pyridin-3-yl)methyl)sulfinyl)quinolin-4(1H)-one,
N-(4-(((3-acetyl-8-bromo-5-chloro-4-oxo-1,4-dihydroquinolin-2-yl)sulfinyl)methyl)phenyl)methanesulfonamide,
3-acetyl-8-bromo-5-chloro-2-(((6-chloropyridin-3-yl)methyl)sulfinyl)quinolin-4(1H)-one,
3-acetyl-8-bromo-5-chloro-2-(((6-((2-methoxyethyl)amino)pyridin-3-yl)methyl)sulfinyl)quinolin-4(1H)-one, 3-acetyl-8-bromo-5-chloro-2-(((4-methyl-1,2,5-oxadiazol-3-yl)methyl)sulfinyl)quinolin-4(1H)-one, 2-(((1H-pyrrolo[2,3-b]pyridin-5-yl)methyl)sulfinyl)-3-acetyl-8-bromo-5-chloroquinolin-4(1H)-one, and a pharmaceutically acceptable salt thereof.

7. The method of claim 1, wherein the pharmaceutical composition comprises a second active agent having an anticancer effect.

8. The method of claim 1, wherein Y is hydrogen, an alkyl, a haloalkyl, —C(O)alkyl, —C(O)aryl, a sulfonylalkyl, a sulfonylaryl, an aryl, or an alkylaryl, wherein the alkyl has 1 to 4 carbon atoms.

* * * * *